US010646504B2

(12) United States Patent
DeRosa et al.

(10) Patent No.: US 10,646,504 B2
(45) Date of Patent: *May 12, 2020

(54) SYNERGISTIC ENHANCEMENT OF THE DELIVERY OF NUCLEIC ACIDS VIA BLENDED FORMULATIONS

(71) Applicant: Translate Bio, Inc., Lexington, MA (US)

(72) Inventors: Frank DeRosa, Lexington, MA (US); Lianne Smith, Lexington, MA (US); Michael Heartlein, Lexington, MA (US); Braydon Charles Guild, Concord, MA (US)

(73) Assignee: Translate Bio, Inc., Lexington, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/157,050

(22) Filed: Oct. 10, 2018

(65) Prior Publication Data
US 2019/0216843 A1 Jul. 18, 2019

Related U.S. Application Data

(63) Continuation of application No. 14/775,818, filed as application No. PCT/US2014/028498 on Mar. 14, 2014, now Pat. No. 10,130,649.

(60) Provisional application No. 61/789,375, filed on Mar. 15, 2013.

(51) Int. Cl.
| A61K 31/7105 | (2006.01) |
| A61K 9/127 | (2006.01) |
| A61K 48/00 | (2006.01) |
| A61K 9/14 | (2006.01) |
| A61K 9/00 | (2006.01) |

(52) U.S. Cl.
CPC ........ *A61K 31/7105* (2013.01); *A61K 9/1271* (2013.01); *A61K 9/1272* (2013.01); *A61K 9/145* (2013.01); *A61K 9/146* (2013.01); *A61K 48/0025* (2013.01); *A61K 48/0033* (2013.01); *A61K 9/0019* (2013.01); *A61K 9/0085* (2013.01)

(58) Field of Classification Search
CPC .............. A61K 31/7105; A61K 9/0019; A61K 9/0085; A61K 9/1271; A61K 9/1272; A61K 9/145; A61K 9/146; A61K 48/00; A61K 48/0025; A61K 48/0033
USPC ................ 424/450; 435/455, 458; 514/44 R
See application file for complete search history.

(56) References Cited

U.S. PATENT DOCUMENTS

| 5,705,385 A | 1/1998 | Bally et al. |
| 5,976,567 A | 11/1999 | Wheeler |
| 5,981,501 A | 11/1999 | Wheeler et al. |
| 6,534,484 B1 | 3/2003 | Wheeler et al. |
| 6,815,432 B2 | 11/2004 | Wheeler et al. |
| 7,422,902 B1 | 9/2008 | Wheeler et al. |
| 7,745,651 B2 | 6/2010 | Heyes et al. |
| 7,799,565 B2 | 9/2010 | MacLachlan et al. |
| 7,803,397 B2 | 9/2010 | Heyes et al. |
| 7,901,708 B2 | 3/2011 | MacLachlan et al. |
| 8,101,741 B2 | 1/2012 | MacLachlan et al. |
| 8,188,263 B2 | 5/2012 | MacLachlan et al. |
| 8,236,943 B2 | 8/2012 | Lee et al. |
| 8,329,070 B2 | 12/2012 | MacLachlan et al. |
| 8,513,403 B2 | 8/2013 | MacLachlan et al. |
| 8,569,256 B2 | 10/2013 | Heyes et al. |
| 8,710,200 B2 | 4/2014 | Schrum et al. |
| 8,822,663 B2 | 9/2014 | Schrum et al. |
| 8,883,202 B2 | 11/2014 | Manoharan et al. |
| 8,980,864 B2 | 3/2015 | Hoge et al. |
| 9,051,567 B2 | 6/2015 | Fitzgerald et al. |
| 9,061,059 B2 | 6/2015 | Chakraborty et al. |
| 9,089,604 B2 | 7/2015 | Chakraborty et al. |
| 9,095,552 B2 | 8/2015 | Chakraborty et al. |
| 9,107,886 B2 | 8/2015 | Chakraborty et al. |
| 9,114,113 B2 | 8/2015 | Chakraborty et al. |
| 9,181,319 B2 | 11/2015 | Schrum et al. |
| 9,186,325 B2 | 11/2015 | Manoharan et al. |
| 9,186,372 B2 | 11/2015 | de Fougerolles et al. |
| 9,187,748 B2 | 11/2015 | Geisbert et al. |
| 9,192,651 B2 | 11/2015 | Chakraborty et al. |
| 9,220,755 B2 | 12/2015 | Chakraborty et al. |
| 9,220,792 B2 | 12/2015 | Chakraborty et al. |

(Continued)

FOREIGN PATENT DOCUMENTS

| CA | 2807 552 | 9/2012 |
| EP | 1519 714 | 10/2010 |

(Continued)

OTHER PUBLICATIONS

Lee, et al., "Synergistic effect of polyethylenimine and cationic liposomes in nucleic acid delivery to human cancer cells." Biochim Biophys Acta, 1611(1-2): 55-62 (2003).

(Continued)

*Primary Examiner* — Janet L Epps-Smith
(74) *Attorney, Agent, or Firm* — Proskauer Rose LLP; Fangli Chen; Sang-Ah Kim

(57) ABSTRACT

Disclosed herein are pharmaceutical compositions that comprise "blends" of lipid nanoparticles and related methods of using such blended compositions to deliver polynucleotides to one or more target cells, tissues or organs. The blended compositions are generally characterized as being able to efficiently deliver polynucleotides to target cells and by their ability to enhance the expression of such polynucleotides and the production of functional proteins by target cells.

14 Claims, 9 Drawing Sheets

Specification includes a Sequence Listing.

(56) References Cited

U.S. PATENT DOCUMENTS

| | | |
|---|---|---|
| 9,233,141 B2 | 1/2016 | Chakraborty et al. |
| 9,254,311 B2 | 2/2016 | Bancel et al. |
| 9,295,689 B2 | 3/2016 | de Fougerolles et al. |
| 9,301,993 B2 | 4/2016 | Chakraborty et al. |
| 9,303,079 B2 | 4/2016 | Chakraborty et al. |
| 9,334,328 B2 | 5/2016 | Schrum et al. |
| 9,345,780 B2 | 5/2016 | Manoharan et al. |
| 9,352,042 B2 | 5/2016 | Heyes et al. |
| 9,352,048 B2 | 5/2016 | Manoharan et al. |
| 9,364,435 B2 | 6/2016 | Yaworski et al. |
| 9,370,489 B2 | 6/2016 | Yang et al. |
| 9,394,234 B2 | 7/2016 | Chen et al. |
| 9,404,127 B2 | 8/2016 | Yaworski et al. |
| 9,428,535 B2 | 8/2016 | de Fougerolles et al. |
| 9,428,751 B2 | 8/2016 | MacDonald et al. |
| 9,447,164 B2 | 9/2016 | Schrum et al. |
| 9,464,124 B2 | 10/2016 | Bancel et al. |
| 9,492,386 B2 | 11/2016 | MacLachlan et al. |
| 9,504,651 B2 | 11/2016 | MacLachlan et al. |
| 9,504,734 B2 | 11/2016 | Bancel et al. |
| 9,518,272 B2 | 12/2016 | Yaworski et al. |
| 9,572,874 B2 | 2/2017 | Fotin-Mleczek et al. |
| 9,572,896 B2 | 2/2017 | Bancel et al. |
| 9,572,897 B2 | 2/2017 | Bancel et al. |
| 9,587,003 B2 | 3/2017 | Bancel et al. |
| 9,616,084 B2 | 4/2017 | Mutzke |
| 9,623,095 B2 | 4/2017 | Kallen et al. |
| D787,703 S | 5/2017 | Mayer |
| 9,636,301 B2 | 5/2017 | Weber |
| 9,655,955 B2 | 5/2017 | Hoerr et al. |
| 9,657,295 B2 | 5/2017 | Schrum et al. |
| 9,669,089 B2 | 6/2017 | Thess et al. |
| 9,670,152 B2 | 6/2017 | Payne et al. |
| 9,675,668 B2 | 6/2017 | Bancel et al. |
| 9,682,139 B2 | 6/2017 | Monoharan et al. |
| 9,683,233 B2 | 6/2017 | Thess |
| 9,687,550 B2 | 6/2017 | Manoharan et al. |
| 9,688,729 B2 | 6/2017 | Kramps et al. |
| 2002/0192651 A1 | 12/2002 | Wheeler et al. |
| 2003/0181410 A1 | 9/2003 | Wheeler et al. |
| 2004/0142025 A1 | 7/2004 | MacLachlan et al. |
| 2006/0008910 A1 | 1/2006 | MacLachlan et al. |
| 2006/0083780 A1 | 4/2006 | Heyes et al. |
| 2006/0216343 A1 | 9/2006 | Panzner et al. |
| 2007/0135372 A1 | 6/2007 | MacLachlan et al. |
| 2009/0270481 A1 | 10/2009 | MacLachlan et al. |
| 2010/0041152 A1 | 2/2010 | Wheeler et al. |
| 2011/0244026 A1* | 10/2011 | Guild ............... A61K 31/7105 424/450 |
| 2011/0256175 A1 | 10/2011 | Hope et al. |
| 2011/0311583 A1 | 12/2011 | Manoharan et al. |
| 2012/0065252 A1 | 3/2012 | Schrum et al. |
| 2012/0128760 A1 | 5/2012 | Manoharan et al. |
| 2012/0142756 A1 | 6/2012 | Guild et al. |
| 2012/0202871 A1 | 8/2012 | Heyes et al. |
| 2012/0237975 A1 | 9/2012 | Schrum et al. |
| 2012/0251618 A1 | 10/2012 | Schrum et al. |
| 2012/0328668 A1 | 12/2012 | MacLachlan et al. |
| 2013/0195967 A1 | 8/2013 | Guild et al. |
| 2013/0237594 A1 | 9/2013 | de Fougerolles et al. |
| 2013/0245107 A1 | 9/2013 | de Fougerolles et al. |
| 2013/0259923 A1 | 10/2013 | Bancel et al. |
| 2013/0259924 A1 | 10/2013 | Bancel et al. |
| 2013/0266640 A1 | 10/2013 | de Fougerolles et al. |
| 2014/0010861 A1 | 1/2014 | Bancel et al. |
| 2014/0044772 A1 | 2/2014 | MacLachlan et al. |
| 2014/0105964 A1 | 4/2014 | Bancel et al. |
| 2014/0105965 A1 | 4/2014 | Bancel et al. |
| 2014/0147432 A1 | 5/2014 | Bancel et al. |
| 2014/0147454 A1 | 5/2014 | Chakraborty et al. |
| 2014/0148502 A1 | 5/2014 | Bancel et al. |
| 2014/0155472 A1 | 6/2014 | Bancel et al. |
| 2014/0155473 A1 | 6/2014 | Bancel et al. |
| 2014/0155474 A1 | 6/2014 | Bancel et al. |
| 2014/0155475 A1 | 6/2014 | Bancel et al. |
| 2014/0171485 A1 | 6/2014 | Bancel et al. |
| 2014/0179756 A1 | 6/2014 | MacLachlan et al. |
| 2014/0179771 A1 | 6/2014 | Bancel et al. |
| 2014/0186432 A1 | 7/2014 | Bancel et al. |
| 2014/0193482 A1 | 7/2014 | Bancel et al. |
| 2014/0194494 A1 | 7/2014 | Bancel et al. |
| 2014/0199371 A1 | 7/2014 | Bancel et al. |
| 2014/0200261 A1 | 7/2014 | Hoge et al. |
| 2014/0200262 A1 | 7/2014 | Bancel et al. |
| 2014/0200263 A1 | 7/2014 | Bancel et al. |
| 2014/0200264 A1 | 7/2014 | Bancel et al. |
| 2014/0206752 A1 | 7/2014 | Afeyan et al. |
| 2014/0206753 A1 | 7/2014 | Guild et al. |
| 2014/0206755 A1 | 7/2014 | Bancel et al. |
| 2014/0206852 A1 | 7/2014 | Hoge et al. |
| 2014/0221465 A1 | 8/2014 | Bancel et al. |
| 2014/0243399 A1 | 8/2014 | Schrum et al. |
| 2014/0249208 A1 | 9/2014 | Bancel et al. |
| 2014/0255467 A1 | 9/2014 | Bancel et al. |
| 2014/0255468 A1 | 9/2014 | Bancel et al. |
| 2014/0275227 A1 | 9/2014 | Hoge et al. |
| 2014/0275229 A1 | 9/2014 | Bancel et al. |
| 2014/0294937 A1 | 10/2014 | MacLachlan et al. |
| 2014/0343129 A1 | 11/2014 | de Fougerolles et al. |
| 2015/0005372 A1 | 1/2015 | Hoge et al. |
| 2015/0017211 A1 | 1/2015 | de Fougerolles et al. |
| 2015/0044277 A1 | 2/2015 | Bancel et al. |
| 2015/0050354 A1 | 2/2015 | Bouchon et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064242 A1 | 3/2015 | Heyes et al. |
| 2015/0064725 A1 | 3/2015 | Schrum et al. |
| 2015/0086614 A1 | 3/2015 | Bancel et al. |
| 2015/0111248 A1 | 4/2015 | Bancel et al. |
| 2015/0111945 A1 | 4/2015 | Geisbert et al. |
| 2015/0166465 A1 | 6/2015 | Chen et al. |
| 2015/0190515 A1 | 7/2015 | Manoharan et al. |
| 2015/0315541 A1 | 11/2015 | Bancel et al. |
| 2015/0315584 A1 | 11/2015 | MacDonald et al. |
| 2015/0366997 A1 | 12/2015 | Guild et al. |
| 2016/0082092 A1 | 3/2016 | Hoerr et al. |
| 2016/0089424 A1 | 3/2016 | Hoerr et al. |
| 2016/0095924 A1 | 4/2016 | Hope et al. |
| 2016/0114011 A1 | 4/2016 | Bancel et al. |
| 2016/0115477 A1 | 4/2016 | MacLachlan et al. |
| 2016/0115483 A1 | 4/2016 | MacLachlan et al. |
| 2016/0136236 A1 | 5/2016 | Hoge et al. |
| 2016/0151284 A1 | 6/2016 | Heyes et al. |
| 2016/0158385 A1 | 6/2016 | Bancel et al. |
| 2016/0193299 A1 | 7/2016 | de Fougerolles et al. |
| 2016/0194368 A1 | 7/2016 | Hoge et al. |
| 2016/0194625 A1 | 7/2016 | Hoge et al. |
| 2016/0199485 A1 | 7/2016 | Manoharan et al. |
| 2016/0213785 A1 | 7/2016 | Manoharan et al. |
| 2016/0237108 A1 | 8/2016 | Fraley et al. |
| 2016/0237134 A1 | 8/2016 | Hoge et al. |
| 2016/0250354 A1 | 9/2016 | Manoharan et al. |
| 2016/0251681 A1 | 9/2016 | Yaworski et al. |
| 2016/0256567 A1 | 9/2016 | Heyes et al. |
| 2016/0256568 A1 | 9/2016 | Heyes et al. |
| 2016/0256573 A1 | 9/2016 | de Fougerolles et al. |
| 2016/0264971 A1 | 9/2016 | Geisbert et al. |
| 2016/0264975 A1 | 9/2016 | Schrum et al. |
| 2016/0274089 A1 | 9/2016 | Ciufolini et al. |
| 2016/0304552 A1 | 10/2016 | Roy et al. |
| 2016/0317647 A1 | 11/2016 | Ciaramella et al. |
| 2016/0317676 A1 | 11/2016 | Hope et al. |
| 2016/0331828 A1 | 11/2016 | Ciaramella et al. |
| 2016/0348099 A1 | 12/2016 | Roy et al. |
| 2016/0354490 A1 | 12/2016 | Roy et al. |
| 2016/0354491 A1 | 12/2016 | Roy et al. |
| 2016/0354492 A1 | 12/2016 | Roy et al. |
| 2016/0354493 A1 | 12/2016 | Roy et al. |
| 2016/0367687 A1 | 12/2016 | Manoharan et al. |
| 2016/0367702 A1 | 12/2016 | Hoge et al. |
| 2016/0375134 A1 | 12/2016 | Bancel et al. |
| 2016/0375137 A9 | 12/2016 | Manoharan et al. |

(56) References Cited

U.S. PATENT DOCUMENTS

| | | |
|---|---|---|
| 2017/0000858 A1 | 1/2017 | Fotin-Mleczek et al. |
| 2017/0000870 A1 | 1/2017 | Hoerr et al. |
| 2017/0000871 A1 | 1/2017 | Probst et al. |
| 2017/0002060 A1 | 1/2017 | Bolen et al. |
| 2017/0007702 A1 | 1/2017 | Heyes et al. |
| 2017/0014496 A1 | 1/2017 | Fotin-Mleczek et al. |
| 2017/0028059 A1 | 2/2017 | Baumhof et al. |
| 2017/0029847 A1 | 2/2017 | Thess |
| 2017/0042814 A1 | 2/2017 | Yaworski et al. |
| 2017/0056528 A1 | 3/2017 | De Fougerolles et al. |
| 2017/0056529 A1 | 3/2017 | Thess et al. |
| 2017/0065675 A1 | 3/2017 | Bancel et al. |
| 2017/0065727 A1 | 3/2017 | Fotin-Mleczek et al. |
| 2017/0114378 A1 | 4/2017 | Wochner et al. |
| 2017/0128549 A1 | 5/2017 | Fotin-Mileczek et al. |
| 2017/0136131 A1 | 5/2017 | Roy et al. |
| 2017/0136132 A1 | 5/2017 | Roy et al. |
| 2017/0143631 A1 | 5/2017 | Chen et al. |
| 2017/0143796 A1 | 5/2017 | Schrum et al. |
| 2017/0151333 A1 | 6/2017 | Heyes et al. |
| 2017/0157268 A1 | 6/2017 | Ansell et al. |
| 2017/0166905 A1 | 6/2017 | Eberle et al. |
| 2017/0173128 A1 | 6/2017 | Hoge et al. |
| 2017/0175129 A1 | 6/2017 | Roy et al. |
| 2017/0182081 A1 | 6/2017 | Mutzke |
| 2017/0182150 A1 | 6/2017 | Kallen et al. |

FOREIGN PATENT DOCUMENTS

| | | |
|---|---|---|
| EP | 2449 106 | 5/2012 |
| EP | 2338 478 | 6/2013 |
| EP | 2823 809 | 1/2015 |
| WO | WO2005/026372 | 3/2005 |
| WO | WO2005/121348 A1 | 12/2005 |
| WO | WO2009/127060 | 10/2009 |
| WO | WO2010042877 A1 | 4/2010 |
| WO | WO2011/141705 | 11/2011 |
| WO | WO2012/019168 | 2/2012 |
| WO | WO2012/135805 | 10/2012 |
| WO | WO2012/170930 | 12/2012 |
| WO | WO2013/039857 | 3/2013 |
| WO | WO2013/039861 | 3/2013 |
| WO | WO2013/090186 A1 | 6/2013 |
| WO | WO2013/101690 | 7/2013 |
| WO | WO2013/126803 | 8/2013 |
| WO | WO2013/130161 | 9/2013 |
| WO | WO2013/151663 | 10/2013 |
| WO | WO2013/151664 | 10/2013 |
| WO | WO2013/151666 | 10/2013 |
| WO | WO2013/151667 | 10/2013 |
| WO | WO2013/151668 | 10/2013 |
| WO | WO2013/151670 | 10/2013 |
| WO | WO2013/151671 | 10/2013 |
| WO | WO2013/151672 | 10/2013 |
| WO | WO2013/151736 | 10/2013 |
| WO | WO2013/185069 A1 | 12/2013 |
| WO | WO2014/113089 | 7/2014 |
| WO | WO2014/144039 | 9/2014 |
| WO | WO2014/144711 | 9/2014 |
| WO | WO2014/144767 | 9/2014 |
| WO | WO2014/152027 | 9/2014 |
| WO | WO2014/152030 | 9/2014 |
| WO | WO2014/152031 | 9/2014 |
| WO | WO2014/152211 | 9/2014 |
| WO | WO2014/152540 | 9/2014 |
| WO | WO2014/158795 | 10/2014 |
| WO | WO2014/159813 | 10/2014 |
| WO | WO2015/006747 A2 | 1/2015 |
| WO | WO2015/048744 | 4/2015 |
| WO | WO2015/051169 | 4/2015 |
| WO | WO2015/051173 | 4/2015 |
| WO | WO2015/058069 | 4/2015 |
| WO | WO2015/085318 | 6/2015 |
| WO | WO2015/089511 | 6/2015 |
| WO | WO2015/011633 | 1/2016 |
| WO | WO2016/054421 | 4/2016 |
| WO | WO2016/071857 | 5/2016 |
| WO | WO2016/077123 | 5/2016 |
| WO | WO2016/077125 | 5/2016 |
| WO | WO2016/118724 | 7/2016 |
| WO | WO2016/118725 | 7/2016 |
| WO | WO2016/154127 | 9/2016 |
| WO | WO2016/164762 | 10/2016 |
| WO | WO2016/183366 A2 | 11/2016 |
| WO | WO2016/197132 A1 | 12/2016 |
| WO | WO2016/197133 A1 | 12/2016 |
| WO | WO2016/201377 A1 | 12/2016 |
| WO | WO2017/019891 A2 | 2/2017 |
| WO | WO2017/049074 A1 | 3/2017 |
| WO | WO2017/049275 A2 | 3/2017 |
| WO | WO2017/049286 A1 | 3/2017 |
| WO | WO2017/102010 A1 | 6/2017 |
| WO | WO2017/103088 A1 | 6/2017 |
| WO | WO2017/108087 A1 | 6/2017 |
| WO | WO2017/109134 A1 | 6/2017 |
| WO | WO2017/109161 A1 | 6/2017 |

OTHER PUBLICATIONS

Su, Xingfang et al., "Cytosolic Delivery Mediated via Electrostatic Surface Binding of mRNA to Degradable Lipid-Coated Polymeric Nanoparticles", 240th National Meeting of the American-Chemical Society, Polymer Reprints, 2010, vol. 51, No. 2, pp. 668-669.

Wang, Yuhua et al., "Systemic delivery of modified mRNA encoding herpes simplex virus 1 thymidine kinase for targeted cancer gene therapy", Molecular Therapy, Nature Publishing Group, GB, Feb. 2013, vol. 21, No. 2, pp. 358-367.

* cited by examiner

SEQUENCE LISTING

<160> NUMBER OF SEQ ID NOS: 7

<210> SEQ ID NO 1
<211> LENGTH: 1653
<212> TYPE: RNA
<213> ORGANISM: Artificial Sequence
<220> FEATURE:
<223> OTHER INFORMATION: chemically synthesized nucleotide

<400> SEQUENCE: 1

```
auggaagaug ccaaaaacau uaagaagggc ccagcgccau ucuacccacu cgaagacggg      60
accgccggcg agcagcugca caaagccaug aagcgcuacg cccuggugcc cggcaccauc     120
gccuuuaccg acgcacauau cgagguggac auuaccuacg ccgaguacuu cgagaugagc     180
guucggcugg cagaagcuau gaagcgcuau gggcugaaua caaaccaucg gaucguggug     240
ugcagcgaga auagcuugca guucuucaug cccguuugg gugcccuguu caucggugug     300
gcuguggccc cagcuaacga caucuacaac gagcgcgagc ugcugaacag caugggcauc     360
agccagccca ccgucguauu cgugagcaag aaagggcugc aaaagauccu caacgugcaa     420
aagaagcuac cgaucauaca aaagaucauc aucauggaua gcaagaccga cuaccagggc     480
uuccaaagca uguacaccuu cgugacuucc cauuugccac ccggcuucaa cgaguacgac     540
uucgugcccg agagcuucga ccgggacaaa accaucgccc ugaucaugaa caguaguggc     600
aguaccggau ugcccaaggg cguagcccua ccgcaccgca ccgcuugugu ccgauucagu     660
caugcccgcg accccaucuu cggcaaccag aucaucccgc acaccgcuau ccucagcgug     720
gugccauuuc accacggcuu cggcaauguuc accacgcugg gcuacuugau cugcggcuuu     780
```

```
cgggucgugc ucauguaccg cuucgaggag gagcuauucu ugcgcagcuu gcaagacuau      840
aagauucaau cugcccugcu ggugcccaca cuauuuagcu ucuucgcuaa gagcacucuc      900
aucgacaagu acgaccuaag caacuugcac gagaucgcca gcggcggggc gccgcucagc      960
aaggagguag gugaggccgu ggccaaacgc uuccaccuac caggcauccg ccagggcuac     1020
ggccugacag aaacaaccag cgccauucug aucaccccg aagggacga caagccuggc      1080 gcaguaggca aggugugcc cuucuucgag gcuaaggugg uggacuugga caccgguaag     1140 acacuggug ugaaccagcg cggcgagcug ugcguccgug gccccaugau caugagcggc     1200
uacguuaaca ccccgaggc uacaaacgcu cucaucgaca aggacggcug gcugcacagc     1260
ggcgacaucg ccuacuggga cgaggacgag cacuucuuca ucguggaccg gcugaagagc     1320
cugaucaaau acaagggcua ccagguagcc cagccgaac uggagagcau ccugcugcaa     1380 cacccaaca ucuucgacgc cggggucgcc ggccugcccg acgacgaugc cggcgagcug     1440
cccgccgcag ucgucgugcu ggaacacggu aaaaccauga ccgagaagga gaucguggac     1500
uauguggcca gccagguuac aaccgccaag aagcugcgcg gugguguugu uucguggac     1560 gaggugccua aggacugac cggcaaguug gacgcccgca agauccgcga gauucucauu     1620
aaggccaaga agggcggcaa gaucgccgug uaa                                 1653

<210> SEQ ID NO 2
<211> LENGTH: 1140
<212> TYPE: RNA
<213> ORGANISM: Artificial Sequence
<220> FEATURE:
<223> OTHER INFORMATION: chemically synthesized nucleotide

<400> SEQUENCE: 2
augucgcgca guggaaccga uccucagcaa cgccagcagg cgucagaggc ggacgccgca       60
gcagcaaccu uccgggcaaa cgaccaucag cauauccgcu acaacccgcu gcaggaugag      120
ugggugcugg ugucagcuca ccgcaugaag cggcccuggc agggucaagu ggagcccag      180 cuucugaaga cagugcccg ccaugacccu cucaacccuc ugugccugg gccauccga       240 gccaacggag aggugaaucc ccaguacgau agcaccuucc guuugacaa cgacuuccca      300 gcucugcagc cugaugcccc caguccagga cccagugauc aucccuuuuu ccaagcaaag     360
ucugcucgag gagucuguaa ggucaugugc uccacccu ggcggaugu aacgcugcca      420 cucaugucgg ucccugagau ccgggcuguu guugaugcau gggccucagu cacagaggag     480
cugggugccc aguacccuug ggugcagauc uuugaaaaca aggugccau gaugggcugu     540 ucuaaccccc accccacug ccagguaugg gccagcaguu ccugccaga uauugcccag      600 cgugaggagc gaucucagca ggccuauaag agucagcaug agagcccu gcuaauggag     660 uacagccgcc aggagcuacu caggaaggaa cgucuggucc uaaccaguga gcacugguua      720
guacuggucc ccuucgggc aacauggccc uaccagacac ugcugcugcc ccgucggcau      780
gugcggcggc uaccugagcu gaccccugcu gagcgugaug aucuagccuc caucaugaag     840
aagcucuuga ccaaguauga caaccucuuu gagacguccu ucccuacuc caugggcugg      900 caugggcuc ccacaggauc agaggcuggg gccaacugga accauggca gcugcacgcu      960 cauuacuacc cuccgcuccu gcgcucugcc acuguccgga aauucaugu uggcuacgaa     1020 augcuugcuc aggcucagag ggaccucacc ccugagcagg cugcagagag acuaagggca     1080
cuuccugagg uucauuacca ccuggggcag aaggacaggg agacagcaac caucgccuga     1140
```

<210> SEQ ID NO 3
<211> LENGTH: 582
<212> TYPE: RNA
<213> ORGANISM: Artificial Sequence
<220> FEATURE:
<223> OTHER INFORMATION: chemically synthesized nucleotide

<400> SEQUENCE: 3

```
auggggguge acgaaugucc ugccuggcug uggcuucucc ugucccugcu gucgcucccu    60
cugggccucc caguccuggg cgccccacca cgccucaucu gugacagccg aguccuggag   120
agguaccucu uggaggccaa ggaggccgag aauaucacga cgggcugugc ugaacacugc   180
agcuugaaug agaauaucac ugucccagac accaaaguua auuucuaugc cuggaagagg   240
auggaggucg ggcagcaggc cguagaaguc uggcagggcc uggcccugcu gucggaagcu   300
guccugcggg gccaggcccu guuggucaac ucuucccagc cgugggagcc ccugcagcug   360
caugggaua aagccgucag uggccuucgc agccucacca cucugcuucg ggcucuggga   420
gcccagaagg aagccaucuc cccuccagau gcggccucag cugcuccacu ccgaacaauc   480
acugcugaca cuuccgcaa acucuuccga gucuacucca auuccuccg gggaaagcug    540
aagcuguaca caggggaggc cugcaggaca ggggacagau ga                     582
```

<210> SEQ ID NO 4
<211> LENGTH: 11
<212> TYPE: RNA
<213> ORGANISM: Artificial Sequence
<220> FEATURE:
<223> OTHER INFORMATION: chemically synthesized nucleotide

<400> SEQUENCE: 4

```
gggauccuac c                                                         11
```

<210> SEQ ID NO 5
<211> LENGTH: 140
<212> TYPE: RNA
<213> ORGANISM: Artificial Sequence
<220> FEATURE:
<223> OTHER INFORMATION: chemically synthesized nucleotide

<400> SEQUENCE: 5

```
ggacagaucg ccuggagacg ccauccacgc uguuugacc uccauagaag acaccgggac     60
cgauccagcc uccgcggccg ggaacggugc auuggaacgc ggauuccccg ugccaagagu   120
gacucaccgu ccuugacacg                                               140
```

<210> SEQ ID NO 6
<211> LENGTH: 8
<212> TYPE: RNA
<213> ORGANISM: Artificial Sequence
<220> FEATURE:
<223> OTHER INFORMATION: chemically synthesized nucleotide

<400> SEQUENCE: 6

```
uuugaauu                                                             8
```

<210> SEQ ID NO 7
<211> LENGTH: 100
<212> TYPE: RNA
<213> ORGANISM: Artificial Sequence
<220> FEATURE:
<223> OTHER INFORMATION: chemically synthesized nucleotide

<400> SEQUENCE: 7

```
cggguggcau cccugugacc ccucccagu gccucuccug gcccuggaag uugccacucc    60
agugcccacc agccuuggcc uaauaaaauu aaguugcauc                       100
```

SYNERGISTIC ENHANCEMENT OF THE DELIVERY OF NUCLEIC ACIDS VIA BLENDED FORMULATIONS

RELATED APPLICATIONS

This application is a Continuation of the U.S. application Ser. No. 14/775,818, filed on Sep. 14, 2015, which is a National Stage Entry of the International Application PCT/US2014/028498, filed on Mar. 14, 2014, which claims Priority from Provisional Application 61/789,375, filed on Mar. 15, 2013, the disclosure of which are hereby incorporated in their entirety by reference.

INCORPORATION-BY-REFERENCE OF SEQUENCE LISTING

This instant application contains a Sequence Listing which has been submitted electronically in ASCII format and is hereby incorporated by reference in its entirety. Said ASCII copy, created on Mar. 28, 2019, is named MRT-1101US2_SL.txt and is 6,270 bytes in size.

BACKGROUND

The efficient delivery of nucleic acids to targeted cells and tissues, as well as the subsequent transfection of such nucleic acids into such targeted cells and tissues remains a technical challenge. For example, as a result of the size and charge of nucleic acids such as DNA and RNA, the ability to effectively and efficiently deliver such nucleic acids to and/or to transfect such targeted cells and tissues is often limited.

One approach to improve the delivery of nucleic acids and polynucleotides to target cells and tissues has been the liposomal encapsulation of nucleic acid in lipids, and in particular cationic lipids. The electrostatic interaction of the cationic lipid with nucleic acids facilitates the formation of lipid-encapsulated nucleic acid particles in size ranges which may be suitable for in vivo administration. The positively charged cationic lipid on the outer particle surfaces facilitates the interaction of the cationic lipid-based liposome with the negatively-charged cellular membranes, thereby promoting fusion of the liposome with the cellular membrane and delivering the liposome and/or emptying the nucleic acid contents of the liposome intracellularly. Although several advantages of using liposomes to facilitate the delivery of therapeutic agents to target cells and tissues have been previously described, many problems still exist in in vivo, ex vivo and in vitro applications. For example, many of the cationic lipids are generally toxic to the targeted cells, and accordingly may be of limited use. Furthermore, liposomal carriers may not be the most efficient means of delivering nucleic acids to target cells or to subsequently transfect such cells.

Novel approaches and therapies are still needed to enhance the delivery and/or transfection efficiencies of polynucleotides and nucleic acids, particularly those delivered in liposome delivery vehicles, such as encapsulated liposomal formulations. The development of new and improved liposome delivery vehicles and liposomal formulations that demonstrate enhanced delivery and/or transfection efficiencies would further advance nucleic acid based therapies for the treatment of diseases, such as gene and mRNA silencing therapies, that may benefit from gene replacement therapies, mRNA delivery therapies, and/or other therapies that include the intracellular delivery of nucleic acids for the modulation of gene, protein and/or enzyme expression.

SUMMARY

The present invention is, in part, based on the unexpected discovery that a blend of multiple non-identical lipid nanoparticles synergistically enhances the expression of messenger RNA (mRNA) encapsulated within at least one of the lipid nanoparticles in vivo. This synergistic effect is observed across a wide variety of different lipid nanoparticles blended in various ratios and via different administration routes. For example, in some cases, enhancements in protein expression (e.g., evidenced by light output of a firefly luciferase) ranged from about 1.5-fold to 30-fold increase as compared to the additive total based on each individual nanoparticle. The synergy is also observed in both tissue specific and systemic expression of mRNA. More surprisingly, this synergistic effect is not nucleic acid specific. For example, a non-fluorescent mRNA can synergistically enhances the light production of a fluorescent mRNA. It is contemplated that this unexpected discovery of synergistic enhancement between different lipid formulations has significant implication in messenger RNA therapy because it allows equivalent therapeutic efficacy be achieved via administration of a significantly lower dose. The ability to create a synergistic production of protein via lipid-based nanoparticle delivery of mRNA also permits a much greater therapeutic window for the treatment of a host of diseases and achieves equal or greater efficacy while minimizing any adverse or toxic event. Thus, the present invention provides a safer and more potent messenger RNA therapy for various diseases.

Among other things, disclosed herein are pharmaceutical compositions that comprise a blend of at least two lipid nanoparticles (e.g., a blend of a first lipid nanoparticle and a second lipid nanoparticle) and related methods of using such blended nanoparticle compositions. In certain embodiments, at least one of the constituent lipid nanoparticles that comprises the blended lipid nanoparticle composition comprises (e.g., encapsulates) one or more polynucleotides (e.g., mRNA). The blended lipid nanoparticle compositions described herein are characterized as being able to efficiently deliver the encapsulated polynucleotides to target cells, and are also characterized by their ability to improve the subsequent transfection of such encapsulated polynucleotides following contacting one or more of such target cells. The blended lipid nanoparticle compositions are also characterized by their ability to modulate or enhance (e.g., synergistically increase) the expression of the polynucleotides encapsulated therein by target cells. In certain embodiments where the polynucleotides are mRNA, the blended lipid nanoparticle compositions are also characterized by their ability to enhance the production of polypeptides encoded by such polynucleotides.

As used herein, the term "blend", "blended", or grammatical equivalent, refers to a combination of two or more separate, non-identical formulations. Typically, the two or more separate, non-identical formulations are combined or blended into one composition, such as, a suspension, as depicted, for example, in FIG. 1. As used herein, non-identical formulations refer to formulations containing at least one distinct lipid component. In some embodiments, non-identical formulations suitable for blend contain at least one distinct cationic lipid component. The term "blend" as used herein is distinguishable from the terms "mix" or "mixture", which are used herein to define a single formulation containing multiple non-identical cationic/ionizable lipids, multiple non-identical helper lipids, and/or multiple non-identical PEGylated lipids. In some embodiments, a "mix" formulation contains at least two or more non-identical cationic/ionizable lipids. Typically, a "mix" formulation contains a single homogenous population of lipid nanoparticles.

Certain embodiments relate to methods of expressing one or more polynucleotides in one or more target cells. For example, where the polynucleotides are mRNA encoding a functional protein, provided herein are methods of enhancing the production and/or excretion of polypeptides encoded by such polynucleotides by a target cell. Certain embodiments relate to methods of modulating the expression of one or more polynucleotides or nucleic acids (e.g., a target nucleic acid) in one or more target cells, using for example an antisense oligonucleotide. Such methods may comprise contacting the one or more target cells with a pharmaceutical composition comprising a blend of at least two lipid nanoparticles (e.g., a first lipid nanoparticle and a second lipid nanoparticle), wherein such first and second lipid nanoparticles have different lipid compositions (e.g., the first lipid composition comprises a different cationic lipid than the second lipid composition). In certain embodiments, at least one of the two or more lipid nanoparticles that comprise the blended lipid nanoparticle composition comprises one or more polynucleotides. For example, the first lipid nanoparticle may encapsulate one or more polynucleotides and the second lipid nanoparticle may optionally encapsulate one or more polynucleotides.

In certain embodiments, the blended first lipid nanoparticle and second lipid nanoparticle comprise the same one or more polynucleotides, wherein the expression of the one or more polynucleotides by the target cells following the administration (e.g., intravenously) of the blended pharmaceutical composition to a subject exceeds the relative sum of the expression of the one or more polynucleotides achieved by the first lipid nanoparticle and the expression of the one or more polynucleotides achieved by the second lipid nanoparticle when the first lipid nanoparticle and the second lipid nanoparticle are administered to the subject independently of each other. For example, in certain embodiments, the expression of the one or more polynucleotides by the target cells following the administration (e.g., intravenously) of such blended pharmaceutical composition to a subject may exceed the relative sum of the expression of the one or more polynucleotides achieved by the first lipid nanoparticle and the expression of the one or more polynucleotides achieved by the second lipid nanoparticle when the first lipid nanoparticle and the second lipid nanoparticle are independently administered to the subject by at least about two-, five-, ten-, twelve-, fifteen-, twenty-, twenty-five-, thirty-, forty-, fifty-fold, or more.

In certain embodiments, the blended first lipid nanoparticle and second lipid nanoparticle comprise the same one or more polynucleotides (e.g., mRNA), wherein the production of one or more polypeptides or proteins (e.g., an enzyme) by the target cells following the administration (e.g., intravenously) of the blended pharmaceutical composition to a subject exceeds the relative sum of the production of the one or more polypeptides or proteins (e.g., an enzyme) produced following the delivery of such one or more polynucleotides achieved by the first lipid nanoparticle and the one or more polypeptides produced following the delivery of the one or more polynucleotides achieved by the second lipid nanoparticle when the first lipid nanoparticle and the second lipid nanoparticle are administered to the subject independently of each other. For example, in certain embodiments where the polynucleotides comprise mRNA, the polypeptides produced following the delivery of such polynucleotides to the target cells following the administration (e.g., intravenously) of such blended pharmaceutical composition to a subject may exceed the relative sum of the polypeptides produced following the delivery of such polynucleotides achieved by the first lipid nanoparticle and the polypeptides produced following the delivery of such polynucleotides achieved by the second lipid nanoparticle when the first lipid nanoparticle and the second lipid nanoparticle are independently administered to the subject by at least about two-, five-, ten-, twelve-, fifteen-, twenty-, twenty-five-, thirty-, forty-, fifty-, sixty-, seventy-, eighty-, ninety-, one-hundred-, five-hundred-, one thousand-fold, or more.

In another embodiment, only one of the two or more lipid nanoparticles that comprise the blended composition comprises or encapsulates a polynucleotide. For example, where the pharmaceutical compositions comprises two blended lipid nanoparticles, only the first lipid nanoparticle comprises one or more polynucleotides while the second lipid nanoparticle does not comprise a polynucleotide (i.e., the second polynucleotide is empty). In such an embodiment, following the administration (e.g., intravenously) of the two blended first and second lipid nanoparticles that comprise the pharmaceutical composition to the subject, the production of one or more polypeptides or proteins encoded by the encapsulated polynucleotides by a target cell is enhanced relative to the production of one or more polypeptides or proteins observed when the first lipid nanoparticle is administered to the subject independently of the second lipid nanoparticle. For example, in such an embodiment, the production of the one or more polypeptides or proteins by the target cells following the administration of such blended pharmaceutical composition to a subject exceeds the production of the one or more polypeptides or proteins when the first lipid nanoparticle is administered to the subject independently of the second lipid nanoparticle by at least about two-, five-, ten-, twelve-, fifteen- or twenty-fold, twenty-five-, thirty-, forty-, fifty-, one-hundred-, five-hundred-, one thousand-fold or more.

Upon contacting one or more targeted cells with the blended lipid nanoparticle compositions disclosed herein (e.g., by intravenously administering the blended pharmaceutical composition to a subject) one or more of such target cells are transfected with and may express the one or more polynucleotides and/or enhance the production of one or more functional polypeptides or proteins encoded by such one or more polynucleotides. In certain embodiments, contacting such target cells with the blended lipid nanoparticles and pharmaceutical compositions such that the target cells are transfected by the encapsulated one or more polynucleotides enhances (e.g., synergistically increases) the expression of such polynucleotides and/or increases the production of a functional protein or polypeptide product that may be useful in the treatment of a disease or pathological condition (e.g., diseases resulting from a protein or enzyme deficiency). In certain embodiments, upon or following transfection by the blended lipid nanoparticle compositions described herein, the expression of the encapsulated polynucleotides and/or production of a functional polypeptide or protein by one or more target cells is synergistically increased, and in particular is synergistically increased relative to the expression of the polynucleotides and/or production of a the functional polypeptide or protein that is observed when the constituent lipid nanoparticles that comprise the blended composition (e.g., the first lipid nanoparticle and the second lipid nanoparticle) are administered independently of the other. The expression of the encapsulated polynucleotides that comprise the blended composition (and/or where such polynucleotides comprise mRNA, the production of the polypeptides encoded by such encapsulated polynucleotides) may be increased, for example, by at least about two-, three-, four-, five-, six-, eight-, ten-, twelve-, fifteen-, twenty-, twenty-five-, thirty-, forty- or fifty-fold, or more relative to the expression of polynucleotide (and/or the production of polypeptide where such polynucleotide comprises mRNA) that is observed when the constituent lipid nanoparticles that comprise the blended formulation are independently administered.

Also disclosed herein are methods of modulating or increasing the expression of one or more polynucleotides and methods of increasing the production of one or more functional polypeptides or proteins in one or more target cells (e.g., target cells of a subject to whom the blended lipid nanoparticle compositions are administered). Such methods may comprise the step of administering or otherwise contacting targeted cells or tissues with a pharmaceutical composition that comprises a blend of at least a first lipid nanoparticle and a second lipid nanoparticle, wherein the first lipid nanoparticle comprises one or more polynucleotides. Following the administration or otherwise contacting targeted cells or tissues with the blended lipid nanoparticle compositions one or more target cells are transfected with the one or more polynucleotides encapsulated in one or more of the constituent lipid nanoparticles, such that expression of the one or more polynucleotides and/or production of one or more functional polypeptides or proteins is increased or synergistically increased relative to the expression of the one or more polynucleotides or production of one or more functional polypeptides or proteins when the first lipid nanoparticle is administered independently of the second lipid nanoparticle. In certain embodiments, the expression of the encapsulated polynucleotides that comprise the blended composition may be increased, for example, by at least about two-, four-, five-, ten-, twelve-, fifteen-, twenty-, or twenty-five-, fifty-, seventy-five, one-hundred, two-hundred-, five-hundred-, one thousand-fold, or more relative to the expression observed when the constituent lipid nanoparticles that comprise the blended formulation are independently administered.

Also disclosed herein are pharmaceutical compositions that comprise a blend of a first lipid nanoparticle and a second lipid nanoparticle, wherein the first lipid nanoparticle comprises one or more polynucleotides. In certain embodiments both the first and the second lipid nanoparticles comprise or encapsulate the same or a different polynucleotide. Upon contacting one or more target cells with the pharmaceutical composition the one or more polynucleotides encapsulated by the constituent lipid nanoparticles transfect the target cells and are expressed, and where such polynucleotides comprise mRNA, thereby produce a functional polypeptide or protein. In certain embodiments, the expression of the one or more polynucleotides by the target cells exceeds the relative sum of the expression of the one or more polynucleotides achieved by the first lipid nanoparticle and the second lipid nanoparticle that comprise the pharmaceutical composition when the target cells are contacted with the first lipid nanoparticle and second lipid nanoparticle independently of the other. In other embodiments, the production of one or more functional polypeptides by target cells exceeds the relative sum of the production of one or more functional polypeptides achieved by the first lipid nanoparticle and the second lipid nanoparticle that comprise the pharmaceutical composition when the target cells are contacted with the first lipid nanoparticle and the second lipid nanoparticle independently of the other.

In certain embodiments, the first lipid nanoparticle or the second lipid nanoparticle comprises one or more cationic lipids. For example, one or both of the first and second lipid nanoparticles may include one or more of C12-200, DOTAP (1,2-dioleyl-3-trimethylammonium propane), DODAP (1,2-dioleyl-3-dimethylammonium propane), DOTMA (1,2-di-O-octadecenyl-3-trimethylammonium propane), DLinDMA, DLin-KC2-DMA, HGT4003 and ICE.

In certain embodiments, the first lipid nanoparticle or the second lipid nanoparticle comprise one or more helper lipids. For example, one or both of the first and second lipid nanoparticles that comprise the blended pharmaceutical compositions may include one or more of helper lipids that are selected from the group consisting of DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DPPE (1,2-dipalmitoyl-sn-glycero-3-phosphoethanolamine), DMPE (1,2-dimyristoyl-sn-glycero-3-phosphoethanolamine), DOPG (,2-dioleoyl-sn-glycero-3-phospho-(1'-rac-glycerol)) and cholesterol.

Similarly, in certain embodiments, the first lipid nanoparticle or the second lipid nanoparticle may comprise one or more PEG-modified lipids. For example, one or both of the first and second lipid nanoparticles may comprise one or more of PEG-modified lipids that comprise a poly(ethylene) glycol chain of up to 5 kDa in length covalently attached to a lipid comprising one or more alkyl chains of $C_6$-$C_{20}$ in length.

In certain embodiments, one or more of the at least two lipid nanoparticles that comprise the blended compositions of the invention are prepared by combining or comprise multiple lipid, non-lipid and/or polymer components. For example, the first lipid nanoparticle or the second lipid nanoparticle may comprise DLinDMA, CHOL, DOPE and DMG-PEG-2000. In some embodiments, the first lipid nanoparticle or the second lipid nanoparticle comprises C12-200, CHOL, DOPE and DMG-PEG-2000. In some embodiments, the first lipid nanoparticle or the second lipid nanoparticle comprises DLinKC2, CHOL, DOPE and DMG-PEG-2000. Similarly, one or more of the first lipid nanoparticle and the second lipid nanoparticle may comprise one or more lipids selected from the group consisting of ICE, DSPC, CHOL, DODAP, DOTAP and C8-PEG-2000. In another embodiment, the first lipid nanoparticle or the second lipid nanoparticle comprises ICE, DOPE and DMG-PEG-2000. Still in another embodiment, the first lipid nanoparticle or the second lipid nanoparticle comprises HGT4003, DOPE, CHOL and DMG-PEG-2000.

In certain embodiments, the lipid compositions of the two or more blended lipid nanoparticles are different (e.g., have different lipid compositions). For example, contemplated hereby are blended compositions wherein the first lipid nanoparticle comprises a cationic lipid, and wherein the second lipid nanoparticle comprises a cationic lipid which is different from the cationic lipid which comprises the first lipid nanoparticle Also disclosed herein are methods of enhancing or otherwise increasing (e.g., synergistically increasing) the delivery or the rate of delivery of one or more polynucleotides to one or more target cells, as well as methods of enhancing the residence time of one or more polynucleotides within a target cell. Such methods generally comprise contacting the one or more target cells with a pharmaceutical composition comprising a blend of at least two lipid nanoparticles, each having a different lipid composition, such that the delivery of the polynucleotides (e.g., to one or more target cells, tissues or organs) is enhanced. Upon delivery of such one or more polynucleotides (e.g., one or more antisense oligonucleotides) to or into the target cells, such polynucleotide may exert its intended function (e.g., modulate the expression of a target nucleic acid such as mRNA). For example, an antisense oligonucleotide may modulate or decrease (e.g., synergistically decrease) the expression of a targeted gene or nucleic acid. Alternatively, in certain embodiments, following delivery of the polynucleotides to the target cells the production of a functional peptide or protein encoded by such polynucleotide is increased or synergistically increased.

The blended compositions and methods of use described herein may be formulated to specifically target and transfect one or more target cells, tissues and organs. For example, contemplated target cells may comprise one or more cells selected from the group consisting of hepatocytes, epithelial cells, hematopoietic cells, epithelial cells, endothelial cells, lung cells, bone cells, stem cells, mesenchymal cells, neural cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes and tumor cells.

In certain embodiments, the blended lipid nanoparticle compositions and methods of using such blended compositions comprise one or more polynucleotides (e.g., mRNA). Such polynucleotides may encode, for example, a functional polypeptide, protein or enzyme, and upon being expressed (e.g., translated) by one or more target cells a functional polypeptide product (e.g., a protein or enzyme) is produced, and in some instances secreted by the target cell into the peripheral circulation. In certain embodiments, the one or more of the polynucleotides that comprise or are otherwise encapsulated by one or more of the constituent lipid nanoparticles that comprise the blended compositions encode a polypeptide which is aberrantly expressed by the subject. In certain embodiments, the one or more of the encapsulated polynucleotides that comprise the blended lipid nanoparticle formulations encode a functional enzyme such as a urea cycle enzyme (e.g., ornithine transcarbamylase (OTC), carbamoyl-phosphate synthetase 1 (CPS1), argininosuccinate synthetase (ASS1), argininosuccinate lyase (ASL) or arginase 1 (ARG1)). In certain embodiments the one or more of the encapsulated polynucleotides comprises mRNA encoding an enzyme associated with a lysosomal storage disorder (e.g., the encapsulated polynucleotide is mRNA encoding one or more of the enzymes agalsidase alfa, alpha-L-iduronidase, iduronate-2-sulfatase, N-acetylglucosamine-1-phosphate transferase, N-acetylglucosaminidase, alpha-glucosaminide acetyltransferase, N-acetylglucosamine 6-sulfatase, N-acetylgalactosamine-4-sulfatase, beta-glucosidase, galactose-6-sulfate sulfatase, beta-galactosidase, beta-glucuronidase, glucocerebrosidase, heparan sulfamidase, hyaluronidase and galactocerebrosidase). Alternatively, in some embodiments, one or more of the encapsulated polynucleotides that comprise the blended lipid nanoparticle formulations comprises SEQ ID NO: 2 or SEQ ID NO: 3.

The use of mRNA as the polynucleotide are also contemplated hereby and in particular the use of mRNA that comprises one or more chemical modifications. In certain embodiment, such chemical modifications render the mRNA more stable and may comprise, for example an end blocking modification of a 5' or 3' untranslated region of the mRNA. In certain embodiments, the chemical modification comprises the inclusion of a partial sequence of a CMV immediate-early 1 (IE1) gene to the 5' untranslated region of the mRNA. In other embodiments the chemical modification comprises the inclusion of a poly A tail to the 3' untranslated region of the mRNA. Also contemplated are chemical modifications that comprise the inclusion of a Cap1 structure to the 5' untranslated region of the mRNA. In still other embodiments, the chemical modification comprises the inclusion of a sequence encoding human growth hormone (hGH) to the 3' untranslated region of the mRNA.

Also disclosed herein are methods of manipulating the enhanced (e.g., synergistically increased) expression of the one or more polynucleotides that are encapsulated in the one or more of the first or second lipid nanoparticles that comprise the blended compositions and methods of manipulating the enhanced production of the polypeptides encoded by such encapsulated one or more polynucleotides. For example, in certain embodiments the relative ratio of the first and second lipid nanoparticles may be adjusted (e.g., based on the mass of the encapsulated polynucleotides) to enhance expression of one or more of the encapsulated polynucleotides and/or to enhance the production of the one or more polypeptides encapsulated by such encapsulated polynucleotides. In some embodiments, the ratio of the one or more polynucleotides comprising the first lipid nanoparticle to the one or more polynucleotides comprising the second lipid nanoparticle in the pharmaceutical composition is about 1:1, 2:1, 3:1, 4:1, 5:1, 6:1, 7:1, 8:1, 9:1, 10:1, 11:1, 12:1, 15:1, 20:1, 25:1, 30:1, 40:1, 50:1, 60:1, 75:1, 100:1, 125:1, 1:2, 1:3, 1:4, 1:5, 1:6, 1:7, 1:8, 1:9, 1:10, 1:11, 1:12, 1:15, 1:20, 1:25, 1:30, 1:40, 1:50, 1:60, 1:75, 1:100, 1:125 or more. Similarly, the enhanced (e.g., synergistically increased) expression of the one or more polynucleotides that are encapsulated in the one or more of the first or second lipid nanoparticles that comprise the blended compositions may be manipulated by varying the content and relative concentrations of one or more of the lipids, non-lipids, helper lipids and PEG-modified lipids that comprise such lipid nanoparticles. Furthermore, the enhanced (e.g., synergistically increased) production by target cells of one or more functional polypeptides or proteins encoded by encapsulated polynucleotides in the first or second lipid nanoparticles that comprise the blended compositions may be manipulated by varying the content and relative concentrations of one or more of the lipids, non-lipids, helper lipids and PEG-modified lipids that comprise such lipid nanoparticles.

The synergistic enhancements in expression of encapsulated polynucleotides that characterize the blended lipid nanoparticle formulations of the present invention and/or the synergistic production of polypeptides encoded thereby by one or more target cells allow therapeutically effective concentrations of produced polynucleotides (e.g., a therapeutic protein or enzyme) to be achieved in the targeted tissues (or serum if the polypeptide product is excreted by target cell) using a significantly lower dose of polynucleotide than was previously anticipated. Accordingly, in certain embodiments, the effective amount of a polynucleotide required to achieve a desired therapeutic effect may be reduced by encapsulating such polynucleotide in one or more lipid nanoparticles and blending at least two lipid nanoparticles. Such methods comprise a step of administering a pharmaceutical composition to the subject, wherein the pharmaceutical composition comprises a first lipid nanoparticle blended with a second lipid nanoparticle, and wherein one or both of the first lipid nanoparticle and the second lipid nanoparticle comprise the polynucleotide, followed by the transfection of one or more target cells of the subject with such polynucleotides, such that the amount of the polynucleotide required to effectuate a therapeutic effect is reduced (e.g., reduced relative to the amount of polynucleotide required to effectuate a therapeutic effect using a non-blended composition or other standard techniques). In certain embodiments, the amount of a polynucleotide required to effectuate a therapeutic effect is reduced by at least about 10%, 15%, 20%, 25%, 30%, 40%, 50%, 60%, 75%, 80%, 90%, 95%, or 99% relative to the amount of polynucleotide required to effectuate a therapeutic effect using a non-blended composition or other standard techniques). In certain embodiments, the amount of a polynucleotide required to effectuate a therapeutic effect is reduced by at least two-, three-, four-, five-, six-, seven-, ten-, twelve-, fifteen-, twenty-, twenty-five-, thirty-, forty- or fifty-fold or more relative to the amount of polynucleotide required to effectuate a therapeutic effect using a non-blended composition or other standard techniques).

The above discussed and many other features and attendant advantages of the present invention will become better understood by reference to the following detailed description of the invention when taken in conjunction with the accompanying examples. The various embodiments described herein are complimentary and can be combined or used together in a manner understood by the skilled person in view of the teachings contained herein.

BRIEF DESCRIPTION OF THE DRAWINGS

As illustrated in FIG. 8, all formulations demonstrated successful human EPO secretion by the targeted cells. Each blended formulation demonstrated a synergistic enhancement of protein production. The doses are represented in FIG. 8 (in parentheses) as micrograms of encapsulated human EPO mRNA.

DETAILED DESCRIPTION

Figure 1:
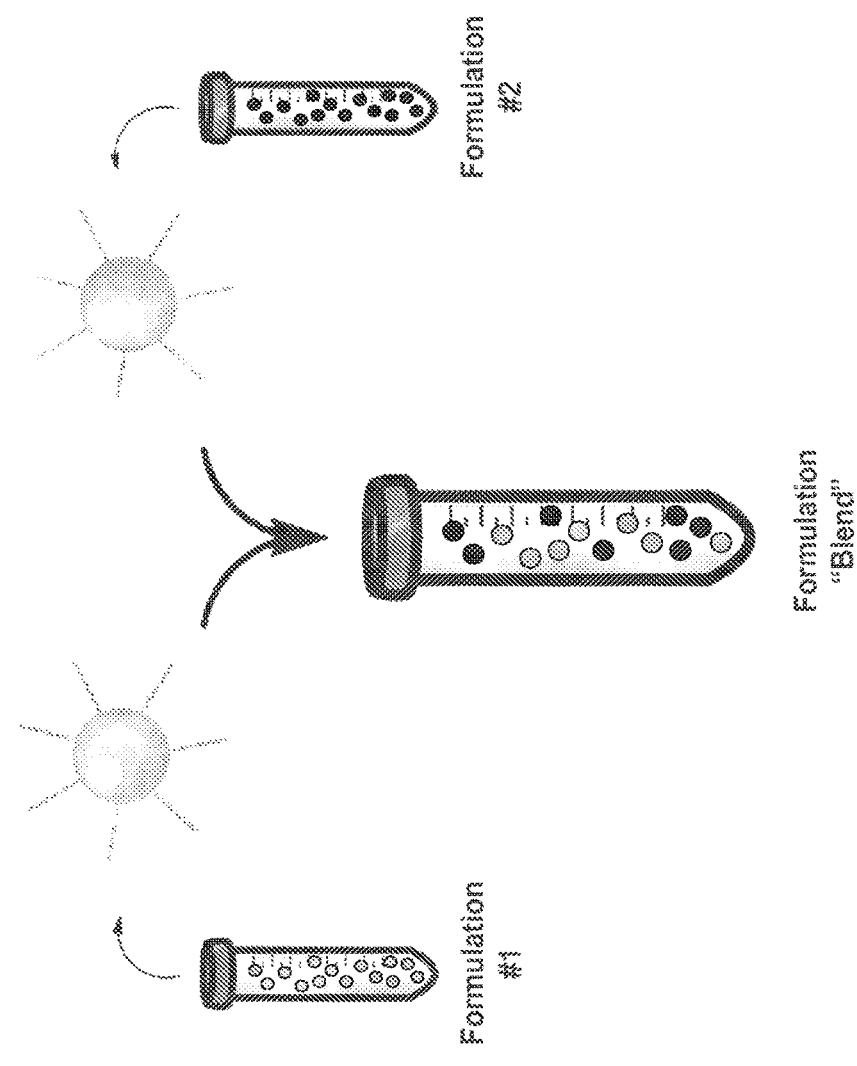
FIG. 1. is a schematic representing a formulation "blend", which is generally defined as a combination of two or more separate, non-identical formulations into one.

Disclosed herein are pharmaceutical compositions which comprise a blend of at least two lipid nanoparticles, at least one of which comprises a polynucleotide and to related methods of using such pharmaceutical compositions as a highly efficient means of increasing the expression of such polynucleotide. Also provided are blended pharmaceutical compositions that comprise one or more polynucleotides encoding mRNA and related methods of increasing the production of the functional polypeptide or protein encoded by such polynucleotide. As used herein, the terms "blend" and "blended" refer to pharmaceutical compositions that comprise two or more distinct, heterogeneous lipid nanoparticles. Typically, the two or more distinct, heterogeneous lipid nanoparticles are combined into a single pharmaceutical composition or formulation. For example, a blended pharmaceutical composition may comprise a first lipid nanoparticle that comprises the cationic lipid DOTAP and a second lipid nanoparticle that comprises the cationic lipid ICE. In some embodiments, a blended pharmaceutical composition may comprise a first lipid nanoparticle that comprises the cationic lipid C12-200 and a second lipid nanoparticle that comprises the cationic lipid DLinKC2DMA. An illustration of such a blended formulation is depicted in FIG. 1.

It should be noted that the terms "blend" and "blended" as used herein to describe the pharmaceutical compositions and formulations of the present invention are distinguishable from the terms "mix" or "mixture", which are used herein to describe a pharmaceutical formulation or composition that includes only a single lipid nanoparticle in the formulation. For example, the terms mix and mixture are used herein to refer to a pharmaceutical composition comprising only a single population of lipid nanoparticles, all of which generally have the same or substantially the same lipid composition. This is in contrast to a blended formulation which comprises two or more different lipid nanoparticles. In particular the terms "mix" and "mixture" are generally used to describe a pharmaceutical composition or formulation which includes a single, homogeneous population of lipid nanoparticles all of which are synthesized from an organic solution containing the same cationic lipids and, for example, any additional helper lipids or PEG-modified lipids.

The blended lipid nanoparticle compositions are characterized as being able to efficiently deliver the encapsulated polynucleotides to target cells, and are also characterized by their ability to improve the subsequent transfection of such encapsulated polynucleotides following contacting one or more target cells. The blended lipid nanoparticle compositions are also characterized by their ability to enhance (e.g., increase) the expression of polynucleotides encapsulated therein by target cells. The blended lipid nanoparticle compositions described herein are also characterized by their ability to enhance (e.g., increase) the production of one or more polypeptides or proteins (e.g., by target cells) encoded by one or more polynucleotides encapsulated in such nanoparticle compositions. Accordingly, such blended lipid nanoparticle pharmaceutical compositions are also useful for the treatment of diseases, and in particular the treatment of diseases which result from the aberrant expression of genes or gene products (e.g., diseases associated with the deficient production of a protein). For example, the diseases that the blended lipid nanoparticles and pharmaceutical compositions may be used to treat include those in which a genetic mutation of a particular gene causes the affected cells to not express, have reduced expression of, or to express a non-functional product of that gene. Contacting such target cells with the blended lipid nanoparticles and pharmaceutical compositions such that the target cells are transfected by the encapsulated polynucleotides increases the expression of such polynucleotides and increases the production of a functional protein or polypeptide product that may be useful in the treatment of disease (e.g., diseases resulting from a protein or enzyme deficiency).

In certain embodiments the blended lipid nanoparticles and pharmaceutical compositions described herein exhibit an increased ability to transfect one or more target cells. As used herein, the terms "transfect" or "transfection" refer to the intracellular introduction of a polynucleotide into a cell, or preferably into a target cell. The introduced polynucleotide may be stably or transiently maintained in the target cell. The term "transfection efficiency" refers to the relative amount of polynucleotide up-taken or introduced by the target cell which is subject to transfection. In practice, transfection efficiency is estimated by the amount of a reporter polynucleotide product expressed by the target cells following transfection. The blended lipid nanoparticles and pharmaceutical compositions described herein demonstrate high transfection efficiencies, and in particular such blends demonstrate high transfection efficiencies relative to the transfection efficiencies of the individual constituent lipid nanoparticles that comprise such blended compositions. The high transfection efficiencies observed by the blended lipid nanoparticle and pharmaceutical compositions can minimize adverse effects associated with both the lipids which comprise the nanoparticles as wells as the polynucleotides encapsulated by such lipids. Accordingly, the blended lipid nanoparticles of the present invention demonstrate high transfection efficacies thereby improving the likelihood that appropriate dosages of the polynucleotide will be delivered to the site of pathology, while at the same time minimizing potential systemic adverse effects.

As used herein, the terms "polynucleotide" and "nucleic acid" are used interchangeably to refer to genetic material (e.g., DNA or RNA), and when such terms are used with respect to the lipid nanoparticles generally refer to the genetic material encapsulated by such lipid nanoparticles. In some embodiments, the polynucleotide is RNA. Suitable RNA includes mRNA, siRNA, miRNA, snRNA and snoRNA. Contemplated polynucleotides also include large intergenic non-coding RNA (lincRNA), which generally do not encode proteins, but rather function, for example, in immune signaling, stem cell biology and the development of disease. (See, e.g., Guttman, et al., 458: 223-227 (2009); and Ng, et al., Nature Genetics 42: 10351036 (2010), the contents of which are incorporated herein by reference). In certain embodiments, the polynucleotides of the invention include RNA or stabilized RNA encoding a protein or enzyme (e.g., mRNA encoding human erythropoietin, as represented by SEQ ID NO: 3). The preset invention contemplates the use of such polynucleotides (and in particular RNA or stabilized RNA) as a therapeutic that is capable of being expressed by target cells to thereby facilitate the production (and in certain instances the excretion) of a functional enzyme or protein by such target cells, as disclosed for example, in International Application No. PCT/US2010/058457 and in U.S. Provisional Application No. PCT/US2012/041724 filed Jun. 8, 2012, the teachings of which are both incorporated herein by reference in their entirety. For example, in certain embodiments, upon the expression of one or more polynucleotides by target cells the production of a functional enzyme or protein in which a subject is deficient (e.g., a urea cycle enzyme or an enzyme associated with a lysosomal storage disorder) may be observed. The term "functional", as used herein to qualify a protein or enzyme, means that the protein or enzyme has biological activity, or alternatively is able to perform the same, or a similar function as the native or normally-functioning protein or enzyme.

Also provided herein are blended lipid nanoparticles, pharmaceutical compositions and related methods for modulating the expression of a polynucleotide and/or for modulating (e.g., increasing) the production of a functional polypeptide or protein (e.g., and enzyme) encoded by such polynucleotide in one or more target cells and tissues. In the context of the present invention the term "expression" is used in its broadest sense to refer to either the transcription of a specific gene or polynucleotide into at least one mRNA transcript, or the translation of at least one mRNA or polynucleotide into a polypeptide (e.g., a functional protein or enzyme). For example, in certain embodiments the blended lipid nanoparticles comprise at least a first and a second lipid nanoparticle, at least one of which comprise a polynucleotide (e.g., mRNA) which encodes a functional protein or enzyme. In the context of polynucleotides which comprise or encode mRNA, the term expression refers to the translation of such mRNA (e.g., by the target cells) to produce the polypeptide or protein encoded thereby. In the context of an antisense oligonucleotide encapsulated in one or more of the lipid nanoparticle compositions described herein, the term "expression" may be used with reference to one or more targeted genes or nucleic acids (e.g., mRNA). For example, where an encapsulated antisense oligonucleotide has been prepared to be complementary to a fragment of a target endogenous mRNA expressed by a cell, the term "expression" may be used with reference to such endogenous mRNA (e.g., the encapsulated antisense oligonucleotide may reduce the expression of such targeted mRNA).

Blended lipid nanoparticles and pharmaceutical compositions for modulating the expression of aberrantly expressed nucleic acids and polynucleotides in one or more target cells and tissues are also provided. In certain embodiments such blended lipid nanoparticles comprise at least a first lipid nanoparticle and a second lipid nanoparticle, one or both of which may encapsulate a polynucleotide. The blended lipid nanoparticles may comprise, for example, one or more polynucleotides encapsulated in a first lipid nanoparticle which is blended with one or more different lipid nanoparticles (i.e., a second or third lipid nanoparticle) that can optionally encapsulate one or more polynucleotides. Such blended lipid nanoparticle formulations demonstrate enhanced expression of the one or more polynucleotides encapsulated thereby relative to the expression of the same polynucleotides observed following the administration of a single lipid nanoparticle (e.g., the first lipid nanoparticle). Similarly, such blended lipid nanoparticle formulations may demonstrate enhanced production of one or more polypeptides (e.g., a functional enzyme) encoded by an encapsulated polynucleotides relative to the production of the same polypeptides observed following the administration of a single lipid nanoparticle (e.g., the first lipid nanoparticle). For example, in certain embodiments the blended lipid nanoparticles and pharmaceutical compositions are capable of increasing the expression of encapsulated polynucleotides, and/or the production of the polypeptides encoded by such encapsulated polynucleotides, in a target cell by at least about ten-fold, twenty-fold, thirty-fold, forty-fold, fifty-fold, sixty-fold, seventy-fold, one-hundred-fold, five-hundred-fold, one-thousand-fold, or more relative to the expression of polynucleotide or production of polypeptide observed when the target cell is contacted with such polynucleotides encapsulated in a single lipid nanoparticle.

Methods of enhancing (e.g., increasing) the expression of a polynucleotide and methods of increasing the production and secretion of a functional polypeptide product in target cells and tissues (e.g., hepatocytes) are also provided. In some embodiments, the targeted cells or tissues aberrantly express the polynucleotide encapsulated by one or more of the lipid nanoparticles that comprise the blended pharmaceutical composition. Also provided herein are methods of increasing the expression of one or more polynucleotides (e.g., mRNA) and methods of increasing the production and/or secretion of one or more polypeptides (e.g., a functional enzyme) in one or more target cells, tissues and organs. Generally, such methods comprise contacting the target cells with a pharmaceutical composition that comprises a blend of at least two lipid-based nanoparticles (e.g., a first and a second lipid nanoparticle), wherein at least one of such lipid-based nanoparticles comprises or otherwise encapsulates the one or more polynucleotides.

Also provided herein are methods and compositions for enhancing (e.g., increasing) or otherwise modulating the expression of one or more polynucleotides (e.g., mRNA) and/or enhancing (e.g., increasing) or otherwise modulating the production and secretion of the polypeptides or proteins encoded thereby in the targeted cells of a subject. Such methods generally comprise the step of administering (e.g., intravenously administering) a blended pharmaceutical composition to a subject wherein such pharmaceutical composition comprise at least two blended lipid nanoparticles (e.g., a first and a second lipid nanoparticle), at least one of which encapsulates or otherwise comprises one or more polynucleotides. In certain embodiments, the step of administering the blended pharmaceutical composition to a subject facilitates the contacting of the blended lipid nanoparticles with the targeted cells and tissues, the result of which is an enhanced (e.g., increased) expression of the encapsulated polynucleotides and enhanced (e.g., increased) product of the polypeptide encoded by such encapsulated polynucleotides by the contacted target cells and tissues. As the term "enhanced" is used herein to describe the activity of blended lipid nanoparticles, it should be noted that such enhancement is generally determined relative to the sum of the effect observed or produced by the constituent members that comprise the blended lipid nanoparticle formulation. For example, the enhanced expression of a polynucleotide and/or the enhanced production or secretion of a polypeptide which is observed following the administration of a blended lipid nanoparticle formulation comprising two different lipid nanoparticles designated "A" and "B", wherein only lipid nanoparticle "A" encapsulates the polynucleotide, is enhanced relative to the sum of the expression of polynucleotide and/or production or secretion of polypeptide observed by bot "A" and "B" when administered independently of one another.

The present inventors have discovered that in certain embodiments the expression of the polynucleotides (and the corresponding production and/or secretion of a polypeptide encoded by polynucleotides comprising mRNA) observed when such polynucleotides are administered in a blended lipid-based nanoparticle composition is enhanced and in many instances exceeds (e.g., by about two-, three-, four-, five-, ten-, twenty-, twenty-five-, thirty-, forty-, fifty-, sixty-, seventy-, eighty, ninety, one-hundred, two-hundred-fold or more) the expression (and the corresponding production and/or secretion of a polypeptide where such polynucleotides comprise mRNA) observed when such polynucleotides are administered using each of the two or more independent constituent lipid nanoparticles which comprise the blended lipid nanoparticle pharmaceutical compositions. Accordingly, the blended pharmaceutical compositions (e.g., a single pharmaceutical composition comprising two separate, non-identical lipid nanoparticles) demonstrate a synergistic (i.e., non-additive) increase in the expression of the polynucleotides encapsulated in the two or more lipid nanoparticles which comprise the pharmaceutical composition and a synergistic (i.e., non-additive) increase in the production and/or secretion of the polypeptides encoded by such encapsulated polynucleotides where such polynucleotides comprise mRNA. The synergistic increase is evident relative to the additive total expression of such polynucleotides (or the additive total production of polypeptides encoded by polynucleotides comprising mRNA), that is observed when each of the constituent lipid nanoparticles which comprise the blended pharmaceutical composition are administered individually. The observed synergistic increases in the expression of encapsulated polynucleotides (and/or production of polypeptide encoded by polynucleotides comprising mRNA) is evident across a variety of lipid nanoparticles and at various ratios of such blended lipid nanoparticles. Furthermore, the observed enhanced expression of polynucleotides encapsulated in at least one of the lipid nanoparticles which comprise the blended pharmaceutical compositions (and the corresponding production of the polypeptides encoded by encapsulated polynucleotides comprising mRNA) may range from about 1.5- to 25-fold increases, or more as compared to the sum of the expression (or where applicable the production and/or secretion) observed in the constituent lipid nanoparticles which comprise such blended pharmaceutical compositions, thereby demonstrating that blending of two or more separate lipid nanoparticles (at least one of which encapsulates a polynucleotide) mechanistically allows the greater expression of such polynucleotides, which in turn corresponds to a greater production of the product encoded thereby, as compared to the separate lipid nanoparticles comprising such blended pharmaceutical composition.

The mechanism of this synergistic augmentation in protein production has not yet been elucidated. Without wishing to be bound by any one particular theory, possible explanations include, for example, non-competing pathways or mechanisms of cellular entry by each of the lipid nanoparticle formulations that comprise the blended pharmaceutical composition, the combination of different intracellular trafficking mechanisms (e.g., proton-sponge vs. fusogenicity), the combination of drug release properties with endosomal release properties and/or the modulation of active inhibitory pathways allowing greater uptake of nanoparticles.

The blended pharmaceutical compositions, and in particular the constituent lipid nanoparticles which comprise such blended compositions, are capable of delivering polynucleotides of varying sizes to their target cells or tissues. In certain embodiments, the lipid nanoparticles of the present invention are capable of delivering large polynucleotide sequences (e.g., polynucleotides of at least 1 kb, 1.5 kb, 2 kb, 2.5 kb, 3 kb, 3.5 kb, 4 kb, 4.5 kb, 5 kb, 6 kb, 7 kb, 8 kb, 9 kb, 10 kb, 12 kb, 15 kb, 20 kb, 25 kb, 30 kb, or more).

In certain embodiments, the blended pharmaceutical compositions and the encapsulated polynucleotides comprised therein may be formulated with one or more acceptable excipients or reagents to facilitate the delivery of such polynucleotides to the intended or targeted cells, tissues and organs. Appropriate reagents and excipients may be generally selected with regards to a number of factors, which include, among other things, the biological or chemical properties of the polynucleotides (e.g., the charge), the intended route of administration, the anticipated biological environment to which such polynucleotides will be exposed and the specific properties of the intended target cells and tissues. In some embodiments, one or more of the lipid nanoparticles which comprise the blended pharmaceutical composition demonstrate a preferential and/or substantial binding to a target cell relative to non-target cells. In some embodiments, the lipid nanoparticles which comprise the blended pharmaceutical formulation, and in particular the lipid nanoparticles which encapsulate one or more polynucleotides, deliver their contents to the target cell such that the polynucleotides are delivered to the appropriate subcellular compartment, such as the cytoplasm, and may be expressed accordingly, such that, in certain embodiments one or more functional polypeptides (e.g., a functional protein) is produced and/or excreted by the target cell.

In certain embodiments, the blended pharmaceutical compositions comprise two or more separate lipid nanoparticles (e.g., a first lipid nanoparticle comprising HGT4003, DOPE, cholesterol and DMG-PEG2K blended with a second lipid nanoparticle comprising ICE, DOPE and DMG-PEG2K). The first lipid nanoparticle and the second lipid nanoparticle which comprise the blended pharmaceutical composition may each encapsulate the same one or more polynucleotides. A synergistic increase in the expression of the one or more polynucleotides by the target cells following the administration of the blended pharmaceutical compositions to a subject exceeds the relative sum of the expression of the one or more polynucleotides achieved by the first lipid nanoparticle and the expression of the one or more polynucleotides achieved by the second lipid nanoparticle when the first lipid nanoparticle and the second lipid nanoparticle are administered to the subject independently. Similarly, in certain embodiments a synergistic increase in the production one or more functional polypeptides encoded by one or more encapsulated polynucleotides by the target cells following administration of the blended pharmaceutical composition to a subject exceeds the relative sum of the production of the one or more functional polypeptides achieved by the first lipid nanoparticle and the production of the one or more polypeptides achieved by the second lipid nanoparticle when the first lipid nanoparticle and the second lipid nanoparticle are administered to the subject independently. Alternatively, in certain embodiments only one of the lipid nanoparticles (e.g., the first lipid nanoparticles) which comprise the blended pharmaceutical composition encapsulates one or more polynucleotides.

In some embodiments, the blended lipid nanoparticles and blended pharmaceutical compositions are capable of enhancing the expression of one or more polynucleotides irrespective whether some or all of the lipid nanoparticles which comprise the blended pharmaceutical composition encapsulate one or more polynucleotide. In particular, the blended lipid nanoparticles which comprise a first lipid nanoparticle encapsulating a polynucleotide and a second empty lipid nanoparticle (i.e., not encapsulating a polynucleotide) are capable of synergistically enhancing the expression of such polynucleotides (e.g., increasing expression about two-, four-, five-, ten-, twenty-, twenty-five-, thirty-, forty-, one-hundred-, two-hundred-, five-hundred-, one thousand-fold or more). Accordingly, in the context of the present invention, at least one of the liposomal lipid nanoparticle components of the blended formulation serves to transport the polynucleotide to the target cell. In some embodiments two of the at least two lipid nanoparticle components of the blended formulation serve to transport one or more polynucleotides to the target cell. Upon contacting the targeted cells, such blended pharmaceutical compositions demonstrate an increase in the expression of the encapsulated polynucleotide (e.g., by at least about two-, five-, ten- or twenty-fold) and, in certain embodiments thereby increases the production of a functional polypeptide encoded by such encapsulated polynucleotide.

As used herein, the phrase "lipid nanoparticle" refers to a vesicle or carrier comprising one or more lipids (e.g., cationic and/or non-cationic lipids). Examples of suitable lipids include, for example, the cationic lipids such as C12-200, ICE, DLin-KC2-DMA, DOPE, DMG-PEG-2000, HGT4003, non-cationic lipids, cholesterol-based lipids, helper lipids, PEG-modified lipids, as well as the phosphatidyl compounds (e.g., phosphatidylglycerol, phosphatidylcholine, phosphatidylserine, phosphatidylethanolamine, sphingolipids, cerebrosides, and gangliosides) and combinations or mixtures of the forgoing. The blended pharmaceutical compositions or mixtures of the forgoing. The blended pharmaceutical compositions described herein comprise at least two or more of the lipid nanoparticles each of which have a different lipid composition. Such two or more lipid nanoparticles which comprise the blended compositions are referred to herein as a "first lipid nanoparticle", "second lipid nanoparticle", "third lipid nanoparticle" and so forth. The designations of, for example first and second lipid nanoparticles are made for the purpose of distinguishing the different lipid nanoparticles that comprise the blended pharmaceutical compositions and are not intended to limit the number of different lipid nanoparticles that comprise such blended pharmaceutical compositions.

The present inventions also contemplate the use blended pharmaceutical compositions comprising one or more lipid nanoparticles that comprise one or more cationic lipids. As used herein, the phrase "cationic lipid" refers to any of a number of lipid species that carry a net positive charge at a selected pH, such as physiological pH. The contemplated lipid nanoparticles may be prepared by including multi-component lipid mixtures of varying ratios employing one or more cationic lipids, non-cationic lipids and PEG-modified lipids. In certain embodiments, each of the first and second lipid nanoparticles that comprise the blended pharmaceutical formulations comprise one or more cationic lipids. Similarly, also contemplated are blended pharmaceutical compositions that comprise two or more separate lipid nanoparticles, wherein such lipid nanoparticles comprise cationic lipids each having different lipid compositions. For example, in certain embodiments, the first and second lipid nanoparticles each comprise a different cationic lipid (e.g., the first lipid nanoparticle comprises ICE and the second lipid nanoparticle comprises DLin-KC2-DMA).

Several cationic lipids have been described in the literature, many of which are commercially available. Cationic lipids may include, but are not limited to ALNY-100 ((3aR,5s,6aS)-N,N-dimethyl-2,2-di((9Z,12Z)-octadeca-9,12-dienyl)tetrahydro-3aH-cyclopenta[d][1,3]dioxol-5-amine)), DODAP (1,2-dioleyl-3-dimethylammonium propane), HGT4003 (WO 2012/170889, the teachings of which are incorporated herein by reference in their entirety), HGT 5000 (U.S. Provisional Patent Application No. 61/617,468, the teachings of which are incorporated herein by reference in their entirety) or HGT5001 (cis or trans) (Provisional Patent Application No. 61/617,468), aminoalcohol lipidoids such as those disclosed in WO2010/053572, DOTAP (1,2-dioleyl-3-trimethylammonium propane), DOTMA (1,2-di-O-octadecenyl-3-trimethylammonium propane), DLinDMA (1,2-dilinoleyloxy-N,N-dimethyl-3-aminopropane) (Heyes, et al., J. Contr. Rel. 107:276-287 (2005)), DLin-KC2-DMA (Semple, et al., Nature Biotech. 28:172-176 (2010)), C12-200 (Love, et al., Proc. Nat'l. Acad. Sci. 107:1864-1869 (2010)), N-[1-(2,3-dioleyloxy)propyl]-N,N,N-trimethylammonium chloride. (Felgner et al. (Proc. Nat'l Acad. Sci. 84, 7413 (1987); U.S. Pat. No. 4,897,355). DOTMA can be formulated alone or can be combined with dioleoylphosphatidylethanolamine or "DOPE" or other cationic or non-cationic lipids into a lipid nanoparticle. Other suitable cationic lipids include, for example, 5-carboxyspermlglycinediocatadecylamide or "DOGS," 2,3-dioleyloxy-N-[2(spermine-carboxamido)ethyl]-N,N-dimethyl-1-propanaminium or "DOSPA" (Behr et al. Proc Nat.'l Acad. Sci. 86, 6982 (1989); U.S. Pat. Nos. 5,171,678; 5,334,761), 1,2-Dioleoyl-3-Dimethylammonium-Propane or "DODAP", 1,2-Dioleoyl-3-Trimethylammonium-Propane or "DOTAP". Contemplated cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-disteary-N,N-dimethylammonium bromide or "DDAB", N-(1,2-dimyristyloxyprop-3-yl)-N,N-mimethyl-N-hydroxyethyl ammonium bromide or "DMRIE", 3-dimethylamino-2-(cholest-5-en-3-beta-oxybutan-4-oxy)-1-(cis,cis-9,12-octadecadienoxy)propane or "CLinDMA", 2-[5'-(cholest-5-en-3-beta-oxy)-3'-oxapentoxy)-3-dimethyl-1-(cis,cis-9',1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin-K-DMA", 2,2-dilinoleyl-4-dimethylaminoethyl-[1,3]-dioxolane or "DLin-K-XTC2-DMA", or mixtures thereof. (Heyes, J., et al., J Controlled Release 107: 276-287 (2005); Morrissey, D V., et al., Nat. Biotechnol. 23(8): 1003-1007 (2005); PCT Publication WO2005/121348A1).

The use of cholesterol-based cationic lipids to formulate the blended lipid nanoparticles is also contemplated by the present invention. Such cholesterol-based cationic lipids can be used, either alone or in combination with other cationic or non-cationic lipids. Suitable cholesterol-based cationic lipids include, for example, DC-Chol (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335).

In addition, several reagents are commercially available to enhance transfection efficacy. Suitable examples include LIPOFECTIN (DOTMA:DOPE) (Invitrogen, Carlsbad, Calif.), LIPOFECTAMINE (DOSPA:DOPE) (Invitrogen), LIPOFECTAMINE2000, (Invitrogen), FUGENE, TRANSFECTAM (DOGS), and EFFECTENE.

Also contemplated are cationic lipids such as the dialkylamino-based, imidazole-based, and guanidinium-based lipids. For example, certain embodiments are directed to a composition comprising one or more imidazole-based cationic lipids, for example, the imidazole cholesterol ester or "ICE" lipid (3S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 3-(1H-imidazol-4-yl)propanoate, as represented by structure (I) below. In certain embodiments, a lipid nanoparticle for delivery of RNA (e.g., mRNA) encoding a functional protein may comprise one or more imidazole-based cationic lipids, for example, the imidazole cholesterol ester or "ICE" lipid (3S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 3-(1H-imidazol-4-yl)propanoate, as represented by structure (I).

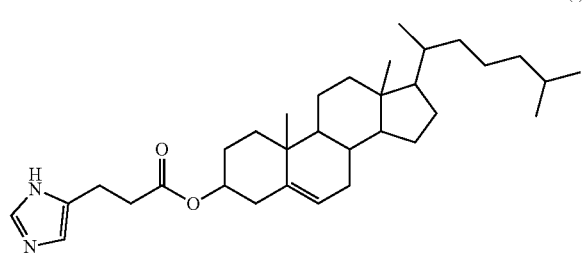

(I)

Without wishing to be bound by a particular theory, it is believed that the fusogenicity of the imidazole-based cationic lipid ICE is related to the endosomal disruption which is facilitated by the imidazole group, which has a lower pKa relative to traditional cationic lipids. The endosomal disruption in turn promotes osmotic swelling and the disruption of the liposomal membrane, followed by the transfection or intracellular release of the polynucleotide contents loaded or encapsulated therein into the target cell.

The imidazole-based cationic lipids are also characterized by their reduced toxicity relative to other cationic lipids. In some embodiments, one or more of the lipid nanoparticles which comprises the blended pharmaceutical composition comprise an imidazole-based cationic lipid such as ICE, to reduce the relative concentration of other more toxic cationic lipids in such blended pharmaceutical composition. The imidazole-based cationic lipids (e.g., ICE) may be used as the sole cationic lipid in one or more of the lipid nanoparticles that comprise the blended formulations, or alternatively may be combined with traditional cationic lipids (e.g., DOPE, DC-Chol), non-cationic lipids, PEG-modified lipids and/or helper lipids. The cationic lipid may comprise a molar ratio of about 1% to about 90%, about 2% to about 70%, about 5% to about 50%, about 10% to about 40% of the total lipid present in the lipid nanoparticle, or preferably about 20% to about 70% of the total lipid present in the lipid nanoparticle.

Similarly, certain embodiments are directed to lipid nanoparticles comprising the HGT4003 cationic lipid 2-((2,3-Bis((9Z,12Z)-octadeca-9,12-dien-1-yloxy)propyl)disulfanyl)-N,N-dimethylethanamine, as represented by structure (II) below, and as further described in U.S. Provisional Application No. PCT/US2012/041663, filed Jun. 8, 2012, the entire teachings of which are incorporated herein by reference in their entirety:

The use and inclusion of polyethylene glycol (PEG)-modified phospholipids and derivatized lipids such as derivatized cerarmides (PEG-CER), including N-Octanoyl-Sphingosine-1-[Succinyl(Methoxy Polyethylene Glycol)-2000] (C8 PEG-2000 ceramide) is also contemplated by the blended lipid nanoparticle formulations of the present invention, either alone or preferably in combination with other lipid formulations which comprise one or more of the lipid nanoparticles which comprise a blended pharmaceutical composition. Contemplated PEG-modified lipids include, but are not limited to, a polyethylene glycol chain of up to 5 kDa in length covalently attached to a lipid with alkyl chain(s) of $C_6$-$C_{20}$ length. The addition of such components may prevent complex aggregation and may also provide a means for increasing circulation lifetime and increasing the delivery of the lipid-polynucleotide composition to the target tissues, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., C14 or C18). The PEG-modified phospholipid and derivitized lipids of the present invention may comprise a molar ratio from about 0% to about 20%, about 0.5% to about 20%, about 1% to about 15%, about 4% to about 10%, or about 2% of the total lipid present in a liposomal lipid nanoparticle.

While lipid-based vehicles and their component lipids present promising means of delivering their polynucleotide contents intracellularly, the utility of many lipids (and in particular cationic lipids) may be limited by their associated cytotoxicity. This is particularly true of LIPOFECTIN, the DOTMA component of which is not-readily degraded in vivo and is toxic to cells and tissues. The blended lipid nanoparticle compositions of the present invention provide means of reducing the toxicities associated with lipids, and in particular the toxicity associated with cationic lipids. In certain embodiments, the synergistic enhancement in expression of encapsulated polynucleotides observed with the use of the blended lipid nanoparticle compositions of the present invention may correspond to reduced amounts of lipids (and in particular toxic lipids) necessary to effectuate the transfection of an effective amount of such polynucleotides to one or more target cells. Accordingly, also contemplated herein are methods for mediating, reducing or eliminating the toxicity associated with one or more lipids, and in particular one or more cationic lipids. For example, the amount of cationic lipid required to effectuate the transfection of an effective amount of one or more poly-

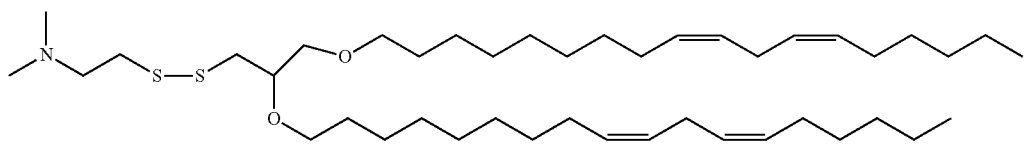

(II)

In other embodiments the compositions and methods described herein are directed to lipid nanoparticles comprising one or more cleavable lipids, such as, for example, one or more cationic lipids or compounds that comprise a cleavable disulfide (S—S) functional group (e.g., HGT4001, HGT4002, HGT4003, HGT4004 and HGT4005), as further described in U.S. Provisional Application No. PCT/US2012/041663.

nucleotides into one or more target cells may be reduce by incorporating such cationic lipid into a first lipid nanoparticle composition and blending such first lipid nanoparticle composition with a second lipid nanoparticle. The enhanced expression of the polynucleotide observed with the use of such blended lipid nanoparticle composition may permit a corresponding reduction in the amount of such lipid required to effectuate the transfection of an effective amount of such one or more polynucleotides into such one or more target cells. In certain amounts, the toxicity of the one or more lipids is reduced by at least about 10%, 15%, 20%, 25%, 30%, 40%, 50%, 60%, 75%, 80%, 90%, 95%, 99% or alternatively is eliminated.

The present invention also contemplates the use of non-cationic lipids in one or more of the lipid nanoparticles which comprise the blended formulations. As used herein, the phrase "non-cationic lipid" refers to any neutral, zwitterionic or anionic lipid. As used herein, the phrase "anionic lipid" refers to any of a number of lipid species that carry a net negative charge at a selected pH, such as physiological pH. Non-cationic lipids include, but are not limited to, distearoylphosphatidylcholine (DSPC), dioleoylphhosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidylethanolamine (SOPE), cholesterol, or a mixture thereof. Such non-cationic lipids may be used alone, but are preferably used in combination with other excipients, for example, cationic lipids. When used in combination with a cationic lipid, the non-cationic lipid may comprise a molar ratio of 5% to about 90%, or preferably about 10% to about 70% of the total lipid present in the lipid nanoparticle.

Also contemplated is inclusion of polymers in the lipid nanoparticles that comprise the blended pharmaceutical formulation. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins and polyethylenimine.

In certain embodiments, the lipid nanoparticles are formulated based in part upon their ability to facilitate the transfection of a polynucleotide to a target cell. In another embodiment, the lipid nanoparticles may be selected and/or prepared to optimize delivery of polynucleotides to a target cell, tissue or organ. For example, if the target cell is a hepatocyte the properties of the lipid nanoparticle (e.g., size, charge and/or pH) may be optimized to effectively deliver such lipid nanoparticle to the target cell or organ, reduce immune clearance and/or promote retention in that target organ. Alternatively, if the target tissue is the central nervous system the selection and preparation of the lipid nanoparticle must consider penetration of, and retention within the blood brain barrier and/or the use of alternate means of directly delivering such lipid nanoparticles to such target tissue (e.g., intracerebrovascular administration). In certain embodiments, the blended compositions or its constituent lipid nanoparticles may be combined with agents that facilitate the transfer of encapsulated polynucleotides (e.g., agents which disrupt or improve the permeability of the blood brain barrier and thereby enhance the transfer of such encapsulated polynucleotides to the target cells). While lipid nanoparticles can facilitate introduction of polynucleotides into target cells, the addition of polycations (e.g., poly L-lysine and protamine) to the lipid nanoparticles or the blended pharmaceutical compositions as a copolymer can also facilitate, and in some instances markedly enhance the transfection efficiency of several types of cationic liposomes by 2-28 fold in a number of cell lines both in vitro and in vivo. (See N. J. Caplen, et al., Gene Ther. 1995; 2: 603; S. Li, et al., Gene Ther. 1997; 4, 891.)

For the purposes of the present invention, at least one of the lipid nanoparticles (e.g., the first lipid nanoparticle) that comprise the blended pharmaceutical composition is prepared to encapsulate the desired one or more polynucleotide. In some embodiments all of the lipid nanoparticles that comprise a blended pharmaceutical composition are prepared to encapsulate one or more polynucleotides. For example, the blended first and second lipid nanoparticles that comprise the blended composition may each encapsulate the same polynucleotides (e.g., mRNA encoding a deficient enzyme), or alternatively may each encapsulate a different polynucleotide. The process of incorporating a desired polynucleotide (e.g., mRNA) into a liposome or a lipid nanoparticle is referred to herein as or "loading" or "encapsulating" (Lasic, et al., FEBS Lett., 312: 255-258, 1992). The lipid nanoparticle-loaded or -encapsulated polynucleotides may be completely or partially located in the interior space of the lipid nanoparticle, within the bilayer membrane of the lipid nanoparticle, or associated with the exterior surface of the lipid nanoparticle.

Loading or encapsulating a polynucleotide into a lipid nanoparticle may serve to protect the polynucleotide from an environment which may contain enzymes or chemicals (e.g., serum) that degrade polynucleotides and/or systems or receptors that cause the rapid excretion of the polynucleotides. Accordingly, in some embodiments, the selected lipid nanoparticles that comprise the blended pharmaceutical compositions are capable of enhancing the stability of the polynucleotide(s) encapsulated thereby, particularly with respect to the environments into which such polynucleotides will be exposed. Encapsulating the polynucleotides into one or more of the lipid nanoparticles which comprise the blended pharmaceutical compositions also facilitates the delivery of such polynucleotides into the target cells and tissues. For example, the lipid nanoparticles can allow the encapsulated polynucleotide to reach the target cell or may preferentially allow the encapsulated polynucleotide to reach the target cells or organs on a discriminatory basis (e.g., the lipid nanoparticles may concentrate in the liver or spleens of a subject to which the blended composition is administered). Alternatively, the lipid nanoparticles may limit the delivery of ecapsulated polynucleotides to other non-targeted cells or organs where the presence of the encapsulated polynucleotides may be undesirable or of limited utility.

Preferably, the lipid nanoparticles are prepared by combining multiple lipid and/or polymer components. For example, a lipid nanoparticle may be prepared using DSPC/CHOL/DODAP/C8-PEG-5000 ceramide in a molar ratio of about 1 to 50:5 to 65:5 to 90:1 to 25, respectively. A lipid nanoparticle may be comprised of additional lipid combinations in various ratios, including for example, DSPC/CHOL/DODAP/mPEG-5000 (e.g., combined at a molar ratio of about 33:40:25:2), DSPC/CHOL/DODAP/C8 PEG-2000-Cer (e.g., combined at a molar ratio of about 31:40:25:4), POPC/DODAP/C8-PEG-2000-Cer (e.g., combined at a molar ratio of about 75-87:3-14:10) or DSPC/CHOL/DOTAP/C8 PEG-2000-Cer (e.g., combined at a molar ratio of about 31:40:25:4). The selection of cationic lipids, non-cationic lipids and/or PEG-modified lipids which comprise the lipid nanoparticles, as well as the relative molar ratio of such lipids to each other, is based upon the characteristics of the selected lipid(s), the nature of the intended target cells or tissues and the characteristics of the polynucleotides to be delivered by the lipid nanoparticle. Additional considerations include, for example, the saturation of the alkyl chain, as well as the size, charge, pH, pKa, fusogenicity and toxicity of the selected lipid(s).

The lipid nanoparticles for use in the present invention can be prepared by various techniques which are presently known in the art. Multi-lamellar vesicles (MLV) may be prepared conventional techniques, for example, by deposition a selected lipid on the inside wall of a suitable container or vessel by dissolving the lipid in an appropriate solvent, and then evaporating the solvent to leave a thin film on the inside of the vessel or by spray drying. An aqueous phase may then added to the vessel with a vortexing motion which results in the formation of MLVs. Uni-lamellar vesicles (ULV) can then be formed by homogenization, sonication or extrusion of the multi-lamellar vesicles. In addition, unilamellar vesicles can be formed by detergent removal techniques.

In certain embodiments, the blended compositions of the present invention comprise a lipid nanoparticle wherein the polynucleotide (e.g., mRNA encoding OTC) is associated on both the surface of the lipid nanoparticle (e.g., a liposome) and encapsulated within the same lipid nanoparticle. For example, during preparation of the compositions of the present invention, cationic lipids which comprise the lipid nanoparticles may associate with the polynucleotides (e.g., mRNA) through electrostatic interactions with such therapeutic mRNA.

In certain embodiments, the blended compositions of the present invention may be loaded with diagnostic radionuclide, fluorescent materials or other materials that are detectable in both in vitro and in vivo applications. For example, suitable diagnostic materials for use in the present invention may include Rhodamine-dioleoylphosphatidylethanolamine (Rh-PE), Green Fluorescent Protein mRNA (GFP mRNA), *Renilla* Luciferase mRNA and Firefly Luciferase mRNA.

During the preparation of liposomal lipid nanoparticles, water soluble carrier agents may be also encapsulated in the aqueous interior by including them in the hydrating solution, and lipophilic molecules may be incorporated into the lipid bilayer by inclusion in the lipid formulation. In the case of certain molecules (e.g., cationic or anionic lipophilic polynucleotides), loading of the polynucleotide into preformed lipid nanoparticles or liposomes may be accomplished, for example, by the methods described in U.S. Pat. No. 4,946,683, the disclosure of which is incorporated herein by reference. Following encapsulation of the polynucleotide, the lipid nanoparticles may be processed to remove un-encapsulated mRNA through processes such as gel chromatography, diafiltration or ultrafiltration. For example, if it is desirous to remove externally bound polynucleotide from the surface of the lipid nanoparticles which comprise the blended pharmaceutical compositions, such lipid nanoparticles may be subject to a Diethylaminoethyl SEPHACEL column.

In addition to the encapsulated polynucleotide, one or more therapeutic or diagnostic agents may be included or encapsulated in the lipid nanoparticle. For example, such additional therapeutic agents may be associated with the surface of the lipid nanoparticle, can be incorporated into the lipid bilayer of the lipid nanoparticle by inclusion in the lipid formulation or loading into preformed lipid nanoparticles (see U.S. Pat. Nos. 5,194,654 and 5,223,263, which are incorporated by reference herein).

There are several methods for reducing the size, or "sizing", of lipid nanoparticles, and any of these methods may generally be employed when sizing is used as part of the invention. The extrusion method is a one method of liposome sizing. (Hope, M J et al. Reduction of Liposome Size and Preparation of Unilamellar Vesicles by Extrusion Techniques. In: *Liposome Technology* (G. Gregoriadis, Ed.) Vol. 1, p 123 (1993). The method consists of extruding liposomes through a small-pore polycarbonate membrane or an asymmetric ceramic membrane to reduce liposome sizes to a relatively well-defined size distribution. Typically, the suspension is cycled through the membrane one or more times until the desired liposome size distribution is achieved. The liposomes may be extruded through successively smaller pore membranes to achieve gradual reduction in liposome size.

A variety of alternative methods known in the art are available for sizing of a population of lipid nanoparticles. One such sizing method is described in U.S. Pat. No. 4,737,323, incorporated herein by reference. Sonicating a lipsome or lipid nanoparticle suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposomes sizes, typically between about 0.1 and 0.5 microns, are observed. The size of the lipid nanoparticles may be determined by quasi-electric light scattering (OELS) as described in Bloomfield, Ann. Rev. Biophys. Bioeg., 10:421-450 (1981), incorporated herein by reference. Average lipid nanoparticle diameter may be reduced by sonication of formed lipid nanoparticles. Intermittent sonication cycles may be alternated with QELS assessment to guide efficient liposome synthesis.

Selection of the appropriate size of a lipid nanoparticle must take into consideration the site of the target cell or tissue and to some extent the application for which the lipid nanoparticle is being made. As used herein, the phrase "target cell" refers to cells to which one or more of the lipid nanoparticles which comprise the blended composition are to be directed or targeted. In some embodiments, the target cells comprise a particular tissue or organ. In some embodiments, the target cells are deficient in a protein or enzyme of interest. For example, where it is desired to deliver a polynucleotide to a hepatocyte, the hepatocyte represents the target cell. In some embodiments, the polynucleotides and blended compositions of the present invention transfect the target cells on a discriminatory basis (i.e., do not transfect non-target cells). The compositions and methods of the present invention may be prepared to preferentially target a variety of target cells, which include, but are not limited to, hepatocytes, epithelial cells, hematopoietic cells, epithelial cells, endothelial cells, lung cells, bone cells, stem cells, mesenchymal cells, neural cells (e.g., meninges, astrocytes, motor neurons, cells of the dorsal root ganglia and anterior horn motor neurons), photoreceptor cells (e.g., rods and cones), retinal pigmented epithelial cells, secretory cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes and tumor cells.

Following transfection of one or more target cells by the polynucleotides encapsulated in the one or more lipid nanoparticles comprising the blended composition, the production of the product (e.g., a functional polypeptide or protein) encoded by such polynucleotide may be preferably stimulated and the capability of such target cells to express the polynucleotide and produce, for example, a polypeptide or protein of interest is enhanced. For example, transfection of a target cell by the blended compositions encapsulating OTC mRNA will enhance (i.e., increase) the expression of the OTC mRNA and produce a functional OTC enzyme.

In some embodiments, it may be desirable to limit transfection of the polynucleotides to certain cells or tissues. For example, the liver represents an important target organ for the compositions of the present invention in part due to its central role in metabolism and production of proteins and accordingly diseases which are caused by defects in liver-specific gene products (e.g., the urea cycle disorders) may benefit from specific targeting of cells (e.g., hepatocytes). Accordingly, in certain embodiments of the present invention, the structural characteristics of the target tissue may be exploited to direct the distribution of the lipid nanoparticles to such target tissues. For example, to target hepatocytes one or more of the lipid nanoparticles that comprise the blended pharmaceutical composition may be sized such that their dimensions are smaller than the fenestrations of the endothelial layer lining hepatic sinusoids in the liver; accordingly the one or more of such lipid nanoparticles can readily penetrate such endothelial fenestrations to reach the target hepatocytes. Alternatively, a lipid nanoparticle may be sized such that the dimensions of the liposome are of a sufficient diameter to limit or expressly avoid distribution into certain cells or tissues. For example, one or both of the first and a second lipid nanoparticle that comprise the blended pharmaceutical composition may be sized such that their dimensions are larger than the fenestrations of the endothelial layer lining hepatic sinusoids to thereby limit distribution of the liposomal lipid nanoparticle to hepatocytes. In such an embodiment, large liposomal lipid nanoparticles will not easily penetrate the endothelial fenestrations, and would instead be cleared by the macrophage Kupffer cells that line the liver sinusoids. Sizing of, for example, the first and second lipid nanoparticles comprising the blended composition may therefore provide an opportunity to further manipulate and precisely control the degree to which expression of the encapsulated polynucleotides may be enhanced in one or more target cells. Generally, the size of at least one of the lipid nanoparticles that comprise the blended pharmaceutical composition is within the range of about 25 to 250 nm, preferably less than about 250 nm, 175 nm, 150 nm, 125 nm, 100 nm, 75 nm, 50 nm, 25 nm or 10 nm.

Similarly, the compositions of the present invention may be prepared to preferentially distribute to other target tissues, cells or organs, such as the heart, lungs, kidneys, spleen. For example, the lipid nanoparticles of the present invention may be prepared to achieve enhanced delivery to the target cells and tissues. Accordingly, the compositions of the present invention may be enriched with additional cationic, non-cationic and PEG-modified lipids to further target tissues or cells.

In some embodiments, the lipid nanoparticles that comprise the blended compositions distribute to the cells and tissues of the liver to enhance the delivery, transfection and the subsequent expression of the polynucleotides (e.g., mRNA) encapsulated therein by the cells and tissues of the liver (e.g., hepatocytes) to, in certain embodiments, thereby enhance the production of a functional polypeptide encoded by such encapsulated polynucleotide. While such compositions may preferentially distribute into the cells and tissues of the liver, the therapeutic effects of the expressed polynucleotides and/or the polypeptides produced need not be limited to the target cells and tissues. For example, the targeted hepatocytes may function as a "reservoir" or "depot" capable of expressing and/or producing, and systemically or peripherally excreting a functional protein or enzyme. Accordingly, in certain embodiments of the present invention the one or more of the lipid nanoparticles that comprise the blended composition may target hepatocyes and/or preferentially distribute to the cells and tissues of the liver upon delivery. Following the transfection of the target hepatocytes by the polynucleotide encapsulated in one or more of the lipid nanoparticles that comprise the blended composition, such polynucleotides are expressed (e.g., translated) and a functional product (e.g., a polypeptide or protein) is excreted and systemically distributed, where such functional product may exert a desired therapeutic effect.

The polynucleotides encapsulated in one or more of the lipid nanoparticles that comprise the blended composition can be delivered to and/or transfect targeted cells or tissues. In some embodiments, the encapsulated polynucleotides are capable of being expressed and functional polypeptide products produced (and in some instances excreted) by the target cell, thereby conferring a beneficial property to, for example the target cells or tissues. Such encapsulated polynucleotides may encode, for example, a hormone, enzyme, receptor, polypeptide, peptide or other protein of interest. In certain embodiments, such encapsulated polynucleotides may also encode a small interfering RNA (siRNA) or antisense RNA for the purpose of decreasing or eliminating expression of an endogenous nucleic acid or gene. In certain embodiments such encapsulated polynucleotides may be natural or recombinant in nature and may exert their therapeutic activity using either sense or antisense mechanisms of action.

It should be understood that while certain embodiments described herein may cause an enhanced or modulated expression of one or more encapsulated polynucleotides by a target cell, the utility of the blended compositions described herein are not limited to increases in expression of encapsulated polynucleotides. Rather, in certain embodiments, the blended compositions described herein may modulate or otherwise cause a synergistic reduction in the expression of one or more genes or nucleic acids in a target cell. For example, in certain embodiments where one or more of the encapsulated polynucleotides comprising the blended formulations hereof are antisense oligonucleotides, such blended formulations may synergistically enhance (e.g., increase) the delivery of such encapsulated antisense oligonucleotides to one or more target cells, thereby modulating or enhancing the interference with or inhibition of the expression or production of a targeted gene or nucleic acid. Accordingly, where the encapsulated polynucleotides are, for example, antisense oligonucleotides or siRNA, the blended formulations comprising such polynucleotides may synergistically enhance the delivery of encapsulated polynucleotides to the target cells (e.g., enhanced by about one-, two-, three-, four-, five-, six-, eight-, ten-, twelve-, fifteen-, twenty-, twenty-five, fifty-, one-hundred, five-hundred, one thousand-fold, or more). Such enhanced delivery of, for example, the antisense or siRNA polynucleotides, using the blended formulations described herein would thereby synergistically reduce the expression of the targeted nucleic acids (e.g., such that the production of a nucleic acid or protein corresponding to such targeted nucleic acids is reduced or otherwise eliminated). In such an embodiment, the delivery of the encapsulated polynucleotides to the target cells may be synergistically enhanced (e.g., increased); and accordingly the function of the encapsulated polynucleotides also enhanced, thereby causing a corresponding reduction in the expression of the targeted genes or nucleic acids.

Similarly, in certain embodiments, the inventions described herein may cause a synergistically enhanced (e.g., increased) production of one or more polypeptides or proteins that are encoded by the encapsulate polynucleotides. In certain embodiments where such polypeptides or proteins are excreted into the peripheral circulation of a subject, such enhanced production of polypeptides or protein encoded by, for example, an encapsulate mRNA polynucleotide, using the blended formulations described herein would thereby be expected to cause a corresponding enhanced (e.g., increased) secretion of such polypeptides peripherally.

In some embodiments, the encapsulated polynucleotides (e.g., mRNA encoding a deficient protein) may optionally include chemical or biological modifications which, for example, improves the stability and/or half-life of such polynucleotide or which improves or otherwise facilitates translation of such polynucleotide.

Also contemplated by the present invention is the co-delivery of one or more unique polynucleotides to target cells by the lipid nanoparticles that comprises the blended compositions, for example, by combining two unique polynucleotides into a single lipid nanoparticle. In certain embodiments, a first polynucleotide, such as mRNA encoding galactose-1-phosphate uridyltransferase (GALT) as represented by SEQ ID NO:2, and a second polynucleotide, such as mRNA encoding galatokinase (GALK), may be encapsulated into a single liposomal-based lipid nanoparticle (e.g., a first lipid nanoparticle) and blended with a second lipid nanoparticle and administered to a subject in need thereof (e.g., for the treatment of galactosemia). Alternatively, in certain embodiments, a first polynucleotide, such as mRNA encoding galactose-1-phosphate uridyltransferase (GALT) as represented by SEQ ID NO: 2, and a second polynucleotide, such as mRNA encoding galatokinase (GALK), may be respectively encapsulated into a first and a second lipid nanoparticle, and such first and second lipid nanoparticles blended and administered to a subject in need thereof (e.g., for the treatment of galactosemia). Also contemplated are the co-delivery and/or co-administration of a first polynucleotide and a second polynucleotide in a blended pharmaceutical composition. For example, such first and second polynucleotides (e.g., exogenous or synthetic mRNA) may be respectively encapsulated in a first and second lipid nanoparticle and such first and second lipid nanoparticles blended into a single pharmaceutical composition. In certain embodiments, the second polynucleotide encapsulated by the second lipid nanoparticle enhances the delivery or enhances the expression of the first polynucleotide. Similarly, in certain embodiments, the first polynucleotide encapsulated by the first lipid nanoparticle facilitates the delivery or synergistically enhances the expression of the second polynucleotide. Alternatively, a polynucleotide may be encapsulated in a first lipid nanoparticle and subsequently blended with a second empty lipid nanoparticle (i.e., a lipid nanoparticle that does not encapsulate a polynucleotide). In such an embodiment, the expression of the polynucleotide may be enhanced (e.g., increased) relative to the expression of the polynucleotides observed when the first lipid nanoparticle is administered independently of the second lipid nanoparticle (e.g., expression of the polynucleotide may be synergistically increased by about two-, four-, five-, ten-, twelve, fifteen- or twenty-fold or more).

Also contemplated is the delivery of one or more encapsulated polynucleotides to one or more target cells to treat a single disorder or deficiency, wherein each such polynucleotide functions by a different mechanism of action. For example, the blended pharmaceutical compositions of the present invention may comprise a first polynucleotide which, for example, is encapsulated in a first lipid nanoparticle and intended to correct an endogenous protein or enzyme deficiency, and which is blended with a second polynucleotide encapsulated in a second lipid nanoparticle and intended to deactivate or "knock-down" a malfunctioning endogenous polynucleotide and its protein or enzyme product. Such encapsulated polynucleotides may encode, for example mRNA and siRNA. Alternatively, such polynucleotides may be encapsulated in the same lipid nanoparticle and blended with an empty lipid nanoparticle. In each such embodiments, the expression of the encapsulated polynucleotides may be synergistically enhanced (e.g., increased) relative to the expression of the polynucleotides observed when such first lipid nanoparticles are administered independently of the second lipid nanoparticles. For example, the expression of the encapsulated polynucleotide may be synergistically increased by at least about two-, four-, five-, ten-, twelve, fifteen- or twenty-fold or more, relative to the sum of the expression of the polynucleotides observed when such first lipid nanoparticles are administered independently of the second lipid nanoparticles.

While in vitro transcribed polynucleotides (e.g., mRNA) may be transfected into target cells, such polynucleotides may be readily and efficiently degraded by the cell in vivo, thus rendering such polynucleotides ineffective. Moreover, some polynucleotides are unstable in bodily fluids (particularly human serum) ad can be degraded or digested even before reaching a target cell. In addition, within a cell, a natural mRNA can decay with a half-life of between 30 minutes and several days. Accordingly, in certain embodiments, the lipid nanoparticle-encapsulated polynucleotides provided herein, and in particular the mRNA polynucleotides provided herein, preferably retain at least some ability to be expressed or translated, to thereby produce a functional protein or enzyme within one or more target cells.

In certain embodiments, the blended pharmaceutical compositions comprise one or more lipid nanoparticles that include or encapsulate one or more stabilized polynucleotides (e.g., mRNA which has been stabilized against in vivo nuclease digestion or degradation) that modulate the expression of a gene or that may be expressed or translated to produce a functional polypeptide or protein within one or more target cells. In certain embodiments, the activity of such encapsulated polynucleotides (e.g., mRNA encoding a functional protein or enzyme) is prolonged over an extended period of time. For example, the activity of the polynucleotides may be prolonged such that the blended pharmaceutical compositions may be administered to a subject on a semi-weekly or bi-weekly basis, or more preferably on a monthly, bi-monthly, quarterly or an annual basis. The extended or prolonged activity of the blended pharmaceutical compositions of the present invention, and in particular of the encapsulated mRNA, is directly related to the quantity of functional protein or enzyme translated from such mRNA. Similarly, the activity of the blended compositions of the present invention may be further extended or prolonged by chemical modifications made to further improve or enhance translation of the mRNA polynucleotides. For example, the Kozac consensus sequence plays a role in the initiation of protein translation, and the inclusion of such a Kozac consensus sequence in the encapsulated mRNA polynucleotides may further extend or prolong the activity of the mRNA polynucleotides. Furthermore, the quantity of functional protein or enzyme expressed and produced by the target cell is a function of the quantity of polynucleotide (e.g., mRNA) delivered to the target cells and the stability of such polynucleotide. To the extent that the stability of the polynucleotides of the present invention may be improved or enhanced, the half-life, the activity of the translated protein or enzyme and the dosing frequency of the composition may be further extended.

In some embodiments, the polynucleotides encapsulated in the pharmaceutical compositions comprise mRNA (e.g., SEQ ID NO:3 encoding human erythropoietin mRNA). In certain embodiments the polynucleotides can be chemically modified for example, to confer stability (e.g., stability relative to the wild-type or naturally-occurring version of the mRNA and/or the version of the mRNA naturally endogenous to target cells). Accordingly, in some embodiments, the encapsulated polynucleotides provided herein comprise at least one chemical modification which confers increased or enhanced stability to the polynucleotide, including, for example, improved resistance to nuclease digestion in vivo. As used herein, the phrases "chemical modifications" ad "chemically modified" as such terms relate to the polynucleotides provided herein, include at least one alteration which preferably enhances stability and renders the polynucleotide more stable (e.g., resistant to nuclease digestion) than the wild-type or naturally occurring version of that polynucleotide. The terms "stable" and "stability" as such terms relate to the polynucleotides of the present invention, and particularly with respect to the mRNA, refer to increased or enhanced resistance to degradation by, for example nucleases (i.e., endonucleases or exonucleases) which are normally capable of degrading such RNA. Increased stability can include, for example, less sensitivity to hydrolysis or other destruction by endogenous enzymes (e.g., endonucleases or exonucleases) or encapsulated mRNA, is directly related to the quantity of functional protein or enzyme translated from such mRNA. Similarly, the activity of the blended compositions of the present invention may be further extended or prolonged by chemical modifications made to further improve or enhance translation of the mRNA polynucleotides. For example, the Kozac consensus sequence plays a role in the initiation of protein translation, and the inclusion of such a Kozac consensus sequence in the encapsulated mRNA polynucleotides may further extend or prolong the activity of the mRNA polynucleotides. Furthermore, the quantity of functional protein or enzyme expressed and produced by the target cell is a function of the quantity of polynucleotide (e.g., mRNA) delivered to the target cells and the stability of such polynucleotide. To the extent that the stability of the polynucleotides of the present invention may be improved or enhanced, the half-life, the activity of the translated protein or enzyme and the dosing frequency of the composition may be further extended.

In some embodiments, the polynucleotides encapsulated in the pharmaceutical compositions comprise mRNA (e.g., SEQ ID NO: 3 encoding human erythropoietin mRNA). In certain embodiments the polynucleotides can be chemically modified for example, to confer stability (e.g., stability relative to the wild-type or naturally-occurring version of the mRNA and/or the version of the mRNA naturally endogenous to target cells). Accordingly in some embodiments, the encapsulated polynucleotides provided herein comprise at least one chemical modification which confers increased or enhanced stability to the polynucleotide, including, for example, improved resistance to nuclease digestion in vivo. As used herein, the phrases "chemical modifications" and "chemically modified" as such terms relate to the polynucleotides provided herein, include at least one alteration which preferably enhances stability and renders the polynucleotide more stable (e.g., resistant to nuclease digestion) than the wild-type or naturally occurring version of that polynucleotide. The terms "stable" and "stability" as such terms relate to the polynucleotides of the present invention, and particularly with respect to the mRNA, refer to increased or enhanced resistance to degradation by, for example nucleases (i.e., endonucleases or exonucleases) which are normally capable of degrading such RNA. Increased stability can include, for example, less sensitivity to hydrolysis or other destruction by endogenous enzymes (e.g., endonucleases or exonucleases) or conditions within the target cell or tissue, thereby increasing or enhancing the residence of such polynucleotides in the target cell, tissue, subject and/or cytoplasm. The stabilized polynucleotide molecules provided herein demonstrate longer half-lives relative to their naturally occurring, unmodified counterparts (e.g. the wild-type version of the polynucleotide).

Also contemplated by the phrases "chemical modification" and "chemically modified" as such terms related to the polynucleotides of the present invention are alterations which improve or enhance translation of mRNA polynucleotides, including for example, the inclusion of sequences which function in the initiation of protein translation (e.g., the Kozac consensus sequence). (Kozak, M., Nucleic Acids Res 15 (20: 8125-48 (1987)). The phrase "chemical modification" as used herein, also include modifications which introduce chemistries which differ from those seen in naturally occurring polynucleotides, for example, covalent modifications such as the introduction of modified nucleotides, (e.g., nucleotide analogs, or the inclusion of pendant groups which are not naturally found in such polynucleotide molecules). In some embodiments, the polynucleotides have undergone a chemical or biological modification to render them more stable prior to encapsulation in one or more lipid nanoparticles. Exemplary chemical modifications to a polynucleotide include the depletion of a base (e.g., by deletion or by the substitution of one nucleotide for another) or chemical modification of a base.

In addition, suitable modifications include alterations in one or more nucleotides of a codon such that the codon encodes the same amino acid but is more stable than the codon found in the wild-type version of the polynucleotide. For example, an inverse relationship between the stability of RNA and a higher number cytidines (C's) and/or uridines (U's) residues has been demonstrated, and RNA devoid of C and U residues have been found to be stable to most RNases (Heidenreich, et al. J Biol Chem 269, 2131-8 (1994)). In some embodiments, the number of C and/or U residues in an mRNA sequence is reduced. In a another embodiment, the number of C and/or U residues is reduced by substitution of one codon encoding a particular amino acid for another codon encoding the same or a related amino acid. Contemplated modifications to the mRNA polynucleotides of the present invention also include the incorporation of pseudouridines. The incorporation of pseudouridines into the mRNA polynucleotides of the present invention may enhance stability and translational capacity, as well as diminishing immunogenicity in vivo. (See, e.g., Karikó, K., et al., Molecular Therapy 16 (11): 1833-1840 (2008)). Substitutions and modifications to the polynucleotides of the present invention may be performed by methods readily known to one or ordinary skill in the art.

The constraints on reducing the number of C and U residues in a sequence will likely be greater within the coding region of an mRNA, compared to an untranslated region, (i.e., it will likely not be possible to eliminate all of the C and U residues present in the message while still retaining the ability of the message to encode the desired amino acid sequence). The degeneracy of the genetic code, however presents an opportunity to allow the number of C and/or U residues that are present in the sequence to be reduced, while maintaining the same coding capacity (i.e., depending on which amino acid is encoded by a codon, several different possibilities for modification of RNA sequences may be possible). For example, the codons for Gly can be altered to GGA or GGG instead of GGU or GGC.

The encapsulated polynucleotides may include both naturally occurring a well as non-naturally occurring variants, and accordingly such polynucleotides may comprise not only the known purine and pyrimidine heterocycles but also heterocyclic analogues and tautomeres thereof. Contemplated examples include, but are not limited to adenine, guanine, cytosine, thymidine, uracil, xanthine, hypoxanthine, pseudouridine, 5-methylcytosine, isocytosine, pseudoisocytosine, 5-bromouracil, 5-propynyluracil, 6-aminopurine, 2-aminopurine, inosine, diaminopurine, and 2-chloro-6-aminopurine. In some embodiments, at least one of the nucleotides present in the polynucleotide is a modified nucleobase selected from the group, consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

The term chemical modification also includes, for example, the incorporation of non-nucleotide linkages or modified nucleotides into the polynucleotide sequences of the present invention (e.g., end-blocking modifications to one or both the 3' and 5' ends of an mRNA molecule encoding a functional protein or enzyme). Such modifications may include the addition of bases to a polynucleotide sequence (e.g., the inclusion of a poly A tail or a longer poly A tail), the alteration of the 3' UTR or the 5' UTR, complexing the polynucleotide with an agent (e.g., a protein or a complementary polynucleotide molecule), and inclusion of elements which change the structure of a polynucleotide molecule (e.g., which form secondary structures).

The poly A tail is thought to stabilize natural messengers and synthetic sense RNA. Therefore, in certain embodiments a long poly A tail can be added to an mRNA molecule thus rendering the RNA more stable. Poly A tails can be added using a variety of art-recognized techniques. For example, long poly A tails can be added to synthetic or in vitro transcribed RNA using poly A polymerase (Yokoe, et al. Nature Biotechnology. 1996; 14: 1252-1256). A transcription vector can also encode long poly A tails. In addition, poly A tails can be added by transcription directly from PCR products. Poly A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)). In certain embodiments, the length of the poly A tail is at least about 90, 200, 300, 400 at least 500 nucleotides. In certain embodiments, the length of the poly A tail is adjusted to control the stability of a modified sense mRNA molecule of the invention and, thus, the transcription of protein. For example, since the length of the poly A tail can influence the half-life of a sense mRNA molecule, the length of the poly A tail can be adjusted to modify the level of resistance of the mRNA to nucleases and thereby control the time course of polynucleotide expression an/or polypeptide production in a target cell. In certain embodiments, the stabilized polynucleotide molecules are sufficiently resistant to in vivo degradation (e.g., by nucleases), such that they may be delivered to the target cell without a lipid nanoparticle.

In certain embodiments, the chemical modifications are end-blocking modification of the one or more polynucleotides which comprise the blended pharmaceutical compositions of the invention. For example, such polynucleotides can be modified by the incorporation 3' and/or 5' untranslated (UTR) sequences which are not naturally found in the wild-type polynucleotide. In certain embodiments, 3' and/or 5' flanking sequence which naturally flanks an MRNA and encodes a second, unrelated protein can be incorporated into the nucleotide sequence of an mRNA molecule encoding a or functional protein in order to modify it. For example, 3' or 5' sequences from mRNA molecules which are stable (e.g., globin, actin, GAPDH, tubulin, histone, or citric acid cycle enzymes) can be incorporated into the 3' and/or 5' region of a sense mRNA polynucleotide molecule to increase the stability of the sense mRNA molecule.

Also contemplated by the present invention are modifications to the polynucleotide sequences made to one or both of the 3' and 5' ends of the polynucleotide. For example, the present invention contemplates modifications to the 5' end of the polynucleotides (e.g., mRNA) to include a partial sequence of a CMV immediate-early 1 (IE1) gene, or a fragment thereof to improve the nuclease resistance and/or improve the half-life of the polynucleotide. In addition to increasing the stability of the mRNA polynucleotide sequence, it has been surprisingly discovered the inclusion of a partial sequence of a CMV immediate-early 1 (IE1) gene (e.g., to the 5' untranslated region of the mRNA) further enhances the translation of the mRNA. Also contemplated is the inclusion of a sequence encoding human growth hormone (hGH), or a fragment thereof to the 3' end or untranslated region of the polynucleotide (e.g., mRNA) to further stabilize the polynucleotide. Generally, the contemplated chemical modifications improve the stability and/or pharmacokinetic properties (e.g., half-life) of the polynucleotide relative to their unmodified counterparts, and include, for example modifications made to improve such polynucleotides' resistance to in vivo nuclease digestion.

Contemplated chemical modification also include, for example, modifying encapsulated polynucleotides to include non-naturally occurring nucleotides comprising, for example modified sugar and/or base moieties, which are also referred to herein as "nucleotide analogues". Non-naturally occurring nucleotides include nucleotides which have modified sugar moieties, such as bicyclic nucleotides or 2' modified nucleotides, such as 2' substituted nucleotides. In some embodiments, the nucleotide analogues are variants of natural nucleotides, such as DNA or RNA nucleotides, by virtue of, for example, modifications in the sugar and/or base moieties.

In certain embodiments, the contemplated nucleotide analogues may be functionally equivalent to the naturally occurring nucleotides in the context of the polynucleotide. For example, the nucleotide analogues may have no functional effect on the way the polynucleotide functions. Such functionally equivalent nucleotide analogues may nevertheless be useful if, for example, they are easier or cheaper to manufacture, or are more stable to storage or manufacturing conditions, or represent a tag or label.

In other embodiments, the nucleotide analogues may have a functional effect on the way in which the polynucleotide functions (e.g., by increasing resistance to intracellular nucleases and/or increased ease of transport into the target cell). Specific examples of contemplated nucleotide analogues are described by, for example, in Freir, et al., Nucl. Acid Res. (1997) 25: 4429-4443 and Uhlmann, et al., Curr. Opinion in Drug Development (2000) 3(2): 293-213.

The polynucleotides disclosed herein may thus comprise or consist of a sequence of naturally-occurring nucleotides, (e.g., DNA or mRNA), or alternatively may comprise or consist of a combination of such naturally occurring nucleotides and one or more non-naturally occurring nucleotides, (e.g., nucleotide analogues). In certain embodiments, for example, where the encapsulated polynucleotides comprises or consists of antisense oligonucleotides, the inclusion of nucleotide analogues in such polynucleotides may suitably enhance the affinity of the polynucleotide for one or more target sequences. Additional examples of suitable and preferred nucleotide analogues are provided in International Patent Application WO 2007/031091, the contents of which are incorporated by reference herein.

In some embodiments the nucleotide analogues are independently selected from, for example: 2'-O-alkyl-RNA units, 2'-amino-DNA units, 2'-fluoro-DNA units, locked nucleic acid units, arabino nucleic acid (ANA) units, 2'-fluoro-ANA units, HNA units, INA (intercalating nucleic acid units as discussed by Christensen, et al., Nucl. Acids. Res. (2002) 30: 4918-4925) and 2'MOE units. In certain embodiments there is only one of the above types of nucleotide analogues present in the polynucleotides of the invention.

In some embodiments the nucleotide analogues comprise 2'-O-methoxyethyl-RNA (2'MOE), 2'-fluoro-DNA monomers or LNA nucleotide analogues, and as such the polynucleotides of the invention may comprise nucleotide analogues which are independently selected from these three types of analogues, or alternatively may comprise only one type of analogue selected from the three types. In some embodiments at least one of the nucleotides of an encapsulated polynucleotide is 2'-MOE-RNA, such as 2, 3, 4, 5, 6, 7, 8, 9 or 10 2'-MOE-RNA nucleotide units. In some embodiments at least one of the nucleotides of an encapsulated polynucleotide is 2'-fluoro DNA, such as 2, 3, 4, 5, 6, 7, 8, 9 or 10 2'-fluoro-DNA nucleotide units.

In some embodiments, the encapsulated polynucleotides comprise at least one locked nucleic acid (LNA) unit, such as 1, 2, 3, 4, 5, 6, 7, or 8 LNA units, such as from about 3-7 or 4-8 LNA units, or 3, 4, 5, 6 or 7 LNA units. In some embodiments, all the nucleotides of the polynucleotide are LNA. In some embodiments, the polynucleotide may comprise both beta-D-oxy-LNA, and one or more of the following LNA units: thio-LNA, amino-LNA, oxy-LNA, and/or ENA in either the beta-D or alpha-L configurations or combinations thereof. In some embodiments all LNA cytosine units are 5' methyl-cytosine.

In some embodiments, the blended pharmaceutical composition, the two or more lipid nanoparticles comprised therein or the polynucleotides encapsulate by such lipid nanoparticles can comprise a stabilizing reagent. The compositions can include one or more formulation reagents that bind directly or indirectly to, and stabilize the polynucleotide, thereby enhancing residence time in the cytoplasm of a target cell. Such reagents preferably lead to an improved half-life of a polynucleotide in the target cells. For example, the stability of an mRNA and efficiency of translation may be increased by the incorporation of "stabilizing reagents" that form complexes with the polynucleotides (e.g., mRNA) that naturally occur within a cell (see e.g., U.S. Pat. No. 5,677,124). Incorporation of a stabilizing reagent can be accomplished for example, by combining the poly A and a protein with the mRNA to be stabilized in vitro before loading or encapsulating the mRNA within the one or more lipid nanoparticles that comprise the blended pharmaceutical composition. Exemplary stabilizing reagents include one or more proteins, peptides, aptamers, translational accessory protein, mRNA binding proteins, and/or translation initiation factors.

Stabilization of the blended pharmaceutical compositions described herein, and of the constituent lipid nanoparticles, may also be improved by the use of opsonization-inhibiting moieties, which are typically large hydrophilic polymers that are chemically or physically bound or otherwise incorporated into the lipid nanoparticle (e.g., by the intercalation of a lipid-soluble anchor into the membrane itself, or by binding directly to active groups of membrane lipids). These opsonization-inhibiting hydrophilic polymers form a protective surface layer which significantly decreases the uptake of the liposomes by the macrophage-monocyte system and reticulo-endothelial system (e.g., as described in U.S. Pat. No. 4,920,016, the entire disclosure of which is herein incorporated by reference). For example, delays in the uptake of lipid nanoparticles by the reticuloendothelial system may be facilitated by the addition of a hydrophilic polymer surface coating onto or into lipid nanoparticles to mask the recognition and uptake of the liposomal-based lipid nanoparticle by the reticuloedothelial system. For example, in certain embodiments, one or more of the lipid nanoparticles that comprise the blended formulations comprise a polyethyleneglycol (PEG) polymer or a PEG-modified lipid to further enhance delivery of such lipid nanoparticles to the target cell and tissues.

When RNA is hybridized to a complementary polynucleotide molecule (e.g., DNA or RNA) it may be protected from nucleases. (Krieg, et al. Melton. Methods in Enzymology, 1987; 155, 397-415). The stability of hybridized mRNA is likely due to the inherent single strand specificity of most RNases. In some embodiments, the stabilizing reagent selected to complex a polynucleotide is a eukaryotic protein, (e.g., a mammalian protein). In yet another embodiment, the polynucleotide (e.g., mRNA) for use in sense therapy can be modified by hybridization to a second polynucleotide molecule. If an entire mRNA molecule were hybridized to a complementary polynucleotide molecule translation initiation may be reduced. In some embodiments the 5' untranslated region and the AUG start region of the mRNA molecular may optionally be left unhybridized. Following translation initiation, the unwinding activity of the ribosome complex can function even on high affinity duplexes so that translation can proceed. (Liebhaber. J. Mol. Biol. 1992; 226: 2-13; Monia, et al. J Biol Chem, 1993; 268: 14514-22.) It will be understood that any of the above described methods for enhancing the stability of polynucleotides may be used either alone or in combination with one or more of any of the other above-described methods and/or compositions.

In certain embodiments, the blended pharmaceutical compositions of the present invention enhance the delivery of lipid nanoparticle-encapsulated polynucleotides to one or more target cells, tissues or organs. In some embodiments, enhanced delivery to one or more target cells comprises increasing the amount of polynucleotide that comes in contact or is otherwise delivered to the target cells. In some embodiments, enhancing delivery to target cells comprises reducing the amount of polynucleotide that comes into contact with non-target cells. In some embodiments, enhancing delivery to target cells comprises allowing the transfection of at least some target cells with the encapsulated polynucleotide. In some embodiments, the level of expression of the polynucleotide encapsulated by the lipid nanoparticles which comprise the subject blended pharmaceutical compositions is increased in target cells.

The polynucleotides of the present invention may be optionally combined with a reporter gene (e.g., upstream or downstream of the coding region of the polynucleotide) which, for example, facilitates the determination of polynucleotide delivery to the target cells or tissues. Suitable reporter genes may include, for example, Green Fluorescent Protein mRNA (GFP mRNA), *Renilla* Luciferase mRNA (Luciferase mRNA), Firefly Luciferase mRNA (SEQ ID NO: 1), or any combinations thereof. For example, GFP mRNA may be fused with a polynucleotide encoding OTC mRNA to facilitate confirmation of mRNA localization in the target cells, tissues or organs.

In some embodiments, the blended compositions of the present invention comprise one or more additional molecules (e.g., proteins, peptides, aptamers or oliogonucleotides) which facilitate the transfer of the polynucleotides (e.g., mRNA, miRNA, snRNA and snoRNA) from the lipid nanoparticle into an intracellular compartment of the target cell. In some embodiments, the additional molecule facilitates the delivery of the polynucleotides into, for example, the cytosol, the lysosome, the mitochondrion, the nucleus, the nucleolae or the proteasome of a target cell. Also included are agents that facilitate the transport of the translated protein of interest from the cytoplasm to its normal intercellular location (e.g., in the mitochondrion) to treat deficiencies in that organelle. In some embodiments, the agent is selected from the group consisting of a protein, a peptide, an aptamer, and an oligonucleotide.

In some embodiments, the compositions of the present invention facilitate a subject's endogenous production of one or more functional proteins and/or enzymes, and in particular the production of proteins and/or enzymes which demonstrate less immunogenicity relative to their recombinantly-prepared counterparts. In a certain embodiments of the present invention, the lipid nanoparticles comprise polynucleotides which encode mRNA of a deficient protein or enzyme. Upon distribution of such compositions to the target tissues and the subsequent transfection of such target cells, the exogenous mRNS loaded or encapsulated into the lipid nanoparticles that comprise the blended compositions may be translated in vivo to produce a functional protein or enzyme encoded by such encapsulated mRNA (e.g., a protein or enzyme in which the subject is deficient). Accordingly, in certain embodiments the compositions of the present invention exploit a subject's ability to translate exogenously- or recombinantly-prepared mRNA to produce an endogenously-translated protein or enzyme, and thereby produce (and where applicable excrete) a functional protein or enzyme. The expressed mRNA and/or translated proteins or enzymes produced therefrom may also be characterized by the in vivo inclusion of native post-translational modifications which may often be absent in recombinantly-prepared proteins or enzymes, thereby further reducing the immunogenicity of the translated protein or enzyme.

The encapsulation of mRNA in the lipid nanoparticles and the administration of the blended pharmaceutical compositions comprising such lipid nanoparticles avoids the need to deliver the mRNA to specific organelles within a target cell (e.g., mitochondria). Rather, upon transfection of a target cell and delivery of the encapsulated mRNA to the cytoplasm of the target cell, the mRNA contents of the lipid nanoparticles may be translated and a functional protein or enzyme produced and/or excreted.

The present invention also contemplates the discriminatory targeting of one or more target cells and tissues by both passive and active targeting means. The phenomenon of passive targeting exploits the natural distributions patterns of lipid nanoparticles in vivo without relying upon the use of additional excipients or means to enhance recognition of the lipid nanoparticle by one or more target cells. For example, lipid nanoparticles which are subject to phagocytosis by the cells of the reticulo-endothelial system are likely to accumulate in the liver or spleen, and accordingly may provide means to passively direct the delivery of the compositions to such target cells.

Alternatively, the present invention contemplates active targeting, which involves the use of additional excipients, referred to herein as "targeting ligands" that may be bound (either covalently or non-covalently) to the lipid nanoparticle to encourage localization of such lipid nanoparticle at certain target cells or target tissues. For example, targeting may be mediated by the inclusion of one or more endogenous targeting ligands (e.g., apolipoprotein E) in or on the lipid nanoparticle to encourage distribution to the target cells or tissues. Recognition of the targeting ligand by the target tissues actively facilitates tissue distribution to, and cellular uptake of the lipid nanoparticle and/or their contents by the target cells and tissues. For example, in certain embodiments, one or more of the lipid nanoparticles that comprise the blended pharmaceutical formulation may comprise an apolipoprotein-E targeting ligand in or on such lipid nanoparticles to facilitate or encourage recognition and binding of such lipid nanoparticle to endogenous low density lipoprotein receptors expressed, for example by hepatocytes. As provided herein, the composition can comprise a ligand capable of enhancing affinity of the blended compositions to one or more target cells. Targeting ligands may be linked to the outer bilayer of the lipid nanoparticle during formulation or post-formulation. These methods are well known in the art. In addition, some lipid nanoparticles may comprise fusogenic polymers such as PEAA, hemagluttinin, other lipopeptides (see U.S. patent application Ser. Nos. 08/835,281, and 60/083,294, which are incorporated herein by reference) and other features useful for in vivo and/or intracellular delivery. In other embodiments, the blended compositions of the present invention demonstrate improved transfection efficacies, and/or demonstrate enhanced selectivity towards target cells or tissues of interest. Contemplated therefore are blended compositions or lipid nanoparticles that comprise one or more ligands (e.g., peptides, aptamer, oligonucleotides, a vitamin or other molecules) that are capable of enhancing the affinity of the blended compositions or their constituent lipid nanoparticles and their polynucleotide contents to one or more target cells or tissues. Suitable ligands may optionally be bound or linked to the surface of the lipid nanoparticle. In some embodiments, the targeting ligand may span the surface of a lipid nanoparticle or be encapsulated within the lipid nanoparticle. Suitable ligands are selected based upon their physical, chemical or biological properties (e.g., selective affinity and/or recognition of target cell surface markers or features.) Cell-specific target sites and their corresponding targeting ligand can vary widely. Suitable targeting ligands are selected such that the unique characteristics of a target cell are exploited, thus allowing the composition to discriminate between target and non-target cells. For example, compositions of the present invention may bear surface markers (e.g., apolipoprotein-B or apolipoprotein-E) that selectively enhance recognition of, or affinity to hepatocytes (e.g., by receptor-mediated recognition of and binding to such surface markers). Additionally, the use of galactose as a targeting ligand would be expected to direct the compositions of the present invention to parenchymal hepatocytes, or alternatively the use of mannose containing sugar residues as a targeting ligand would be expected to direct the compositions of the present invention to liver endothelial cells (e.g., mannose containing sugar residues that may bind preferentially to the asialoglycoprotein receptor present in hepatocytes). (See Hillery A M, et al. "Drug Delivery and Targeting: For Pharmacists and Pharmaceutical Scientists" (2002) Taylor & Francis, Inc.) The presentation of such targeting ligands that have been conjugated to moieties present in the lipid nanoparticle therefore facilitate recognition and uptake of the blended compositions of the present invention by one or more target cells and tissues. Examples of suitable targeting ligands include one or more peptides, proteins, aptamers, vitamins and oligonucleotides.

As used herein, the term "subject" refers to any animal (e.g., a mammal), including, but not limited to, humans, non-human primates, rodents, and the like, to which the blended compositions and methods of the present invention may be administered. Typically, the terms "subject" and "patient" are used interchangeably herein in reference to a human subject.

The ability of the blended lipid nanoparticle compositions to synergistically enhance the expression of encapsulated polynucleotides as the production of a polypeptide or protein provides novel and more efficient means of effectuating the in vivo production of polypeptides and proteins for the treatment of a host of diseases or pathological conditions. Such blended lipid nanoparticle compositions are particularly suitable for the treatment of diseases or pathological conditions associated with the aberrant express of a protein or enzyme. For example, the successful delivery of polynucleotides such as mRNA to target organs such as the liver and in particular, to hepatocytes, can be used for the treatment and the correction of in-born errors of metabolism that are localized to the liver. Accordingly, the blended pharmaceutical compositions and related methods described herein may be employed to treat a wide range of diseases and pathological conditions, in particular those diseases which are due to protein or enzyme deficiencies. The polynucleotides encapsulated by the lipid nanoparticles that comprise the blended pharmaceutical compositions may encode a functional product (e.g., a protein, enzyme, polypeptide, peptide and/or functional RNA), and may encodes a product whose in vivo production is desired. Alternatively, the polynucleotides encapsulated by the lipid nanoparticles that comprise the blended pharmaceutical compositions may comprise an antisense oligonucleotide and following delivery of such antisense oligonucleotide to one or more target cells, the expression of targeted genes or nucleic acids modulated, synergistically reduced or eliminated.

The urea cycle metabolic disorders represent examples of such protein and enzyme deficiencies which may be treated using the methods and blended lipid nanoparticle compositions provided herein. Such urea cycle metabolic disorders include ornithine transcarbamylase (OTC) deficiency, argininosuccinate synthetase deficiency (ASD) and argininosuccinate lyase deficiency (ALD). Therefore, in some embodiments, the polynucleotides encapsulated by the lipid nanoparticles provided herein encode an enzyme involved in the urea cycle, including, for example, ornithine transcarbamylase (OTC), carbamyl phosphate synthetase (CPS), argininosuccinate synthetase 1 (ASS1) argininosuccinate lyase (ASL), and arginase (ARG).

Five metabolic disorders which result from defects in the biosynthesis of the enzymes involved in the urea cycle have been described, and include ornithine transcarbamylase (OTC) deficiency, carbamyl phosphate synthetase (CPS) deficiency, argininosuccinate synthetase 1 (ASS1) deficiency (citrullinemia), argininosuccinate lyase (ASL) deficiency and arginase deficiency (ARG). Of these five metabolic disorders, OTC deficiency represents the most common, occurring in an estimated one out of every 80,000 births.

OTC is a homotrimeric mitochondrial enzyme which is expressed almost exclusively in the liver and which encodes a precursor OTC protein that is cleaved in two steps upon incorporation into the mitchondrial matrix. (Horwich A L., et al. Cell 1984 44: 451-459). OTC deficiency is a genetic disorder which results in a mutated and biologically inactive form of the enzyme ornithine transcarbamylase. OTC deficiency often becomes evident in the first few days of life, typically after protein ingestion. In the classic severe form of OTC deficiency, within the first days of life patients present with lethargy, convulsions, coma and severe hyperammonemia, which quickly leads to a deteriorating and fatal outcome absent appropriate medical intervention. (Monish S., et al., Genetics for Pediatricians; Remedica, Cold Spring Harbor Laboratory (2005)). If improperly treated or if left untreated, complications from OTC deficiency may include developmental delay and mental retardation. OTC deficient subjects may also present with progressive liver damage, skin lesions, and brittle hair. In some affected individuals, signs and symptoms of OTC deficiency may be less severe, and may not appear until later in life.

The OTC gene, which is located on the short arm of the X chromosome within band Xp21.1, spans more than 85 kb and is comprised of 10 exons encoding a protein of 1062 amino acids. (Lindgren V., et al. Science 1984; 226: 698-7700; Horwich, A L., et al. Science 224: 1068-1074, 1984; Horwich, A L. et al., Cell 44: 451-459, 1986; Hata, A., et al., J. Biochem. 100: 717-725, 1986, which are incorporated herein by reference). The OTC enzyme catalyzes the conversion or ornithine and carbamoyl phosphate to citrulline. Since OTC is on the X chromosome, females are primarily carriers while males with nonconservative mutations rarely survive past 72 hours of birth.

In healthy subjects, OTC is expressed almost exclusively in hepatocellular mitochondria. Although not expressed in the brain of healthy subjects, OTC deficiency can lead to neurological disorders. For example, one of the usual symptoms of OTC deficiency, which is heterogeneous in its presentation, is hyperammonaemic comp (Gordon, N., Eur J Paediatr Neuro 2003; 7:115-121.).

OTC deficiency is very heterogeneous, with over 200 unique mutations reported and large deletions that account for approximately 10-15 of all mutations, while the remainder generally comprises missense point mutations with smaller numbers of nonsense, splice-site and small deletion mutations. (Monish A., et al.) The phenotype of OTC deficiency is extremely heterogeneous, which can range from acute neonatal hyperammonemic coma to asymptomatic hemizygous adults. (Gordon N. Eur J Paediatr Neurol 2003; 7: 115-121). Those mutations that result in severe and life threatening neonatal disease are clustered in important structural and functional domains in the interior of the protein at sites of enzyme activity or at the interchain surface, while mutations associated with late-onset disease are located on the protein surface (Monish A., et al.) Patients with milder or partial forms of OTC deficiency may have onset of disease later in life, which may present as recurrent vomiting, neurobehavioral changes or seizures associated with hyperammonemia.

The blended lipid nanoparticle compositions and related methods of the present invention are broadly applicable to the delivery of polynucleotides, and in particular mRNA, to treat a number of disorders. In particular, the blended lipid nanoparticle compositions and related methods of the present invention are suitable for the treatment of diseases or disorders relating to the deficiency of proteins and/or enzymes. In certain embodiments, the lipid nanoparticle-encapsulated polynucleotides encode functional proteins or enzymes that are excreted or secreted by one or more target cells into the surrounding extracellular fluid (e.g., mRNA encoding hormones and neurotransmitters). Alternatively, in another embodiment, the polynucleotides of the present invention encode functional proteins or enzymes that remain in the cytosol of one or more target cells (e.g., mRNA encoding enzymes associated with urea cycle metabolic disorders or an enzyme associated with a lysosomal storage disorder). Other disorders for which the blended lipid nanoparticle pharmaceutical compositions and related methods of the present invention are useful include, but are not limited to, disorders such as SMN1-related spinal muscular atrophy (SMA); amyotrophic lateral sclerosis (ALS): GALT-related galactosemia; Cystic Fibrosis (CF); SLC3A1-related disorders including cystinuria; COL4A5-related disorders including Alport syndrome; galactocerebrosidase deficiencies; X-linked adrenoleukodystrophy and adrenomyeloneuropathy; Friedreich's ataxia; Pelizaeus-Merzbacher disease; TSC1 and TSC2-related turberous sclerosis; Sanfilippo B syndrome (MPS IIIB); CTNS-related cystinosis; the FMR1-related disorders which include Fragile X-Associated Tremor/Ataxia Syndrome and Fragile X Premature Ovarian Failure Syndrome; Prader-Willi syndrome; Fabry disease; hereditary hemorrhagic telangiectasia (AT); Niemann-Pick disease Type C1; the neuronal ceroid lipofuscinoses-related diseases including Juvenile Neuronal Ceroid Lipofuscinosis (JNCL), Juvenile Batten disease, Santavuori-Haltia disease, Jansky-Bielschowsky disease, ad PTT-1 and TPP1 deficiencies; EIF2B1, EIF2B2, EIF2B3, EIF2B4 and EIF2B5-related childhood ataxia with central nervous system hypomyelination/vanishing white matter; CACNA1A and CACNB4-related Episodic Ataxia Type 2; the MECP2-related disorders including Classic Rett Syndrome, MECP2-related Severe Neonatal Encephalopathy and PPM-X Syndrome; CDKL5-related Atypical Rett Syndrome; Kennedy's disease (SBMA); Notch-3 related cerebral autosomal dominant arteriopathy with subcortical infarcts and leukoencephalopathy (CADASIL); SCN1A and SCN1B-related seizure disorders; the Polymerase G-related disorders which include Alpers-Huttenlocher syndrome, POLG-related sensory ataxic neuropathy, dysarthria, and ophthalmoparesis, and autosomal dominant and recessive progressive external ophthalmoplegia with mitochondrial DNA deletions; X-Linked adrenal hypoplasia; X-linked agammaglobulinemia; and Wilson's disease. In certain embodiments, the polynucleotides, and in particular mRNA, of the present invention may encode functional proteins or enzymes. For example, the compositions of the present invention may include mRNA encoding agalsidase alfa, erythropoietin, α1-antitrypsin, carboxypeptidase N, alpha-L-iduronidase, iduronate-2-sulfatase, N-acetylglucosamine-1-phosphate transferase, N-acetylglucosaminidase, alpha-glucosaminide acetyltransferase, N-acetylglucosamine 6-sulfatase, N-acetylgalactosamine-4-sulfatase, beta-glucosidase, galactose-6-sulfate sulfatase, beta-galactosidase, beta-glucuronidase, glucocerebrosidase, heparan sulfamidase, hyaluronidase and galactocerebrosidase or human growth hormone.

Alternatively the encapsulated polynucleotides may encode full length antibodies or smaller antibodies (e.g., both heavy and light chains) to confer immunity to a subject. Certain embodiments of the present invention relate to blended lipid nanoparticle pharmaceutical compositions and methods of using the same to conferring immunity to a subject (e.g., via the translation of mRNA nucleic acids encoding functional antibodies), the inventions disclosed herein and contemplated hereby are broadly applicable. In an alternative embodiment the blended composition of the present invention encode antibodies that may be used to transiently or chronically effect a functional response in subjects. For example, the encapsulated mRNA may encode a functional monoclonal or polyclonal antibody, which upon translation (and as applicable, systemic excretion from the target cells) may be useful for targeting and/or inactivating a biological target (e.g., a stimulatory cytokine such as tumor necrosis factor). Similarly, the encapsulated mRNA may encode, for example, functional anti-nephritic factor antibodies useful for the treatment of membranoproliferative glomerulonephritis type II or acute hemolytic uremic syndrome, or alternatively may encode anti-vascular endothelial growth factor (VEGF) antibodies useful for the treatment of VEGF-mediated diseases, such as cancer.

The blended pharmaceutical compositions may be administered to a subject. In some embodiments, the blended compositions or the constituent lipid nanoparticles are formulated in combination with one or more additional polynucleotides, carriers, targeting ligands or stabilizing reagents, or in blended pharmacological compositions where such compositions comprise other suitable excipients. For example, in certain embodiments, the lipid nanoparticles that comprise the blended compositions may be prepared to deliver nucleic acids (e.g., mRNA) encoding two or more distinct proteins or enzymes. Alternatively, the blended lipid nanoparticle compositions of the present invention may be prepared to deliver a single polypeptide in two or more lipid nanoparticles, each having distinct lipid compositions and that are subsequently blended into a single formulation or dosage form and administered to a subject. Techniques for formulation and administration of drugs may be found in "Remington's Pharmaceutical Sciences," Mack Publishing Co., Easton, Pa., latest edition.

A wide range of molecules that can exert pharmaceutical or therapeutic effects can be delivered to target cells using the blended lipid nanoparticle compositions and methods of the present invention. The molecules can be organic or inorganic. Organic molecules can be peptides, proteins, carbohydrates, lipids, sterols, nucleic acids (including peptide nucleic acids), or any combination thereof. A formulation for delivery into target cells can comprise more than one type of molecule, for example, two different polynucleotide sequences encoding a protein, an enzyme and/or a steroid.

The blended lipid nanoparticle compositions of the present invention may be administered and dosed in accordance with current medical practice, taking into account the clinical condition of the subject, the site and method of administration, the scheduling of administration, the subject's age, sex, body weight and other factors relevant to clinicians of ordinary skill in the art. The "effective amount" for the purposes herein may be determined by such relevant considerations as are known to those of ordinary skill in experimental clinical research, pharmacological, clinical and medical arts, recognizing that blended lipid nanoparticle compositions are capable of synergistically enhancing the expression of the encapsulated polynucleotides and the production of polypeptides or proteins encoded thereby or modulating the expression of a target nucleic acid or polynucleotide (e.g., using an antisense oligonucleotide), and that in some instances dosage reductions of such encapsulated polynucleotides relative to traditional non-blended formulation may be warranted. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient expression of the one or more polynucleotides in the target cells.

The synergistic enhancements in expression of encapsulated polynucleotides that characterize the blended lipid nanoparticle formulations of the present invention allow therapeutically effective concentrations of polypeptides produced upon the expression of such encapsulated polynucleotides (e.g., a therapeutic protein or enzyme) to be achieved in the targeted tissues (or serum if the product is excreted by target cell) using a significantly lower dose of polynucleotide than was previously anticipated. Accordingly, in certain embodiments, the effective amount of a polynucleotide required to achieve a desired therapeutic effect may be reduced by encapsulating such polynucleotide in one or more lipid nanoparticles and blending at least two lipid nanoparticles. Also contemplated are methods of reducing the amount of a polynucleotide required to elicit a therapeutic effect in a subject. Such methods generally comprise a step of administering a pharmaceutical composition to the subject, wherein the pharmaceutical composition comprises a first lipid nanoparticle blended with a second lipid nanoparticle, and wherein one or both of the first lipid nanoparticle and the second lipid nanoparticle comprise the polynucleotide, followed by the transfection of one or more target cells of the subject with such polynucleotides, such that the amount of the polynucleotide required to effectuate a therapeutic effect is reduced (e.g., reduced relative to the amount of polynucleotide required to effectuate a therapeutic effect using a non-blended composition or other standard techniques). In certain embodiments, the amount of a polynucleotide required to effectuate a therapeutic effect is reduced by at least about 10%, 15%, 20%, 25%, 30%, 40%, 50%, 60%, 75%, 80%, 90%, 95% or 99%. In certain embodiments, the amount of a polynucleotide required to effectuate a therapeutic effect is reduced by at least two-, three-, four-, five-, six-, seven-, ten-, twelve-, fifteen-, twenty- or twenty-five-fold or more.

Suitable routes of administration of the blended lipid nanoparticle compositions include, for example, oral, rectal, vaginal, transmucosal, sublingual, subdural, nasally, or intestinal administration; parenteral delivery, including intramuscular, subcutaneous, untramedullary injections, as well as intrathecal, direct intraventricular, intravenous, intraperitoneal, intranasal, opthalmically or intraocular injections or infusions. In certain embodiments, the administration of the blended lipid nanoparticle composition to a subject facilitates the contacting of the constituent lipid nanoparticles to one or more target cells, tissues or organs.

Alternately, the blended lipid nanoparticle compositions of the present invention may be administered in a local rather than systemic manner, for example, via injection or infusion of the blended pharmaceutical composition directly into a targeted tissue, preferably in a depot or sustained release formulation, such that the contacting of the targeted cells with the constituent lipid nanoparticles may further facilitated. Local delivery can be affected in various ways, depending on the tissue to be targeted. For example, aerosols containing compositions of the present invention can be inhaled (for nasal, tracheal, or bronchial delivery); blended compositions of the preset invention can be injected into the site of injury, disease manifestation, or pain, for example; blended compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing blended compositions of the present invention complexed with therapeutic molecules or ligands can even be surgically administered, for example in association with a polymer or other structure or substance that can allow the compositions to diffuse from the site of implantation to surrounding cells. Alternatively, such blended compositions can be applied surgically without the use of polymers or supports.

In certain embodiments, the blended compositions of the present invention are formulated such that they are suitable for extended-release of the polynucleotides or nucleic acids encapsulated in the constituent lipid nanoparticles. Such extended-release blended compositions may be conveniently administered to a subject at extended dosing intervals. For example, in certain embodiments, the compositions of the present invention are administered to a subject twice day, daily or every other day. In a certain embodiments, the compositions of the present invention are administered to a subject twice a week, once a week, every ten days, every two weeks, every three weeks, or more preferably every four weeks, once a month, every six weeks, every eight weeks, every other month, every three months, every four months, every six months, every eight months, every nine months or annually. Also contemplated are compositions and lipid nanoparticles which are formulated for depot administration (e.g., intramuscularly, subcutaneously, intravitreally) to either deliver or release a polynucleotide (e.g., mRNA) over extended periods of time. Preferably, the extended-release means employed are combined with modifications (e.g., chemical modifications) introduced into the polynucleotides to enhance stability.

Also contemplated herein are lyophilized pharmaceutical compositions comprising one or more of the compounds disclosed herein and related methods for the use of such lyophilized compositions as disclosed for example, in U.S. Provisional Application No. PCT/US2012/041663, filed Jun. 8, 2011, the teachings of which are incorporated herein by reference in their entirety.

While certain compounds, compositions and methods of the present invention have been described with specificity in accordance with certain embodiments, the following examples serve only to illustrate the compounds of the invention and are not intended to limit the same. Each of the publications, reference materials and the like referenced herein to describe the background of the invention and to provide additional detail regarding its practice are hereby incorporated by reference in their entirety.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduces into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications and other reference materials referenced herein to describe the background of the invention and to provide additional detail regarding its practice are hereby incorporated by reference.

EXAMPLES

The following examples generally relate to lipid nanoparticle pharmaceutical compositions and formulations, and in particular pharmaceutical compositions and formulations which comprise "blends" of such lipid nanoparticles, as well as highly efficacious methods of using the foregoing pharmaceutical compositions and formulations to deliver polynucleotide constructs to one or more target cells, tissues and organs.

Example 1. Formulations and Messenger RNA Material

Lipid Materials

The formulations described herein include a multi-component lipid mixture of varying ratios employing one or more cationic lipids, helper lipids and PEGylated lipids designed to encapsulate various nucleic acid-based materials. Cationic lipids can include, but are not limited to, DOTAP (1,2-dioleyl-3-trimethylammonium propane), DODAP (1,2-dioleyl-3-dimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" *J. Contr. Rel.* 2005, 107, 276-287), DLin-KC2-DMA (Semple, S. C. et al, "Rational Design of Cationic Lipids for siRNA Delivery" *Nature Biotech.* 2010, 28, 172-176), C12-200 (Love, K. T. et al. "Lipid-like materials for low-dose in vivo gene silencing" *PNAS* 2010, 107, 1864-1869), HGT4003, ICE, dialkylamino-based, imidazole-based or guanidinium-based. Other nanoparticle components may include, but are not limited to, DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DPPE (1,2-dipalmitoyl-sn-glycero-3-phosphoethanolamine), DMPE (1,2-dimyristoyl-sn-glycero-3-phosphoethanolamine), DOPG (,2-dioleoyl-sn-glycero-3-phospho-(1'-rac-glycerol)), or cholesterol. The PEGylated lipids may include, but are not limited to, a poly(ethylene) glycol chain of up to 5 kDA in length covalently attached to a lipid with alkyl chain(s) of $C_6$-$C_{20}$ length.

Messenger RNA Material

Codon-optimized firefly luciferase messenger RNA (CO-FFL mRNA), galactose-1-phosphate uridyl transferase (GALT) and human erythropoietin (EPO) were synthesized by in vitro transcription from a plasmid DNA template encoding the gene, which was followed by the addition of a 5' cap structure (Cap1) (Fechter, P.; Brownlee, G. G. "Recognition of mRNA cap structures by viral and cellular proteins" *J. Gen. Virology* 2005, 86, 1239-1249) and a 3' poly(A) tail of approximately 200 nucleotides in length as determined by gel electrophoresis. 5' and 3' untranslated regions present in each mRNA product are represented as X and Y, respectively and defined as stated.

```
CO-FF Luciferase mRNA:
                                                        (SEQ ID NO: 1)
XAUGGAAGAUGCCAAAAACAUUAAGAAGGGCCCAGCGCCAUUCUACCCACUCGAAGACGGG
ACCGCCGGCGAGCAGCUGCACAAAGCCAUGAAGCGCUACGCCCUGGUGCCCGGCACCAUCG
CCUUUACCGACGCACAUAUCGAGGUGGACAUUACCUACGCCGAGUACUUCGAGAUGAGCGU
UCGGCUGGCAGAAGCUAUGAAGCGCUAUGGGCUGAAUACAAACCAUCGGAUCGUGGUGUGC
AGCGAGAAUAGCUUGCAGUUCUUCAUGCCCGUGUUGGGUGCCCUGUUCAUCGGUGUGGCUG
UGGCCCCAGCUAACGACAAUCUACAACGAGCGCGAGCUGCUGAACAGCAUGGGCAUCAGCCA
GCCCACCGUCGUAUUCGUGAGCAAGAAAGGGCUGCAAAAGAUCCUCAACGUGCAAAAGAAG
CUACCGAUCAUACAAAAGAUCAUCAUCAUGGAUAGCAAGACCGACUACCAGGGCUUCCAAA
GCAUGUACACCUUCGUGACUUCCCAUUUGCCACCCGGCUUCAACGAGUACGACUUCGUGCC
CGAGAGCUUCGACCGGGACAAAACCAUCGCCCUGAUCAUGAACAGUAGUGGCAGUACCGGA
UUGCCCAAGGGCGUAGCCCUACCGCACCGCACCGCUUGUGUCCGAUUCAGUCAUGCCCGCG
ACCCCAUCUUCGGCAACCAGAUCAUCCCCGACACCGCUAUCCUCAGCGUGGUGCCAUUUCA
CCACGGCUUCGGCAUGUUCACCACGCUGGGCUACUUGAUCUGCGGCUUUCGGGUCGUGCUC
AUGUACCGCUUCGAGGAGGAGCUAUUCUUGCGCAGCUUGCAAGACUAUAAGAUUCAAUCUG
CCCUGCUGGUGCCCACACUAUUUAGCUUCUUCGCUAAGAGCACUCUCAUCGACAAGUACGA
CCUAAGCAACUUGCACGAGAUCGCCAGCGGCGGGGCGCCGUCAGCAAGGAGGUAGGUGAG
GCCGUGGCCAAACGCUUCCACCUACCAGGCAUCCGCCAGGGCUACGGCCUGACAGAAACAA
CCAGCGCCAUUCUGAUCACCCCCGAAGGGGACGACAAGCCUGGCGCAGUAGGCAAGGUGGU
GCCCUUCUUCGAGGCUAAGGUGGUGGACUUGGACACCGGUAAGACACUGGGGUGUGAACCAG
CGCGGCGAGCUGUGCGUCCGUGGCCCCAUGAUCAUGAGCGGCUACGUUAACAACCCCGAGG
CUACAAACGCUCUCAUCGACAAGGACGGCUGGCUGCACAGCGGCGACAUCGCCUACUGGGA
CGAGGACGAGCACUUCUUCAUCGUGGACCGGCUGAAGAGCCUGAUCAAAUACAAGGGCUAC
CAGGUAGCCCCAGCCGAACUGGAGAGCAUCCUGCUGCAACACCCCAACAUCUUCGACGCCG
GGGUCGCCGGCCUGCCCGACGACGAUGCCGGCGAGCUGCCCGCCGCAGUCGUCGUGCUGGA
ACACGGUAAAACCAUGACCGAGAAGGAGAUCGUGGACUAUGUGGCCAGCCAGGUUACAACC
GCCAAGAAGCUGCGCGGUGGUGUUGUGUUCGUGGACGAGGUGCCUAAAGGACUGACCGGCA
AGUUGGACGCCCGCAAGAUCCGCGAGAUUCUCAUUAAGGCCAAGAAGGGCGGCAAGAUCGC
CGUGUAAY
```

-continued

Human GALT mRNA:
(SEQ ID NO: 2)
XAUGUCGCGCAGUGGAACCGAUCCUCAGCAACGCCAGCAGGCGUCAGAGGCGGACGC
CGCAGCAGCAACCUUCCGGGCAAACGACCAUCAGCAUAUCCGCUACAACCCGCUGCA
GGAUGAGUGGGUGCUGGUGUCAGCUCACCGCAUGAAGCGGCCCUGGCAGGGUCAAGU
GGAGCCCCAGCUUCUGAAGACAGUGCCCCGCCAUGACCCUCUCAACCCUCUGUGUCC
UGGGGCCAUCCGAGCCAACGGAGAGGUGAAUCCCCAGUACGAUAGCACCUUCCUGUU
UGACAACGACUUCCUAGCUCUGCAGCCUGAUGCCCCCAGUCCAGGACCCAGUGAUCA
UCCCCUUUUCCAAGCAAAGUCUGCUCGAGGAGUCUGUAAGGGCAUGUGCUUCCACCC
CUGGUCGGAUGUAACGCUGCCACUCAUGUCGGUCCCUGAGAUCCGGGCUGUUGUUGA
UGCAUGGGCCUCAGUCACAGAGGAGCUGGGUGCCCAGUACCCUUGGGUGCAGAUCUU
UGAAAACAAAGGUGCCAUGAUGGGCUGUUCUAACCCCCACCCCCACUGCCAGGUAUG
GGCCAGCAGUUUCCUGCCAGAUAUUGCCCAGCGUGAGGAGCGAUCUCAGCAGGCCUA
UAAGAGUCAGCAUGGAGAGCCCCUGCUAAUGGAGUACAGCCGCCAGGAGCUACUCAG
GAAGGAACGUCUGGUCCUAACCAGUGAGCACUGGUUAGUACUGGUCCCCUUCUGGGC
AACAUGGCCCUACCAGACACUGCUGCUGCCCCGUCGGCAUGUGCGGCGGCUACCUGA
GCUGACCCCUGCUGAGCGUGAUGAUCUAGCCUCCAUCAUGAAGAAGCUCUUGACCAA
GUAUGACAACCUCUUUGAGACGUCCUUUCCCUACUCCAUGGGCUGGCAUGGGGCUCC
CACAGGAUCAGAGGCUGGGGCCAACUGGAACCAUUGGCAGCUGCACGCUCAUUACUA
CCCUCCGCUCCUGCGCUCUGCCACUGUCCGGAAAUUCAUGGUUGGCUACGAAAUGCU
UGCUCACGCUCAGAGGGACCUCACCCCUGAGCAGGCUGCAGAGAGACUAAGCGCACU
UCCUGAGGUUCAUUACCACCUGGGGCAGAAGGACAGGGAGACAGCAACCAUCGCCUG
AY Human EPO mRNA:
(SEQ ID NO: 3)
XAUGGGGGUGCACGAAUGUCCUGCCUGGCUGUGGCUUCUCCUGUCCCUGCUGUCGCU
CCCUCUGGGCCUCCCAGUCCUGGGCGCCCCACCACGCCUCAUCGUGACAGCCGAGU
CCUGGAGAGGUACCUCUUGGAGGCCAAGGAGGCCGAGAAUAUCACGACGGGCUGUGC
UGAACACUGCAGCUUGAAUGAGAAUAUCACUGUCCCAGACACCAAAGUUAAUUUCUA
UGCCUGGAAGAGGAUGGAGGUCGGGCAGCAGGCCGUAGAAGUCUGGCAGGGCCUGGC
CCUGCUGUCGGAAGCUGUCCUGCGGGGCCAGGCCCUGUUGGUCAACUCUUCCCAGCC
GUGGGAGCCCCUGCAGCUGCAUGUGGAUAAAGCCGUCAGUGGCCUUCGCAGCCUCAC
CACUCUGCUUCGGGCUCUGGGAGCCCAGAAGGAAGCCAUCUCCCCUCCAGAUGCGGC
CUCAGCUGCUCCACUCCGAACAAUCACUGCUGACACUUUCCGCAAACUCUUCCGAGU
CUACUCCAAUUUCCUCCGGGGAAAGCUGAAGCUGUACACAGGGGAGGCCUGCAGGAC
AGGGGACAGAUGAY 5' and 3' UTR Sequences
(SEQ ID NO: 4)
X = GGGAUCCUACC
or (SEQ ID NO: 5)
GGACAGAUCGCCUGGAGACGCCAUCCACGCUGUUUUGACCUCCAUAGAAGACACCGG
GACCGAUCCAGCCUCCGCGGCCGGGAACGGUGCAUUGGAACGCGGAUUCCCCGUGCC
AAGAGUGACUCACCGUCCUUGACACG (SEQ ID NO: 6)
Y = UUUGAAUU
or (SEQ ID NO: 7)
CGGGUGGCAUCCCUGUGACCCCUCCCCAGUGCCUCUCCUGGCCCUGGAAGUUGCCAC
UCCAGUGCCCACCAGCCUUGUCCUAAUAAAAUUAAGUUGCAUC Exemplary Formulation Protocol Lipid nanoparticles (LNP) were formed via standard ethanol injection methods (Ponsa, M.; Foradada, M.; Estelrich, J. "Liposomes obtained by the ethanol injection method" Int. J. Pharm. 1993, 95, 51-56). Ethanolic stock solutions of the lipids were prepared ahead of time at 50 mg/mL and stored at −20° C. FFL mRNA was stored in water at a final concentration of 1 mg/mL at −80° C. until the time of use. All mRNA concentrations were determined via the Ribogreen assay (Invitrogen). Encapsulation of mRNA was calculated by performing the Ribogreen assay with and without the presence of 0.1% Triton-X 100. Particle sizes (dynamic light scattering (DLS)) and zeta potentials were determined using a Malvern Zetasizer instrument in 1×PBS and 1 mM DCl solutions, respectively.

Formulation Example 1

Aliquots of 50 mg/mL ethanolic solutions of the imidazole-based cationic lipid ICE, DOPE and DMG-PEG2K were mixed and diluted with ethanol to 3 mL final volume. Separately, an aqueous buffered solution (10 mM citrate/150 mM NaCl, pH 4.5) of FFL mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=1.73 mg/mL CO-FF mRNA (encapsulated). $Z_{ave}$=68.0 nm ($Dv_{(50)}$=41.8 nm; $Dv_{(90)}$=78.0 nm). Zeta potential=+25.7 mV.

Formulation Example 2

Aliquots of 50 mg/mL ethanolic solutions of DLinKC2DMA, DOPE, cholesterol and DMG-PEG2K were mixed and diluted with ethanol to 3 mL final volume. Separately, and aqueous buffered solutions (10 mM acetate, pH 6.5) of FFL mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS) (pH 7.4), concentrated and stored at 2-8° C. Final concentration=3.47 mg/mL CO-FF mRNA (encapsulated). $Z_{ave}$=74.3 nm ($Dv_{(50)}$=58.6 nm; $Dv_{(90)}$=95.2 nm).

All formulations were made in accordance to the procedure described in Formulation Example 1, with the exception of DLinKC2DMA formulations, which were formulated according to Formulation Example 2. Various exemplary lipid nanoparticle formulation, are disclosed in Table 1. All lipid ratios are calculated as mol percentage.

Example 2. Injection Protocol and Assays for Expression and Biodistribution In Vivo Injection Protocol All studies were performed using male or female CD-1 mice of approximately 6-8 weeks of age at the beginning of each experiment. Samples were introduced by a single bolus tail-vein injection or intracerebroventricular (ICV) administration of an equivalent total dose of encapsulated FFL mRNA up to a dose of 230 micrograms. Four hours post-injection the mice were sacrificed and perfused with saline.

TABLE 1

Exemplary Lipid Nanoparticle Formulations.

| Lipid Formulation (Total Component) | Lipid Ratio (mol %) | N/P Ratio |
|---|---|---|
| C12-200:DOPE:CHOL:DMGPEG2K | 40:30:25:5 | 4 |
| C12-200:DOPE:CHOL:DMGPEG2K | 40:30:20:10 | 4 |
| C12-200:DOPE:CHOL:DMGPEG2K | 40:30:20:10 | 2 |
| C12-200:DOPE:CHOL:DMGPEG2K | 25:35:30:10 | 2 |
| DLin-KC2-DMA:DOPE:CHOL:DMGPEG2K | 50:25:20:5 | 5 |
| DLin-KC2-DMA:DOPE:CHOL:DMGPEG2K | 50:20:20:10 | 5 |
| HGT4003:DOPE:Chol:DMGPEG2K | 70:10:10:10 | 5 |
| HGT4003:DOPE:Chol:DMGPEG2K | 25:35:30:10 | 5 |
| HGT4003:DOPE:Chol:DMGPEG2K | 50:25:20:5 | 5 |
| HGT4003:DOPE:Chol:DMGPEG2K | 40:30:20:10 | 5 |
| ICE:DOPE:DMGPEG2K | 90:5:5 | 16 |
| ICE:DOPE:DMGPEG2K | 70:20:10 | 16 |
| ICE:DOPE:DMGPEG2K | 70:25:5 | 16 |
| ICE:DOPE:DMGPEG2K | 90:5:5 | 8 |
| ICE:DOPE:DMGPEG2K | 70:20:10 | 8 |
| ICE:DOPE:DMGPEG2K | 70:25:5 | 8 |
| DODAP:DOPE:Chol:DMGPEG2K | 18:57:20:5 | 4 |
| DODAP:DOPE:Chol:DMGPEG2K | 18:56:20:6 | 4 |
| DODAP:DOPE:Chol:DMGPEG2K | 18:52:20:10 | 4 |
| DLin-KC2-DMA:C12-200:DOPE:CHOL:DMGPEG2K | 30:20:25:20:5 | 5 |
| C12-200:DOPE:ICE:DMGPEG2K | 40:30:20:10 | 4 |
| C12-200:DOPE:ICE:DMGPEG2K | 40:30:20:10 | 2 |
| C12-200:ICE:DMGPEG2K | 20:70:10 | 4 |
| DODAP:DOPE:ICE:DMGPEG2K | 18:57:20:5 | 4 |
| DODAP:DOPE:ICE:DMGPEG2K | 18:37:40:5 | 4 |

"Blended" Formulation:

A portion of one cationic lipid formulation was combined with a separate aliquot of a different cationic lipid formulation in a desired ratio, based on encapsulated mRNA concentrations and dosed accordingly "Mixed" Formulations:

A single formulation synthesized from a previously combined organic solution of helper lipids, PEGylated lipids and multiple, non-identical cationic/ionizable lipids.

As used herein, the term "blend" refers to a combination of two or more separate, non-identical formulations. Typically, the two or more separate, non-identical formulations are combined or blended into one composition, such as, a suspension, as depicted, for example, in FIG. 1. As used herein, non-identical formulations refer to formulations containing at least one distinct lipid component. In some embodiments, non-identical formulations suitable for blend contain at least one distinct cationic lipid component. The term "blend" as used herein is distinguishable from the terms "mix" or "mixture", which are used herein to define a single formulation containing multiple non-identical cationic/ionizable lipids, multiple non-identical helper lipids, and/or multiple non-identical PEGylated lipids. In some embodiments, a "mix" formulation contains at least two or more non-identical cationic/ionizable lipids. Typically, a "mix" formulation contains a single homogeneous population of lipid nanoparticles.

Isolation of Organ tissues for Analysis

The liver, spleen and when applicable, the brain, of each mouse was harvested, apportioned into two parts and stored in either: (1)—10% neutral buffered formalin or; (2)—snap-frozen and stored at −80° C. for bioluminescence analysis.

Bioluminescence Assay

Tissue Homogenization

The bioluminescence assay was conducted using a Promega Luciferase Assay System (Promega). Tissue preparation was performed as follows: briefly, portions of the desired tissue sample (snap-frozen) were thawed, washed with DI water and placed in a ceramic bead homogenization tube. The tissue was treated with lysis buffer and homogenized. Upon subjection to five freeze/thaw cycles followed by centrifugation at 4° C., the supernatant was transferred to a new microcentrifuge tube and stored at −80° C.

Luciferase Assay

The Luciferase Assay Reagent was prepared by adding 10 mL of Luciferase Assay Buffer to Luciferase Assay Substrate and mixed via vortex. Twenty microliters of each homogenate was loaded onto a 96-well plate followed, along with 20 microliters of plate control. Separately, 120 microliters of Luciferase Assay Reagent was loaded into each well of a 96-well flat bottomed plate and analyzed using a Biotek Synergy 2 instrument to measure luminescence (measurements were recorded in relative light units (RLU)).

EPO Assay

Human EPO protein was detected via hEPO ELISA system (R&D Systems). Western blot analyses were performed using an anti-hEPO antibody MAB2871 (R&D Systems) and ultrapure human EPO protein (R&D Systems) as a control.

Example 3. Delivery of CO-FFL mRNA Via Lipid-Derived Nanoparticles

For the study, animals were injected intravenously with a single dose of encapsulated mRNA and sacrificed after four hours. Activity of expressed firefly luciferase protein in livers and spleens was determined using a bioluminescence assay. Detectable signal over baseline was observed for every animal tested to determine the expression of firefly luciferase protein from the exogenous mRNA.

Figure 2:
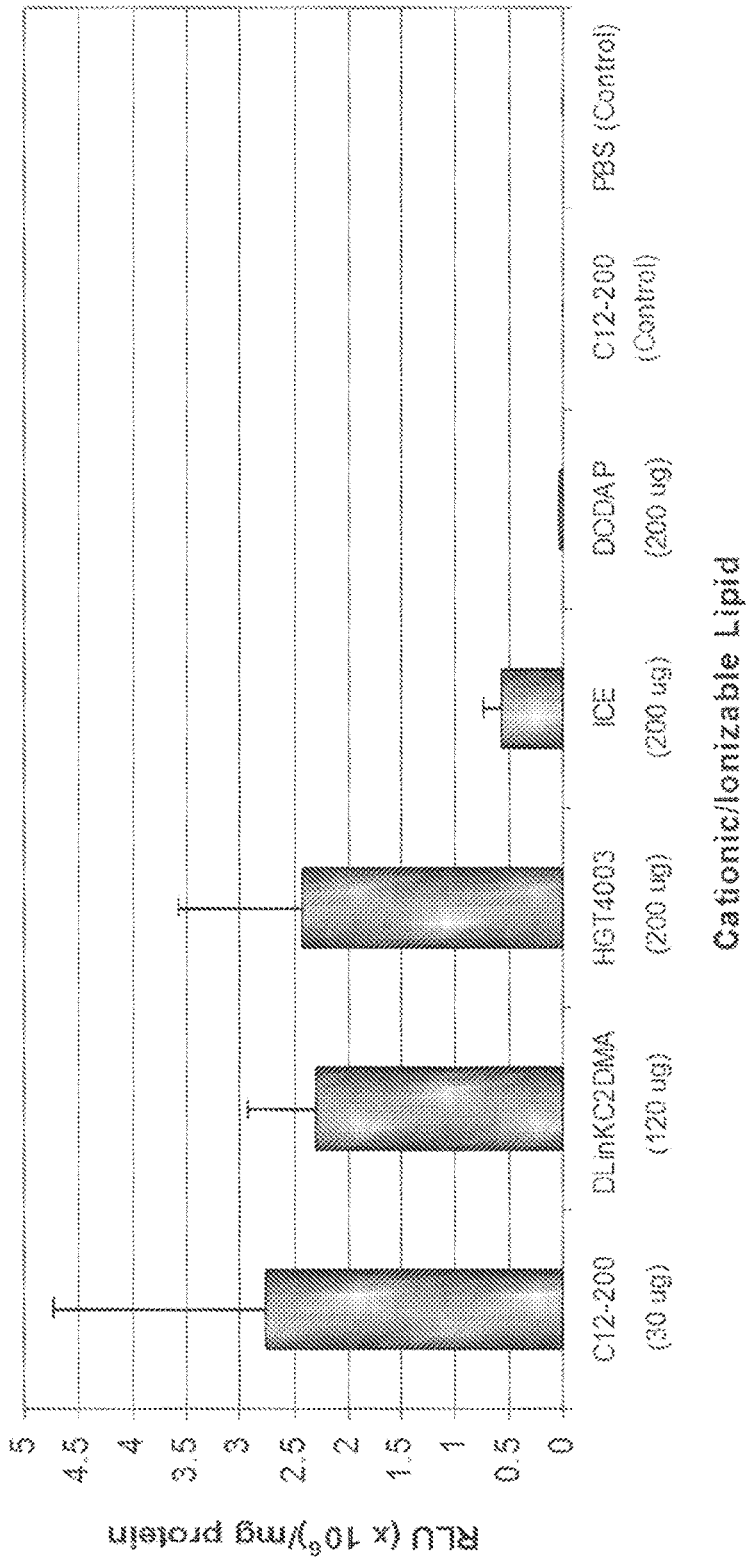
FIG. 2. illustrates the luminescence output of firefly luciferase protein in livers of mice following treatment with firefly luciferase (FFL) mRNA-encapsulated lipid nanoparticles based on various cationic lipids. Doses of encapsulated FFL mRNA evaluated were C12-200 (30 µg), DLin-KC2-DMA (90 µg), HGT4003 (200 µg) and DODAP (200 µg). The two controls included a C12-200-based cationic lipid nanoparticle encapsulating a non-fluorescent mRNA (30 µg dose) and PBS vehicle. Values are depicted as median RLU/mg of total protein in liver four hours post-administration.

As illustrated in FIG. 2, all formulations tested yielded an enhanced luminescence output with respect to different controls (e.g., non-FFL mRNA encapsulated lipid nanoparticles, empty nanoparticles and PBS). A detailed representation of the raw values of luminescence output (expressed as the median RLU/mg of total protein) from firefly luciferase protein detected in the livers of mice 4 hours following the administration of a single dose of the lipid formulations is presented in Table 2 below. The controls used in the present study included a C12-200-based cationic lipid nanoparticle encapsulating a non-fluorescent mRNA (30 μg dose) and PBS vehicle.

TABLE 2

Luminescence Output of CO-FFL Protein in Mice Liver

| Lipid Formulation (Cationic Component) | Dose of Encapsulated CO-FFL mRNA (ug) | Mean Luminescent Output (RLU/mg protein) |
|---|---|---|
| C12-200 | 30 | 2,770,000 |
| DLin-KC2-DMA | 90 | 2,280,000 |
| HGT4003 | 200 | 2,420,000 |
| ICE | 200 | 557,000 |
| DODAP | 200 | 14,000 |
| *C12-200 (Control) | 30 | 500 |
| PBS (Control/No lipid) | — | 100 |

*C12-200 control - Is a C12-200-based cationic lipid nanoparticle encapsulated 30 ug of mRNA encoding a non-fluorescent protein
— = No lipid control

Example 4. Blending of Two Separate, Non-Identical Lipid Nanoparticles, Leads to Synergistic Enhancement of Expression In order to evaluate the transfection efficiency of various lipid encapsulating formulation of CO-FFL mRNA, both mixtures and blends of various lipid nanoparticle formulations, as well as the individual constituent lipid nanoparticles were prepared ad assayed for their ability to transfect and express mRNA in various targeted cells and tissues (as determined by the luminescence of the firefly luciferase protein) in vivo.

Specifically, two lipid nanoparticle formulations encapsulating FFL mRNA and comprising either C12-200 or DLin-KC2-DMA as the cationic lipid were prepared in accordance with the formulation protocol described in Example 1 (such formulations being referred to herein as Formulations 1 and 2, respectively). A third lipid nanoparticle formulation encapsulating FFL mRNA was prepared which comprised a mixture of the cationic lipids C12-200 and DLin-KC2-DMA in a single lipid nanoparticle (referred to herein as Formulation 3). Finally, a fourth lipid nanoparticle formulation was prepared which comprised a blend of Formulations 1 and 2 in a 1:3 ratio based on the dose of encapsulated FFL mRNA (referred to herein as Formulation 4). Table 3 represents the cationic lipid component(s) of Formulations 1, 2, 3 and 4, as well as the total dose of encapsulated FFL mRNA.

TABLE 3

Liver Fluorescence Intensity for Single, Mixed and Blended Lipid Formulations

| Formulation | Lipid (Cationic Component) | Dose of Encapsulated FFL mRNA (ug) | Mean Luminescent Output (RLU/mg protein) |
|---|---|---|---|
| #1 | C12-200 | 30 | 2,770,000 |
| #2 | DLin-KC2-DMA | 90 | 2,280,000 |
| #3 | C12-200/DLin-KC2-DMA "Mix" | 30 | 1,530,000 |
| #4 | "Blend" of Formulations #1 and #3 | 120 | 46,800,000 |

Raw values of mean luminescence output from FFL protein in livers of mice after treatment with FFL mRNA-loaded lipid nanoparticles demonstrating the difference between a "mixed" formulation versus a "blended" formulation. Formulation #3 represents a single formulation of "mixed" cationic lipids (30 ug dose) while formulation #4 represents a "blend" of formulations #1 and #2 as a 1:3 ratio (based on dose of encapsulated mRNA). Values are depicted as mean RLU/mg of total protein in liver four hours post-administration.

Animals were injected intravenously (via a tail-vein injection) with a single dose of FFL mRNA encapsulated in either Formulations 1, 2, 3 or 4 and sacrificed after four hours. The activity of expressed firefly luciferase mRNA in the livers and spleens of the animals was determined in a bioluminescence assay. A detectable signal over baseline was observed in every animal tested, inferring the expression the exogenously-administered encapsulated FFL mRNA and the corresponding production of the firefly luciferase protein.

A comparison of the luminescence output from FFL protein expressed in the liver upon delivery via various liposomal nanoparticles was evaluated. Luminescence from a single formulation varied in intensity based upon which cationic lipid is employed. Such luminescence can also be dependent on (but not exclusively) lipid composition, total lipid content and dose. All formulations tested, however, yielded an enhanced light output with respect to different controls (non-FFL mRNA loaded nanoparticles, empty nanoparticles, PBS, etc.) (FIG. 2). A more detailed representation of the luminescent output (raw values) of these formulations is listed in Table 3.

Figure 3:
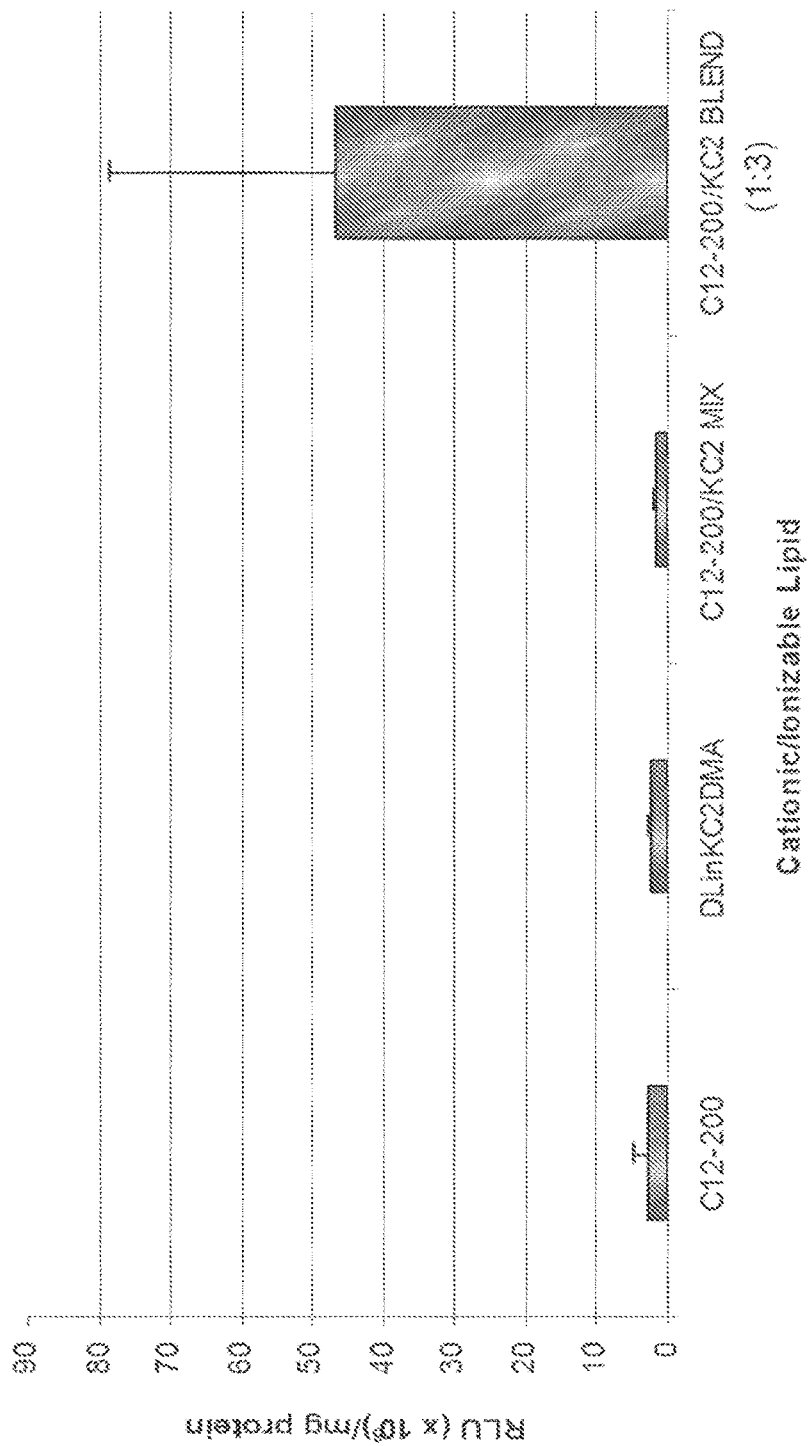
FIG. 3. illustrates the Luminescence output of firefly luciferase protein in livers of mice four hours after treatment with FFL mRNA-encapsulated lipid nanoparticles. The formulations compared were a C12-200-based formulation (30 µg dose), a DLin-KC2-DMA-based formulation (90 µg dose), a mixed $C_{12}$-200/DLin-KC2-DMA single formulation (30 µg dose) and a blend of two separate C12-200- and DLin-KC2-DMA-based formulations. As depicted by FIG. 3, the blended formulation (120 µg dose, 1:3 ratio of C12-200 encapsulated FFL mRNA:DLin-KC2-DMA encapsulated FFL mRNA, respectively) demonstrated a synergistic enhancement of luminescence.

As shown in Table 3, mixing different cationic lipids within a single formulation (C12-200, DLin-KC2-DMA) still allows for successful delivery of the desired mRNA to the target tissue with comparable overall production of protein (based on measured RLU output of FFL protein) as compared to either C12-200 or DLin-KC2-DMA based formulation. However, upon blending two separate, non-identical formulations, a synergistic (non-additive) enhancement in light output was observed (FIG. 3, Table 3). Specifically, as listed in Table 3, when blending a C12-200-based lipid nanoparticle encapsulating FFL mRNA (Formulation #1) with a DLin-KC2-DMA-based FFL mRNA-loaded lipid nanoparticle (Formulation #2) in a 1.3 ratio (30 ug FFL mRNA, respectively), one observes a mean RLU value of $46.8 \times 10^6$ RLU/mg protein (Formulation #4). This is compared to an expected additive value of $5.05 \times 10^6$ RLU/mg protein, based on the sum of each formulation tested individually ($2.77 \times 10^6$ and $2.28 \times 10^6$ RLU/mg protein for Formulation #1 and #2, respectively (FIG. 3, Table 3)). By administering a blend of the two formulations, one achieves 9-fold greater luminescent output (i.e. more efficacious production of desired protein).

On the contrary, simply mixing two lipids within one lipid nanoparticle did not result in any observable enhancement (Formulation #3, Table 3). For example, a 30 ug dose of a mixed C12-200/DLin-KC2-DMA FFL mRNA-loaded lipid nanoparticle yielded a comparable, albeit lower luminescent output than either a C12-200 or DLin-KC2-DMA FFL mRNA-loaded lipid nanoparticle alone ($1.53 \times 10^6$ RLU/mg protein vs. $2.77 \times 10^6$ and $2.28 \times 10^6$ RLU/mg protein, respectively) (FIG. 3, Table 3). When dosing such a "mix" at 120 ug, the resulting formulation was lethal. It is noteworthy that blending two separate formulations at this dose (120 ug) was well tolerated in mice after 4 hours.

The effect of mixing, was further evaluated using two additional CO-FFL mRNA lipid mixtures; C12-200/ICE FFL and DODAP/ICE FFL. When the C12-200/ICE FFL mixed formulation was dosed at 30 ug, the resulting mean luminescent output detected was $2.71 \times 10^6$ RLU/mg protein, comparable to an individual C12-200-based lipid formulation ($2.77 \times 10^6$ RLU/mg protein). The DODAP/ICE FFL mixed formulation, resulted in a mean output of 7,300 RLU/mg protein as compared to a single DODAP-based formulation (~14,000 RLU/mg protein). As stated above, a mixed formulation has yielded comparable results to single cationic lipid-based formulations but not enhanced.

Example 5. Synergy Observed Across a Variety of Different Lipid Nanoparticle Blends This example demonstrates that the synergy observed in Example 4 is not limited to specific formulations Blended. In fact, this synergy is observed across a wide variety of different lipid nanoparticles blended in various ratios. Exemplary results from various experiments are summarized in Table 4.

Specifically, multiple lipid nanoparticle formulations encapsulating FFL mRNA and comprising either C12-200, DLin-KC2-DMA, ICE, DODAP or HGT4003 as the cationic lipid were prepared in accordance with the formulation protocol described in Example 1, and subsequently blended at various ratios to prepare the blended lipid nanoparticle formulation (Table 4). In addition, the lipid formulations designated as "(A)" comprise a 5% concentration of the PEG-modified lipid DMG-PEG2000, while the lipid formulations designated as "(B)" comprise a 10% DMG-PEG2000. Animals were injected intravenously (via a tail-vein injection) with a single bolus dose of FFL mRNA encapsulated in either a blended lipid formulation of the constituent lipid formulation and sacrificed after four hours. The activity of expressed firefly luciferase mRNA in the liver was determined in a bioluminescence assay. Increases range from 1.1-10× luminescence over the sum of each respective individual formulation demonstrating a synergistic enhancement.

As shown in Table 4, each blend resulted in an increase in luminescence when delivering FFL mRNA as compared to the sum of the output of its individual formulations. Experiments #1-4 (Table 4) were similar to what has been described above (Example 4). The results shown in Table 4 also indicate that upon varying the formulation parameters (PEG percentage) for each nanoparticle, one can effectively adjust and control the amount of synergistic enhancement. Further, this synergistic enhancement in protein production can be impacted/tailored by lipid composition (other than PEGylated lipid) and total lipid content.

Another example of synergistic enhancement using different cationic lipid formulations is represented by Experiment #8. When blending a FFL mRNA-loaded HGT4003-based lipid nanoparticle with a FFL mRNA-loaded ICE-based lipid nanoparticle in a 1:1 ratio (100 ug encapsulated mRNA: 100 ug encapsulated mRNA, respectively), one observes a mean RLU/mg protein value of $4.39 \times 10^5$. This is compared to an expected additive value of $2.77 \times 10^5$ RLU/mg protein, based on the sum of each formulation tested individually (($2.53 \times 10^5$ and $2.40 \times 10^4$ RLU/mg protein, respectively (Table 4, FIG. 4)).

Figure 4:
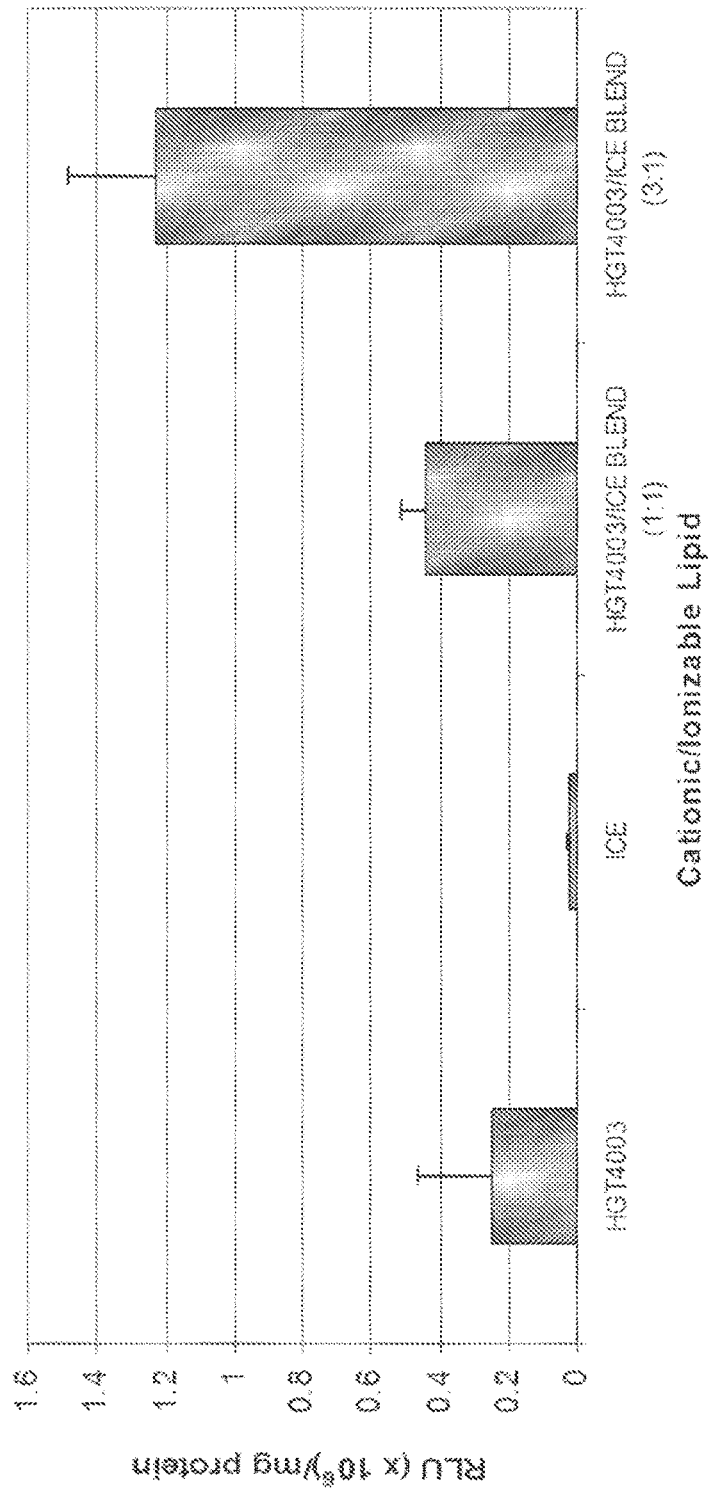
FIG. 4. illustrates a comparison of luminescence output of firefly luciferase protein in mouse livers based on two ratios of blended formulations. The individual HGT4003 and ICE formulations were dosed at 100 µg of encapsulated firefly luciferase (FFL) mRNA each. The two blended formulations were administered at a total dose of 200 µg encapsulated FFL mRNA. Values are depicted as median RLU/mg of total protein in liver four hours post-administration.

Another factor is the ratio at which the formulations are blended. As depicted in FIG. 4, two formulations encapsulating FFL mRNA are dosed individually and as blends employing two different blend ratios, 1:1 and 3:1 (HGT4003:ICE) (Table 4, Experiment #8 and #9, respectively). While a synergistic increase in luminescence is observed for both blends, one observes a much greater enhancement when the two formulations are blended in a 3:1 ratio (HGT4003:ICE). The formulations blended in a 1:1 ratio yielded a 1.59-fold enhancement over the sum of its individual counterparts, while the formulations blended in a 3:1 ratio afforded an approximate 4.4-fold enhancement.

The results described herein demonstrate that blending two separate FFL mRNA-loaded lipid nanoparticles mechanistically allows the production of more FFL protein to be produced within the mouse liver in a synergistic fashion than as compared to its separate counterparts. Without wishing to be bound by any theory, it is contemplated that possible explanations for synergy include: a.) non-competing pathways of cellular entry, b.) combination of different intracellular trafficking mechanisms (proton-sponge vs. fusogenicity, c.) "endosomal fusion" combining drug release properties with endosomal release properties (i.e., a cell can take up both separate nanoparticles and as they get processed through the endosomal pathway, the endosomes fuse and then one set of lipids enhances the other in terms of mRNA release), d.) modulation of active inhibitory pathways allowing greater uptake of nanoparticles.

TABLE 4

Various cationic lipid-nanoparticle blends and synergistic enhancement of CO-FFL protein luminescence in liver

| Experiment | Lipid Formulation #1 (FFL mRNA) | RLU/mg protein of Formulation #1 | Lipid Formulation #2 (FFL mRNA) | RLU/mg protein of Formulation #2 | Ratio | Total Dose (ug mRNA) | RLU/mg protein of Blend | Fold Increase in Luminescence |
|---|---|---|---|---|---|---|---|---|
| 1 | C12-200 (A) | 200,526 | DLin-KC2-DMA (A) | 47,231 | 1:3 | 120 | 275,275 | 3.12 |
| 2 | C12-200 (A) | 1,299,758 | DLin-KC2-DMA (B) | 26,661 | 1:3 | 120 | 2,523,496 | 1.98 |

TABLE 4-continued

Various cationic lipid-nanoparticle blends and synergistic enhancement of CO-FFL protein luminescence in liver

| Experiment | Lipid Formulation #1 (FFL mRNA) | RLU/mg protein of Formulation #1 | Lipid Formulation #2 (FFL mRNA) | RLU/mg protein of Formulation #2 | Ratio | Total Dose (ug mRNA) | RLU/mg protein of Blend | Fold Increase in Luminescence |
|---|---|---|---|---|---|---|---|---|
| 3 | C12-200 (B) | 396,134 | DLin-KC2-DMA (A) | 47,231 | 1:3 | 120 | 1,766,473 | 3.98 |
| 4 | C12-200 (B) | 396,134 | DLin-KC2-DMA (B) | 26,681 | 1:3 | 120 | 1,673,159 | 3.96 |
| 5 | C12-200 (A) | 1,062,038 | ICE | —$^a$ | 1:6.67 | 230 | 4,325,041 | 3.98 |
| 6 | C12-200 (A) | 2,101,685 | DODAP | 12,000$^c$ | 1:3 | 120 | 1,935,508 | 0 |
| 7 | DLin-KC2-DMA (A) | 1,634,139 | DODAP | 12,000$^c$ | 3:1 | 120 | 2,650,865 | 1.61 |
| 8 | HGT4003 | 252,884 | ICE | 24,134 | 1:1 | 200 | 439,228 | 1.59 |
| 9 | HGT4003 | —$^c$ | ICE | —$^b$ | 3:1 | 200 | 1,238,838 | 4.43$^d$ |
| 10 | ICE | 24,134 | DODAP | 7,649 | 1:1 | 200 | 165,230 | 3.31 |

Summary of synergistic enhancement of FFL protein luminescence in livers of treated mice (N-4) four hours post administration when blending two separate fluorescent mRNA-loaded lipid nonparticles (FFL mRNA). Increases rance from 1.1-10x luminescence over the sum of each respective individual formulation demonstrating a synergistic enhancement. The lipids listed represent the cationic component of each formulation. A formulation of (A) consists of 5% DMGPED2K while (B) incorporates 10% DMGPEG2K in the formulation. Values are representative of observable enhancement four hours post-administration. $^a$Not dosed as separate formulation this experiment. $^b$Fold increase determined using average value for ICE formulation previously measured. $^c$Historical data luminescence from previous experiment. $^d$Fold increase based on comparison of Experiment 8 as 1:1 ratio.

Example 6. Synergistic Effect is independent of nucleic acid incorporated

This synergistic enhancement of light production is even more evident when substituting non-fluorescent "dummy" mRNA (non-FFL) lipid nanoparticles as a blend component. Specifically, representative experiments incorporating mRNA encoding galactose-1-phosphate uridyl transferase (GALT) as the non-fluorescent component were performed to demonstrate the notion of synergy with respect to blending separate formulations is independent of the nucleic acid incorporated (FIG. 5).

Figure 5:
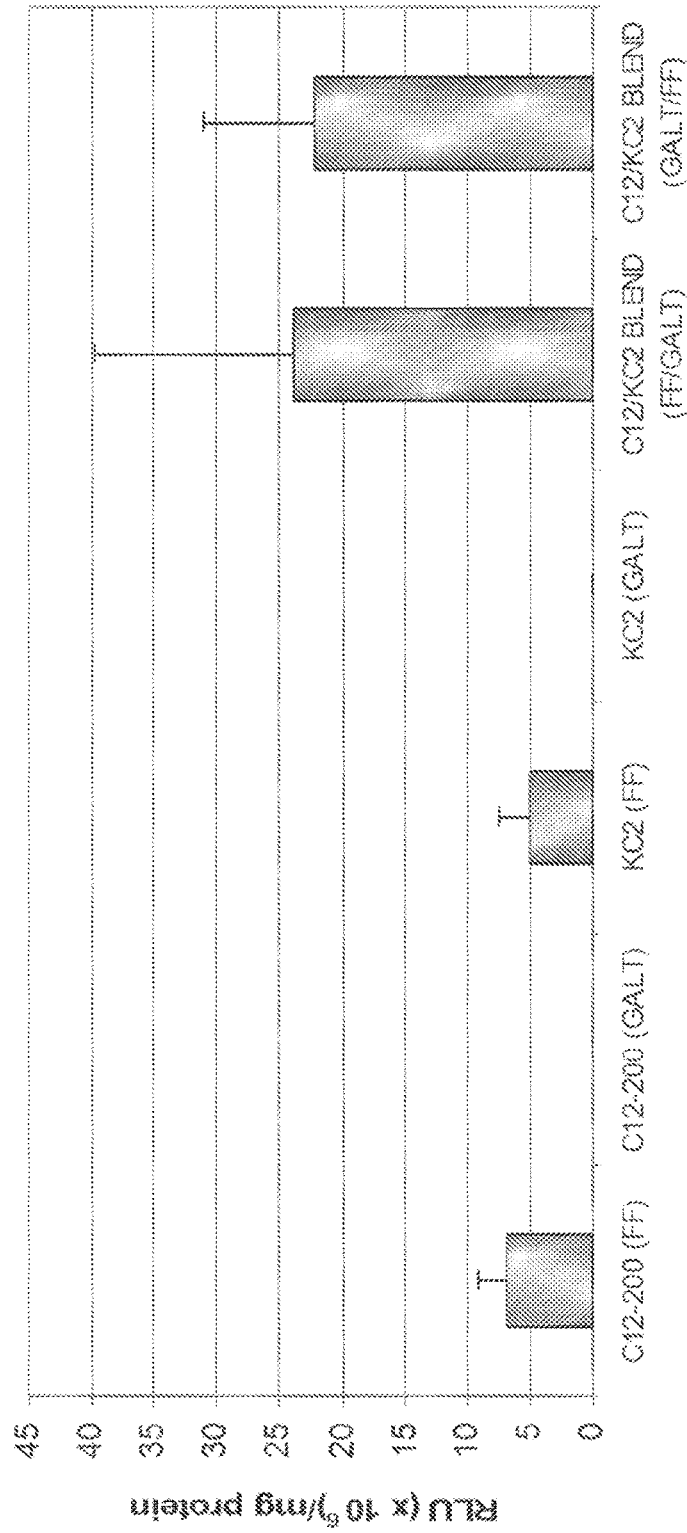
FIG. 5. illustrates the luminescence comparison when blending formulations encapsulating fluorescent (FFL) and non-fluorescent (GALT) mRNA. The C12-200-based formulations evaluated were dosed at 30 µg, while the DLin-KC2-DMA-based formulations were dosed at 90 µg mRNA. The blended formulations were dosed at 120 µg total mRNA. Values are depicted as median RLU/mg of total protein in liver four hours post-administration.

FIG. 5 illustrates a comparison of the median luminescence observed when studying blended formulations encapsulating fluorescent (FFL) and non-fluorescent (GALT) mRNA. The C12-200-based lipid nanoparticle formulations were administered at a dose of 30 μg of mRNA, while the DLin-KC2-DMA-based lipid nanoparticle formulations were administered at a dose of 90 μg of mRNA. The blended formulations were both administered at doses of 120 μg total mRNA. As illustrated in FIG. 5, an enhanced median luminescence was observed in both blended formulations relative to the luminescence observed when individually administering the constituent lipid nanoparticles.

Table 5 lists some representative examples of various cationic lipid-based systems which demonstrate a synergistic production of FFL protein when incorporating a non-fluorescent GALT message in one of the formulations.

As can be seen in Table 5, the synergy is evident across a range of cationic lipids employed (C12-200, DLin-KC2-DMA, HGT4003, ICE, DODAP, etc., Table 5). In some instances, one observes enhancements of over 30-fold higher than the individual formulations administered separately (Table 5, Experiment #14). This was evident when blending a formulation of the disulfide-based lipid HGT4003 encapsulating FFL mRNA with a C12-200-based formulation encapsulating GALT mRNA (Table 5, Experiment #17). The observed mean RLU measured in the livers of mice four hours post-administration was $8.38 \times 10^6$ RLU for the blend as compared to $3.85 \times 10^5$ RLU from the HGT4003-based FFL mRNA-loaded nanoparticle independently. Negligible background fluorescence was observed for all non-fluorescent GALT mRNA loaded lipid nanoparticle groups.

Another example of observed synergistic enhancement when blending a FFL mRNA-loaded lipid nanoparticle with a GALT mRNA-loaded lipid nanoparticle is represented in Experiment #18 (Table 5). A blend of a FFL mRNA-loaded ICE-based lipid nanoparticle with a non-fluorescent GALT mRNA-loaded DLin-KC2-DMA-based lipid nanoparticle (1:1 ratio based on dose of encapsulated mRNA) yielded an observed mean RLU/mg protein value of $1.84 \times 10^5$. This is compared to a value of $3.76 \times 10^4$ RLU/mg protein for the FFL mRNA-loaded ICE-based formulation administered independently. Such a blend afforded an approximate 4.85-fold enhancement in luminescent output.

Thus experiments shown in Table 5 clearly demonstrate that synergistic enhancement with respect to light production does not dependent on both nanoparticles to have a fluorescent message incorporated, suggesting that synergistic effects with respect to blending separate lipid formulations is independent of the incorporated nucleic acid.

TABLE 5

Various cationic lipid-nanoparticle blends and synergistic enhancement of CO-FFL protein luminescence in liver

| Experiment | Lipid Formulation #1 (FFL mRNA) | RLU/mg protein of Formulation #1 | Lipid Formulation #2 (GALT mRNA) | Ratio | Total Dose (ug mRNA) | RLU/mg protein of Blend | Fold Increase in Luminescence |
|---|---|---|---|---|---|---|---|
| 11 | C12-200 | 6,866,021 | DLin-KC2-DMA | 1:3 | 120 | 23,752,692 | 3.46 |
| 12 | C12-200 | 32,560,660 | HGT4003 | 1:3.33 | 130 | 51,323,277 | 1.58 |

TABLE 5-continued

Various cationic lipid-nanoparticle blends and synergistic enhancement of CO-FFL protein luminescence in liver

| Experiment | Lipid Formulation #1 (FFL mRNA) | RLU/mg protein of Formulation #1 | Lipid Formulation #2 (GALT mRNA) | Ratio | Total Dose (ug mRNA) | RLU/mg protein of Blend | Fold Increase in Luminescence |
|---|---|---|---|---|---|---|---|
| 13 | DLin-KC2-DMA | 4,983,048 | C12-200 | 3:1 | 120 | 22,124,581 | 4.41 |
| 14 | DLin-KC2-DMA | 255,921 | ICE | 1:1 | 200 | 7,711,698 | 30.10 |
| 15 | DLin-KC2-DMA | 1,382,039 | HGT4003 | 1:1 | 120 | 1,555,411 | 1.13 |
| 16 | HGT4003 | 137,068 | DLin-KC2-DMA | 1:1 | 120 | 305,285 | 2.22 |
| 17 | HGT4003 | 385,110 | C12-200 | 3.33:1 | 130 | 8,376,000 | 21.72 |
| 18 | ICE | 37,571 | DLin-KC2-DMA | 1:1 | 200 | 184,322 | 4.85 |
| 19 | ICE | 68,562 | DODAP | 1:1 | 200 | 69,480 | 1.01 |
| 20 | DODAP | 8,425 | ICE | 1:1 | 200 | 18,736 | 2.20 |
| 21 | C12-200 | 50,500,335 | DODAP | 1:5 | 150 | 29,515,643 | 0 |
| 22 | DODAP | 25,745 | C12-200 | 5:1 | 150 | 22,064,370 | 8.57 |

Summary of synergistic enhancement of FFL protein luminescence in livers of treated mice (N-4) four hours post administration when blending two separate fluorescent mRNA-loaded liped nonparticles (FFL mRNA) with a non-fluorescent mRNA-loaded lipid nanoparticle (GALT mRNA). Increases rance from 0-30x luminescence over the the single formulation demonstrating a synergistic enhancement. The ratios are representative of the fluorescent formulation dose: non-fluorescent formulation dose. The lipids listed represent the cationic lipid composition of each formulation. Values based on observable enhancement four hours post-administration.

Figure 6:
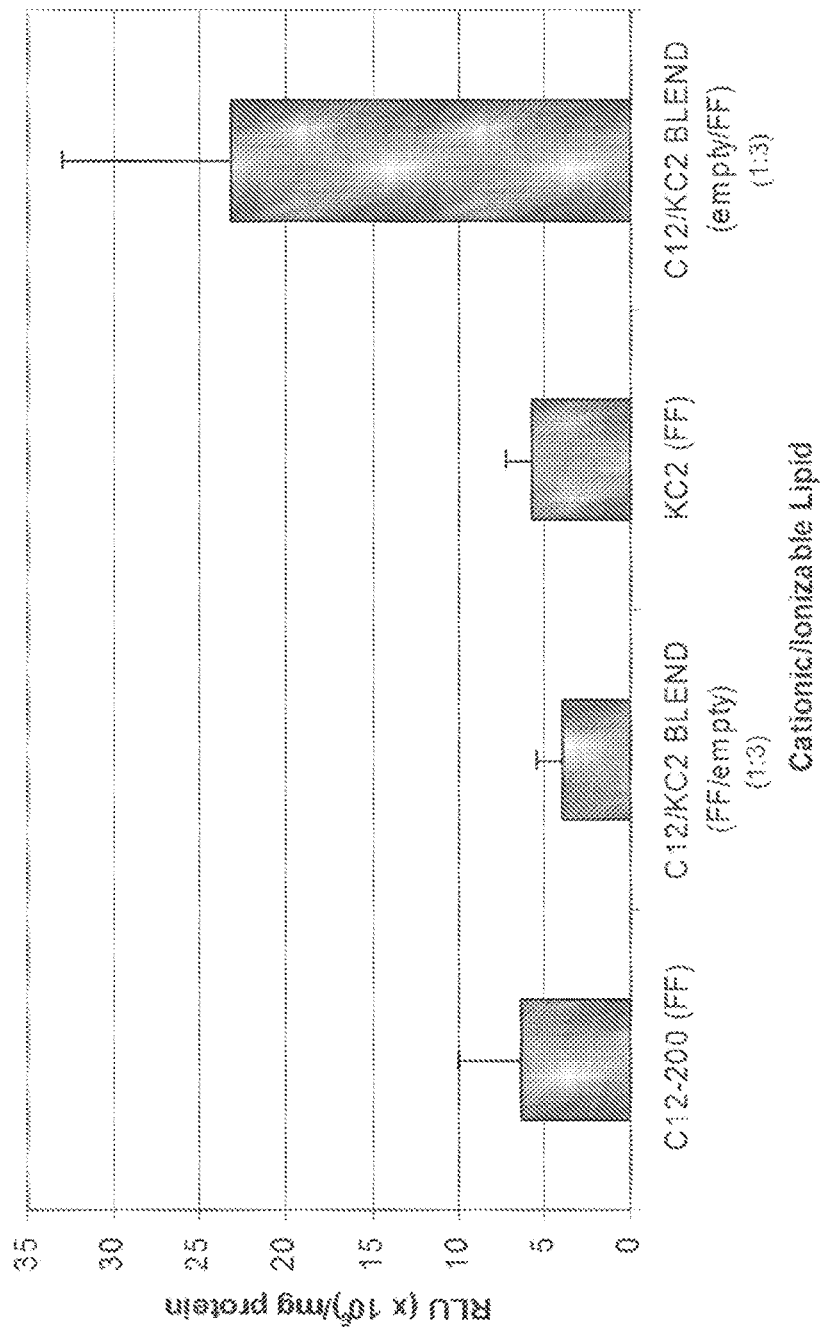
FIG. 6. illustrates the luminescence comparison of treated livers when blending formulations encapsulating fluorescent (FFL) with empty lipid nanoparticles (no mRNA). All C12-200-based lipid nanoparticles were dosed at 30 µg mRNA (or equivalent) while DLin-KC2-DMA-based formulations were dosed at 90 µg mRNA (or equivalent). Blended formulations were dosed at 120 µg equivalent mRNA. Values are depicted as median RLU/mg of total protein in liver four hours post-administration.

We then tested if the synergistic effect with respect to the blending of different lipid formulations dependents on the presence of messenger RNA. To that end, empty liposomal nanoparticles (without any mRNA encapsulated) were tested as possible synergistic agents. Interestingly, blending an empty C12-200-based cationic lipid nanoparticle with a FFL mRNA-loaded DLin-KC2-DMA-based cationic lipid nanoparticle resulted in a strong synergistic enhancement of luminescence (4-fold increase) FIG. 6, Table 6, Experiment #24) while the respective inverse (FFL mRNA-loaded C12-200 nanoparticles with empty DLin-KC2-DMA liposomal nanoparticle blend resulted in no enhancement (FIG. 6, Table 6 (Experiment #23)).

These results indicate that the synergistic effect may be dependent on the presence of message, at least in some cases. Without wishing to be bound by any particular theory, it is contemplated that two possible lipid-specific mechanisms may be leading to synergistic effect with or without the presence of mRNA.

TABLE 6

Effect of mRNA encapsulation on blending enhancement

| Experiment | Lipid Formulation #1 (FFL mRNA) | RLU/mg protein of Formulation #1 | Lipid Formulation #2 (no mRNA) | Ratio | Total Dose (ug mRNA) | RLU/mg protein of Blend | Fold Increase in Luminescence |
|---|---|---|---|---|---|---|---|
| 23 | C12-200 | 6,407,934 | DLin-KC2-DMA | 1:3 | 120 | 3,940,501 | 0 |
| 24 | DLin-KC2-DMA | 5,694,440 | C12-200 | 3:1 | 120 | 23,272,244 | 4.09 |

Example 7. Synergistic Effect of Liposome-Derived Nanoparticles Via ICV Delivery As shown in the above examples, the synergistic increase in protein production has been observed in the liver over multiple systems when test articles have been administered intravenously as described (vide supra). It is contemplated that the synergistic effect may be applied further, not only to diseases specific to the liver but anywhere one may require treatment, i.e. lung, spleen, kidney, heart, eye, central nervous system, brain, etc. To confirm that, the present example demonstrates a synergistic enhancement of FFL protein luminescence when delivering a blend of two separate FFL mRNA-loaded lipid nanoparticles via intracerebroventricular (ICV) administration.

Figure 7:
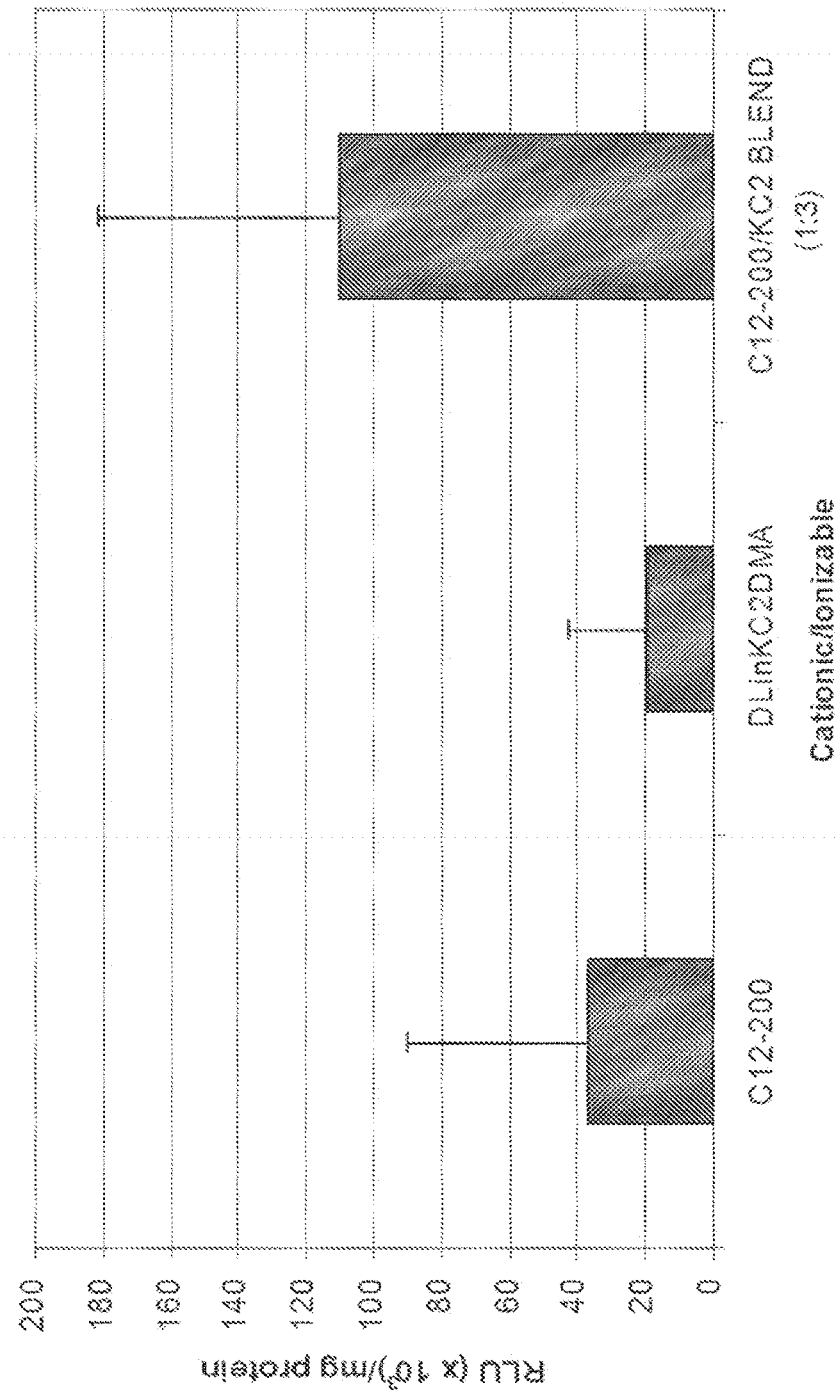
FIG. 7. illustrates the luminescence output of firefly luciferase protein in the brain tissues of mice following intracerebroventricular (ICV) administration of firefly luciferase (FFL) mRNA-encapsulated lipid nanoparticles. The formulation compared were C12-200-based formulations (0.96 µg dose) and DLin-KC2-DMA-based formulations (2.87 µg dose) both individually and relative to a blend of these two formulations in a 1:3 ratio (3.83 µg dose). Values are depicted as median RLU/mg of total protein in brain four hours post-administration.

As shown in FIG. 7, C12-200-based FFL mRNA-encapsulated lipid nanoparticles blended with FFL mRNA-loaded DLin-KC2-DMA-based lipid nanoparticles in a 1:3 ratio (based on mRNA dose) resulted in an approximate 2.0-fold enhancement of FFL protein luminescence as compared to the sum of the luminescent output of each individual formulation ($1.11 \times 10^5$ RLU vs $5.57 \times 10^4$ RLU, respectively). To evaluate whether the blended formulations were capable of demonstrating a synergistic enhancement of observed luminescence in the cells and tissues of the central nervous system, additional studies were conducted wherein blended formulations were administered to animals via the intracerebroventricular (ICV) route of administration. In particular, the synergistic enhancement in the expression of ICV-administered exogenous mRNA encapsulated in a blended lipid nanoparticle formulation and the corresponding production of the firefly luciferase protein encoded thereby (as demonstrated by the enhanced median luminescent output) was evaluated by comparing median luminescence output observed following ICV administration of the blended lipid formulations to the median luminescence observed output observed following ICV administration of the individual constituent lipid nanoparticle formulations.

Example 8. Synergistically Enhancing the Expression of Secreted Proteins

This example demonstrates that the synergistic phenomenon also applies towards the idea of a "depot" effect for secretion of a desired protein into the bloodstream. For example, the delivery of mRNA encoding human erythropoietin (EPO) can be packaged via a lipid nanoparticle and injected into a mouse. The formulation can accumulate within the liver and/or other organs and transcribe the mRNA to the desired EPO protein. Upon its expression, the protein can secrete from the liver (organ) and function as necessary.

Figure 8:
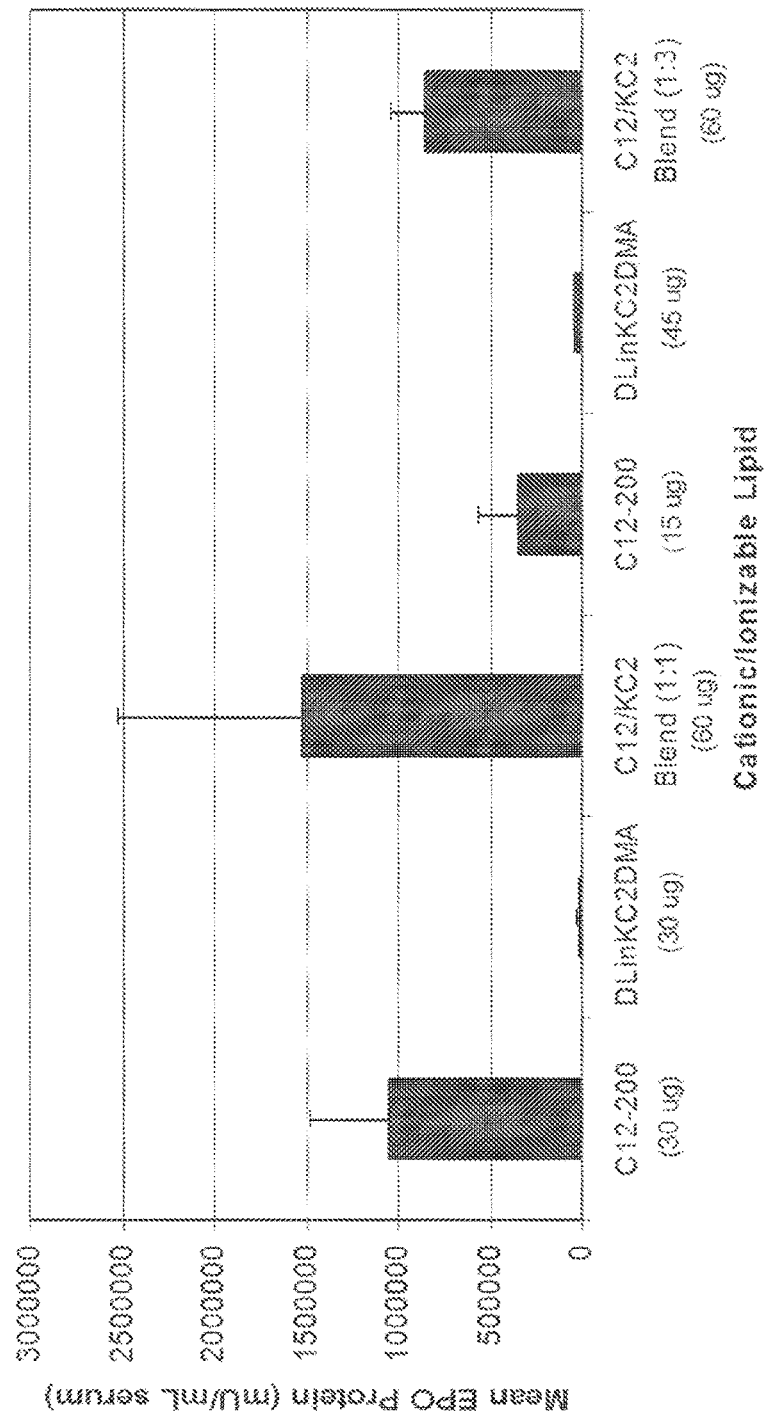
FIG. 8. illustrates a comparison of secreted human erythropoietin (EPO) protein following intravenous delivery of EPO mRNA-encapsulated lipid nanoparticles. Blood samples were taken four hours post-injection.

This notion was tested using a human EPO mRNA-loaded C12-200-based lipid nanoparticle, a human EPO mRNA-loaded DLin-KC2-DMA-based lipid nanoparticle and a blend of the two formulations in various ratios. Fully secreted human EPO was detected via ELIA and immuno-blot analyses (FIGS. 8 and 9, respectively) four hours after intravenous administration of these nanoparticles in mice. Further, upon treatment with a blend of the two single formulations, one observed a synergistic enhancement of human EPO protein secreted into the bloodstream as compared to the sum of each individual formulation counterpart (FIG. 8). This enhancement was more pronounced upon blending at a ratio of 1:3 (~2-fold) as compared to 1:1 (~1.4 fold) (C12-200-based formulation; DLin-KC2-DMA-based formulation).

Figure 9:
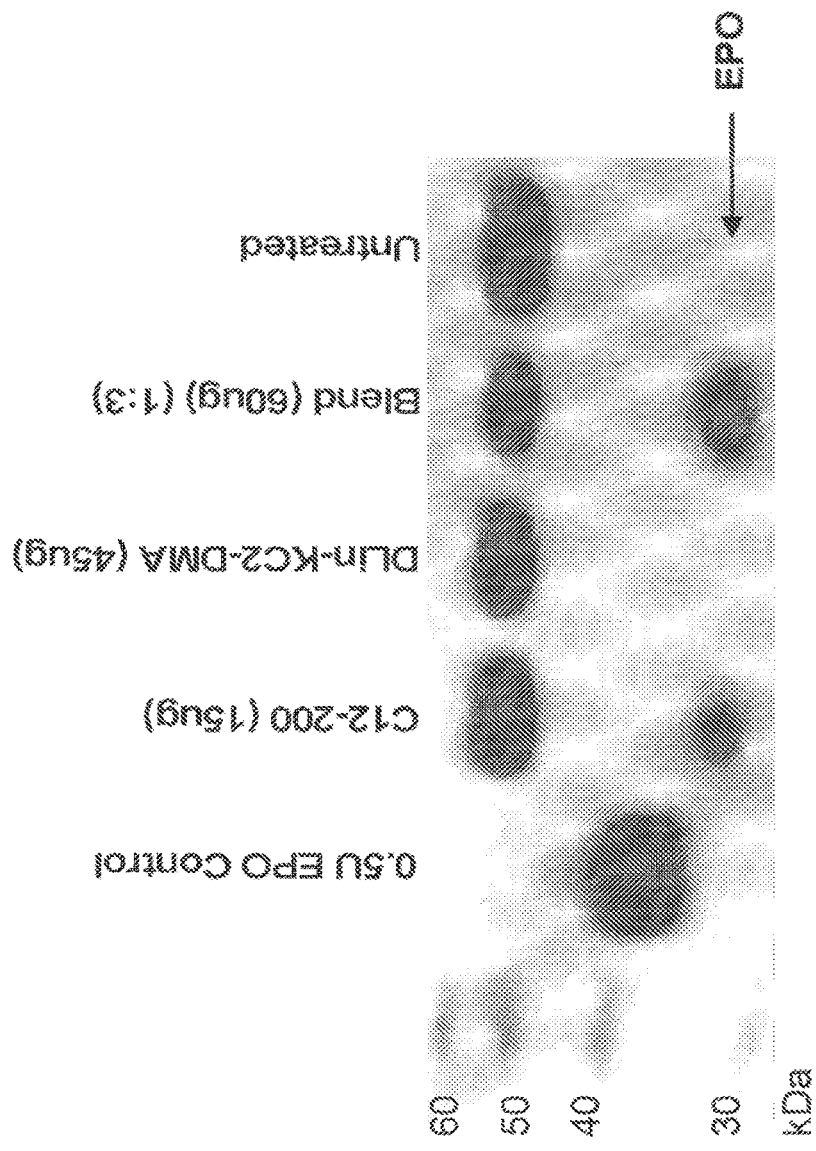
FIG. 9. Illustrates synergistic augmentation of protein production when analyzed via western blot. A blend of a human EPO mRNA-loaded C12-200-based lipid nanoparticle with an analogous DLin-KC2-DMA-loaded lipid nanoparticle shows strong band (Lane 4) significant of human EPO protein isolated from the serum four hours post-administration. The lane corresponding to an individual C12-200 formulation (Lane 2) yields a moderately detected band while that of the DLin-KC2-DMA-based formulation (Lane 3) is undetectable.

This synergistic augmentation of protein production is more pronounced when analyzed via western blot. As depicted in FIG. 9, a blend of a human EPO mRNA-loaded C12-200-based lipid nanoparticle with an analogous DLin-KC2-DMA-loaded lipid nanoparticle shows a strong band (Lane 4) significant of human EPO protein isolated from the serum four hours post-administration. The lane corresponding to an individual C12-200 formulation (Lane 2) yields a moderately detected band while that of the DLin-KC2-DMA-based formulation (Lane 3) is undetectable. One can qualitatively observe an enhancement of protein production as compared to the "additive total" from each individual formulation.

These observations confirm that this synergistic phenomenon is not specific to a luciferase system, but can be applicable to other target proteins generally. In addition, as demonstrated in Example 7, the synergistic phenomenon is observed not only via intravenous delivery to the liver, but also via intracerebroventricular delivery to the brain. In addition to delivering to specific target organs, the blending of two formulations can synergistically enhance the production of secreted proteins as demonstrated with our human EPO system.

The synergistic enhancement presented here suggests that equivalent therapeutic efficacy can be achieved via administration of a significantly lower dose than previously anticipated. The ability to create a synergistic production of protein via lipid-based nanoparticle delivery of mRNA allows for a much greater therapeutic window for the treatment of a host of diseases. The successful delivery of such mRNA to the liver and in particular, to hepatocytes, can be used for the treatment and the correction of in-born errors of metabolism that are localized to the liver. Diseases such as ASD and OTC among other urea cycle disorders may be treated through mRNA therapy of the missing gene. Metabolic zonation of the urea cycle to hepatocytes means that providing the missing enzyme in these cells should greatly improve normal biochemical processing in individuals with these disorders. To achieve this in a synergistic fashion via the process described above, one could administer a much lower dose (~2 to 30-fold lower) and achieve equal or greater efficacy while mediating any adverse or toxic events.

We claim:

1. A method of delivering a messenger RNA (mRNA) to a subject, comprising administering to the subject a single pharmaceutical composition comprising a blend of at least a first and a second separately formed, non-identical lipid nanoparticles, each lipid nanoparticle comprising one or more PEG-modified lipids,
   wherein the first lipid nanoparticle comprises a first mRNA and the second lipid nanoparticle comprises a second mRNA,
   wherein the first lipid nanoparticle comprises a first cationic lipid and the second lipid nanoparticle comprises a second cationic lipid,
   wherein the first cationic lipid and the second cationic lipid are non-identical, and
   wherein an expression of a protein or a peptide encoded by the first mRNA or the second mRNA following the administration of the pharmaceutical composition to the subject exceeds the expression of the protein or the peptide encoded by the first mRNA or the second mRNA administered with the first lipid nanoparticle or the second lipid nanoparticle respectively, but without the other lipid nanoparticle by at least about two-fold.

2. The method of claim 1, wherein the first cationic lipid is selected from the group consisting of C12-200, DOTAP (1,2-dioleyl-3-trimethylammonium propane), DODAP (1,2-dioleyl-3-dimethylammonium propane), DOTMA (1,2-di-O-octadecenyl-3-trimethylammonium propane), DLinDMA, DLin-KC2-DMA, HGT4003 and ICE.

3. The method of claim 1, wherein the first lipid nanoparticle and the second lipid nanoparticle comprise one or more helper lipids.

4. The method of claim 3, wherein the one or more helper lipids are selected from the group consisting of DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DPPE (1,2-dipalmitoyl-sn-glycero-3-phosphoethanolamine), DMPE (1,2-dimyristoyl-sn-glycero-3-phosphoethanolamine), DOPG (,2-dioleoyl-sn-glycero-3-phospho-(1'-rac-glycerol)) and cholesterol.

5. The method of claim 1, wherein the one or more PEG-modified lipids comprises a poly(ethylene)glycol chain of up to 5 kDa in length covalently attached to a lipid comprising one or more alkyl chains of C6-C20 in length.

6. The method of claim 1, wherein the first lipid nanoparticle or the second lipid nanoparticle comprises one or more lipids selected from the group consisting of ICE, DSPC, CHOL, DODAP, DOTAP and C8-PEG-2000.

7. The method of claim 1, wherein the first mRNA or the second mRNA encodes an enzyme.

8. The method of claim 1, wherein the first mRNA or the second mRNA encodes a protein or a peptide, and the protein or the peptide encoded by the first mRNA or the second mRNA is secreted from one or more cells.

9. The method of claim 1, wherein the first mRNA is selected from SEQ ID NO: 2 or SEQ ID NO: 3.

10. The method of claim 1, wherein the first mRNA or the second mRNA comprises a chemical modification that renders the mRNA more stable.

11. The method of claim 1, wherein the expression of the protein or the peptide encoded by the first mRNA following the administration of the pharmaceutical composition to the subject exceeds the expression of the protein or the peptide encoded by the first mRNA administered with the first lipid nanoparticle but without the second lipid nanoparticle by at least about five-fold, or by at least about ten-fold.

12. The method of claim 11, wherein the first mRNA is the same as the second mRNA.

13. The method of claim 11, wherein the first mRNA is different than the second mRNA.

14. The method of claim 1, wherein the a ratio of the first lipid nanoparticle to the second lipid nanoparticle in the pharmaceutical composition is about 1:1 or about 2:1 or about 3:1 or about 4:1.

* * * * *